United States Patent
Iliopoulos

(10) Patent No.: US 12,414,960 B2
(45) Date of Patent: Sep. 16, 2025

(54) ANALOGUES OF OLEUROPEIN AND OLEACEIN AND USES THEREOF

(71) Applicant: Attica Sciences Ltd., Manchester (GB)

(72) Inventor: Dimitrios Iliopoulos, Los Angeles, CA (US)

(73) Assignee: ATTICA SCIENCES LTD., Manchester (GB)

( * ) Notice: Subject to any disclaimer, the term of this patent is extended or adjusted under 35 U.S.C. 154(b) by 0 days.

(21) Appl. No.: 17/500,099

(22) Filed: Oct. 13, 2021

(65) Prior Publication Data

US 2022/0110962 A1    Apr. 14, 2022

Related U.S. Application Data

(60) Provisional application No. 63/091,059, filed on Oct. 13, 2020.

(51) Int. Cl.

| | | |
|---|---|---|
| A61K 31/7048 | (2006.01) | |
| A61K 31/22 | (2006.01) | |
| A61K 31/222 | (2006.01) | |
| A61K 31/265 | (2006.01) | |
| A61K 31/404 | (2006.01) | |
| A61K 35/17 | (2025.01) | |
| A61P 35/00 | (2006.01) | |
| A61P 37/06 | (2006.01) | |
| C07C 69/738 | (2006.01) | |
| C07C 327/22 | (2006.01) | |
| C07D 209/12 | (2006.01) | |
| C07H 17/04 | (2006.01) | |

(52) U.S. Cl.
CPC .......... *A61K 31/7048* (2013.01); *A61K 31/22* (2013.01); *A61K 31/222* (2013.01); *A61K 31/265* (2013.01); *A61K 31/404* (2013.01); *A61K 35/17* (2013.01); *A61P 35/00* (2018.01); *A61P 37/06* (2018.01); *C07C 69/738* (2013.01); *C07C 327/22* (2013.01); *C07D 209/12* (2013.01); *C07H 17/04* (2013.01)

(58) Field of Classification Search
CPC .............................. C07H 17/04; C07C 29/738
See application file for complete search history.

(56) References Cited

FOREIGN PATENT DOCUMENTS

| EP | 2218441 A1 | 8/2010 |
|---|---|---|
| EP | 1888091 B1 | 1/2013 |
| WO | 2001/76579 A1 | 10/2001 |

OTHER PUBLICATIONS

Samara et al., "New semi-synthetic analogs of oleuropein show improved anticancer activity in vitro and in vivo" European Journal of Medicinal Chemistry vol. 137 pp. 11-29 DOI 10.1016/j.ejmech.2017.05.029 (Year: 2017).*
Bernard et al., "IL-1β induces thymic stromal lymphopoietin and an atopic dermatitis-like phenotype in reconstructed healthy human epidermis", Journal of Pathology, 2017, pp. 234-245, vol. 242.
Bhaskar et al., "Monoclonal antibodies targeting IL1 beta reduce biomarkers of atherosclerosis in vitro and inhibit atherosclerotic plaque formation in Apolipoprotein E-deficient mice", Atherosclerosis, 2011, pp. 313-320, vol. 216.
Chekaoui et al., "Increased IL1-β levels are associated with an imbalance of "oxidant/antioxidant" status during Behcet's disease", Sep. 2018, pp. 95-102, vol. 29(3).
Chima et al., "TNF inhibitors for psoriasis", Seminars in Cutaneous Medicine and Surgery, Sep. 2018, vol. 37.
Chousterman et al., "Cytokine storm and sepsis disease pathogenesis", Semin Immunopathol, 2017, pp. 517-528, vol. 39.
Daina et al., "SwissTargetPrediction: updated data and new features for efficient prediction of protein targets of small molecules", Nucleic Acids Research, May 20, 2019, Web Server Issue W357-W364, vol. 47.
Radner et al., "Anti-TNF in rheumatoid arthritis: an overview", Wien Med Wochenschr, 2015, pp. 3-9, vol. 65.
Shakoory et al., "Interleukin-1 Receptor Blockade Is Associated With Reduced Mortality in Sepsis Patients With Features of Macrophage Activation Syndrome: Reanalysis of a Prior Phase III Trial", Critical Care Medicine, Feb. 2016, p. 275-, vol. 44 (2).
Tobin et al., "TNFa Inhibitors in the Treatment of Psoriasis and Psoriatic Arthritis", Biodrugs, 2005, pp. 47-57, vol. 19 (1).
Ye et al., "The pathogenesis and treatment of the 'Cytokine Storm' in COVID-19", Journal of Infection, 2020, pp. 607-613, vol. 80.
Acquaviva et al., "Antiproliferative effect of oleuropein in prostate cell lines", International Journal of Oncology, Apr. 5, 2012, pp. 1-2 (Abstract), hhttps://doi.org/10.3892/ijo.2012.1428.
Al-Sadi et al., "Mechanism of Interleukin-1β Induced-Increase in Mouse Intestinal Permeability In Vivo", Journal of Interferon & Cytokine Research, 2012, pp. 474-484, vol. 32(10).
Angeloni et al., "Bioactivity of Olive Oil Phenols in Neuroprotection", International Journal of Molecular Sciences, Oct. 25, 2017, pp. 1-27, vol. 18.
Batarseh et al., "Oleocanthal-rich extra-virgin olive oil enhances donepezil effect by reducing amyloid-β load and related toxicity in a mouse model Alzheimer's disease", J. Nutr. Biochem., May 2018, pp. 1-23, vol. 55.
Brand-Williams, "Use of a Free Radical method to Evaluate Antioxidant Activity", Lebensm.-Wiss. u. Technol., 1995, pp. 25-30, vol. 28(1).
Carrer et al., "Acetyl-CoA Metabolism Supports Multistep Pancreatic Tumorigensis", Cancer Discovery, Jan. 9, 2019, pp. 416-435.
Promega, "CellTiter-Glo Luminescent Cell Viability Assay", Promega Technical Bulletin, Instructions for Use of Products G7570, G7571, G7572 and G7573, Mar. 2015, pp. 1-15.

(Continued)

*Primary Examiner* — Eric Olson
(74) *Attorney, Agent, or Firm* — Pillsbury Winthrop Shaw Pittman LLP

(57) ABSTRACT

Analogues of oleuropein and oleacein and pharmaceutically acceptable salts thereof and processes for the preparation of these compounds are disclosed. The invention further relates to use of oleuropein and oleacein analogues for the treatment of inflammatory disorders, cardiometabolic disorders, and cancer.

32 Claims, 49 Drawing Sheets

(56) References Cited

OTHER PUBLICATIONS

Choy et al., "Translating IL-6 biology into effective treatments", Nature Reviews, Rheumatology, Jun. 2020, pp. 335-345, vol. 16.
Crivori et al., "Computational Models for Identifying Potential P-Glycoprotein Substrates and Inhibitors", Molecular Pharmaceutics, Dec. 8, 2005, pp. 33-44, vol. 3(1).
Santa Cruz et al., "Interleukin-6 Is a Biomarker for the Development of Fatal Severe Acute Respiratory Syndrome Coronavirus 2 Pneumonia", Frontiers in Immunology, Feb. 2021, pp. 1-10, vol. 12, Article 613422.
Cuyas et al., "Computational de-orphanization of the olive oil biophenol oleacein: Discovery of new metabolic and epigenetic targets", Food and Chemical Toxicology, Sep. 2019, pp. 1-3.
Daina et al., "SwissADME: a free web tool to evaluate pharmacokinetics, drug-likeness and medicinal chemistry friendliness of small molecules", Scientific Reports, Mar. 3, 2017, pp. 1-13, vol. 7 (42717).
Ghashghaei et al., "Identification of a Radiosensitivity Molecular Signature Induced by Enzalutamide in Hormone-sensitive and Hormone-resistant Prostate Cancer Cells", Scientific Reports, Jun. 20, 2019, pp. 1-12, vol. 9(8838).
Greenspan et al., "Nile Red: A Selective Fluorescent Stain for Intracellular Lipid Droplets", The Journal of Cell Biology, Mar. 1985, pp. 965-973, vol. 100.
Hatzivassiliou et al., "ATP citrate lyase inhibition can suppress tumor cell growth", Cancer Cell, Oct. 2005, pp. 311-321, vol. 8.
Kouka et al., "The Polyphenolic Composition of Extracts Derived from Different Greek Extra Virgin Olive Oils Is Correlated with Their Antioxidant Potency", Oxidative Medicine and Cellular Longevity, Mar. 20, 2019, pp. 1-13.
Miller et al., "A novel method for measuring antioxidant capacity and its application to monitoring the antioxidant status in premature neonates", Clinical Science, 1993, pp. 407-412, vol. 84.
Montoya et al., "Oleocanthal Modulates LPS-Induced Murine Peritoneal Macrophages Activation via Regulation of Inflammasome, Nrf-2/HO-1, and MAPKs Signaling Pathways", Journal of Agricultural and Food Chemistry, May 1, 2019, pp. 5552-5559, vol. 67.
Nimse et al., "Free radicals, natural antioxidants, and their reaction mechanisms", Royal Society of Chemistry Advances, 2015, pp. 27986-28006, vol. 5.
Perjesi et al., "Kinetic Analysis of Some Chalcones and Synthetic Chalcone Analogues on the Fenton-Reaction Initiated Deoxyribose Degradation Assay1", The Open Medicinal Chemistry Journal, 2011, pp. 61-67, vol. 5.
Przychodzen et al., "PTP1B phosphatase as a novel target of oleuropein activity in MCF-7 breast cancer model", Toxicolocy in Vitro, Dec. 2019, p. 1, Abstract.
Ruperto et al., "Two Randomized Trials of Canakinumab in Systemic Juvenile Idiopathic Arthritis", The New England Journal of Medicine, Dec. 20, 2012, pp. 2396-2406, vol. 267(25).
Rutgeerts et al., "Infliximab for Induction and Maintenance Therapy for Ulcerative Colitis", The New England Journal of Medicine, Dec. 8, 2005, pp. 2462-2476, vol. 353(23).
Samara et al., "New semi-synthetic analogs of oleuropein show improved anticancer activity in vitro and in vivo", European Journal of Medicinal Chemistry, May 12, 2017, pp. 11-29, vol. 137.
Sarikaki et al., "Biomimetic Synthesis of Oleocanthal, Oleacein, and Their Analogues Starting from Oleuropein, A Major Compound of Olive Leaves", Journal of Natural Products, May 22, 2020, pp. 1735-1739, vol. 83.
Scudiero et al., "Evaluation of a Soluble Tetrazolium/Formazan Assay for Cell Growth and Drug Sensitivity in Culture Using Human and Other Tumor Cell Lines", Cancer Research, Sep. 1, 1998, pp. 4827-4833, vol. 48.
Servili et al., "Biological Activities of Phenolic Compounds of Extra Virgin Olive Oil", Antioxidants, Dec. 20, 2013, pp. 1-23, vol. 3.
Sharadha et al., "An overview on topical drug delivery system—Updated review", International Journal of Research In Pharmaceutical Sciences, 2020, pp. 368-385, vol. 11(1).
Sherif et al., "Oleuropein potentiates anti-tumor activity of cisplatin against HepG2 through affecting proNGF/NGF balance", Life Sciences, Feb. 21, 2018, pp. 87-93, vol. 198, Abstract.
Spanou et al., "Assessment of Antioxidant Activity of Extracts from Unique Greek Varieties of Leguminosae Plants Using In vitro Assays", Anticancer Research, 2007, pp. 3403-3410, vol. 27.
Xu et al., "Oleuropein enhances radiation sensitivity of nasopharyngeal carcinoma by downregulating PDRG1 through HIF1α-repressed microRNA-519d", Journal of Experimental & Clinical Cancer Research, 2017, pp. 1-10, vol. 36(3).
Zaidi et al., "ATP-Citrate Lyase: A Key Player in Cancer Metabolism", American Association for Cancer Research, Aug. 1, 2012, pp. 3709-3714, vol. 72(15).
Patent Cooperation Treaty, International Search Report issued in PCT/IB2021/059416, Jan. 19, 2022, pp. 1-5.
Fu et al., "Qualitative screening of phenolic compounds in olive leaf extracts by hyphenated liquid chromatography and preliminary evaluation of cytotoxic activity against human breast cancer cells", Anal Bioanal Chem., 2010 pp. 643-654, vol. 397(2).
Smith et al., "Synthesis and assignment of absolute configuration of (−)-oleocanthal: a potent naturally occurring non-steroidal anti-inflammatory and anti-oxidant agent derived from extra virgin olive oils", Organic Letters, 2005, pp. 5075-5078, vol. 7(22).
Shakoory et al., "Interleukin-1 Receptor Blockade Is Associated With Reduced Mortality in Sepsis Patients With Features of Macrophage Activation Syndrome: Reanalysis of a Prior Phase III Trial", Critical Care Medicine, Feb. 2016, pp. 275-, vol. 44 (2).

* cited by examiner

Structures of Phenolic Compounds in Extra Virgin Olive Oil

DPPH Radical Scavenging Assay

ABTS Radical Cation Scavenging Assay

Superoxide Anion Radical Scavenging Assay

Deoxyribose Degradation Assay

Ferric Reducing Antioxidant Power (FRAP) Assay

Plasmid Relaxation Assay

1: Control
2: Plasmid + oxidative agent
3-7: Plasmid + oxidative agent + antioxidant compound
8: Antioxidant compound XTT Assay

Effects of GS Compounds on MKN-45 Gastric Cancer Cell Growth

GS27 and Other GS Compounds Effectively Block HCT-116 Colon Cancer Cell Growth

**GS Compounds Do Not Affect the Growth of
MCF-10A Normal Epithelial Cells**

Effect of GS27 on Activity Levels of Proteins Involved in Cellular Metabolism and Inflammatory Pathways

Effect of GS Compounds on ACLY Enzymatic Activity

**GS27 is More Effective Than Other ACLY inhibitors in
Reducing Panc-1 Pancreatic Cancer Cell Growth**

Effects of GS Compounds on Intestinal Permeability

Effects of GS Compounds on Regulation of P-glycoprotein Substrate

GS27 Has No Effect on Raw 264.7 Macrophage Cell Growth

GS27 Maximum Tolerated Dose (MTD) Studies in Rodents

GS27 is More Effective than NDI-091143 in Sensitizing Castration-resistant Prostate Cancer Cells to AR Antagonism under Androgen Depletion

GS27 Suppresses HCT-116 Colon Tumor Growth in Xenograft Mice Relative to GS19, Which Does Not Have an Effect

GS27 Suppresses HepG2 Liver Tumor Growth in Mice More Effectively Than Doxorubicin Chemotherapy Treatment

GS27 Inhibits AsPC-1 Pancreatic Cancer Tumor Growth in Mice

$*p<0.05$, $ p<0.01$, $* p<0.001$, $**** p<0.0001$ vs vehicle

GS27 is a Direct Potent Inhibitor of ACLY Activity

GS27-treated AsPC-1 Pancreatic Cancer Tumors Show Reduced Intracellular Lipid Content

ANALOGUES OF OLEUROPEIN AND OLEACEIN AND USES THEREOF

FIELD OF THE INVENTION

The present invention relates to analogues of oleuropein and oleacein, processes for the preparation of these compounds, and pharmaceutical compositions thereof. The invention further relates to use of oleuropein and oleacein analogues for the treatment of inflammatory disorders, cardiometabolic disorders, and cancer.

BACKGROUND OF THE INVENTION

Extra virgin olive oil (EVOO) has attracted significant attention in the recent past due to its biological activities and its positive effects to different aspects of human health (Servili, Maurizio et al., Antioxidants, 2014, 3(1): 1-23). Although EVOO consists mainly of oleic acid and other fatty acids, some minor phenolic compounds are considered to be responsible for its health benefits. Representative compounds include tyrosol, hydroxytyrosol, the glycosylated seco-iridoids oleuropein and ligstroside, and the decarboxymethylated aglycones oleacein and oleocanthal. (FIG. 1)

The identification of oleocanthal as a natural anti-inflammatory compound, targeting cyclooxygenases and having potency similar to that of ibuprofen, has increased interest in its biological properties (Beauchamp, Gary K. et al., Nature, 2005, 437(7055): 45-46). More recent studies have shown that oleocanthal also has neuroprotective properties related to Alzheimer's disease (Batarseh, Yazan S. et al., J Nutr Biochem, May 2018, 55: 113-23) and that oleacein has anti-oxidant properties reducing intracellular reactive oxygen species (ROS) levels (Montoya, Tatiana et al., J Agric Food Chem, 2019, 67: 5552-55599). Furthermore, both oleocanthal and oleacein have been found to have antiproliferative activities related to breast, liver, prostate, ovarian, cervical and nasopharyngeal cancers (Przychodzen, Paulina et al. Toxicol in Vitro, December 2019, 61: 104624; Sherif, Iman O. et al., Life Sci, April 2018, 198: 87-93; Acquaviva, Rosaria et al. Int J Oncol, July 2012, 41(1): 31-38; and Xu, Ting et al., J Exp Clin Cancer Res, January 2017, 36(3): 1-10).

Although these are promising results, all studies showing antiproliferative effects of EVOO phenols, including oleocanthal, have used artificially high doses (200 μM-1000 μM). More typically, a compound would be tested for its anti-cancer properties at doses in the range of 0.01 μM to 100 μM, which are translatable into human doses. For example, in vivo studies with oleocanthal at a concentration of 500 μM has been found to reduced LNCaP prostate cancer cell growth (Acquaviva, Rosaria et al. Int J Oncol, July 2012, 41(1): 31-38), while a prostate cancer FDA-approved drug, enzalutamide, is able to achieve similar effect at a 10 μM concentration (Ghashghaei, Maryam et al., Sci Rep, 2019, 9: 8838), which is a 50-fold lower concentration. Importantly, the effects on non-cancer cell growth of EVOO phenols at those high concentrations has not been evaluated in order to establish a safety profile.

Furthermore, the pharmacokinetics properties of EVOO phenols, including oleocanthal and oleacein, are not very favorable. After olive oil consumption, phenolic compounds are quickly metabolized and absorbed. Through the gastro intestinal tract, secoiridoid aglycones such as oleuropein and ligstroside are mainly hydrolyzed into elenolic acid plus hydroxytyrosol and tyrosol, respectively. Hydroxytyrosol and tyrosol are absorbed in a dose-dependent manner, their peak plasma levels are found 1 h after ingestion, while peak urine concentrations are detected 0-2 h after consumption (Angeloni, Cristina et al., 2017, Int J Mol Sci, 18: 22-30).

Accordingly, there is an ongoing need for the development of chemically modified EVOO phenolic compounds for use as therapeutic agents that are more potent than the natural products and have improved pharmacokinetic properties.

SUMMARY OF THE INVENTION

In certain embodiments, the invention provides analogues of oleuropein and oleacein. In one embodiment, such compounds include those of Formula (I):

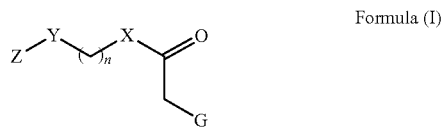

Formula (I)

or a pharmaceutically acceptable salt thereof; wherein n is an integer from 0 to 18;

X is O, S, or NH;

Y is $CH_2$, O, S, or NH;

Z is alkyl, alkenyl, alkynyl, cycloalkyl, aryl, or heterocyclyl, each of which is optionally substituted;

the group G is either G1 or G2:

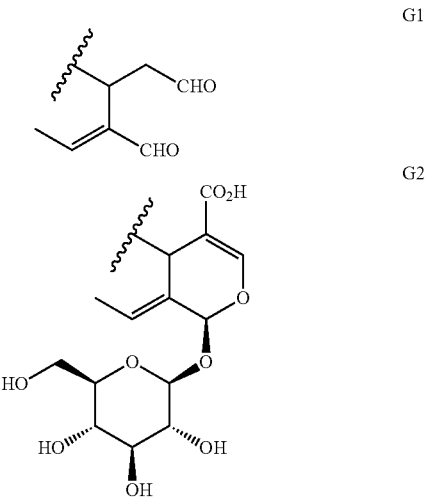

wherein:

if X=O and n=0, then Y=$CH_2$ and Z=aryl, substituted aryl, heteroaryl, or substituted heteroaryl;

if X=O, n=1 and Y=$CH_2$, then Z is not cyclohexyl, phenyl, or substituted phenyl; and wherein the compound is not (2S,3E,4S)-2H-pyran-4-acetic acid, 5-carboxy-3-ethylidene-2-(β-D-glucopyranosyloxy)-3,4-dihydro-4-hexadecyl ester or (3S,4E)-4-hexenoic acid, 4-formyl-3-(2-oxoethyl)-, pentyl ester.

In another embodiment, the invention includes compounds of Formula (II):

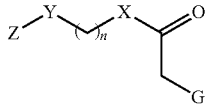

Formula (II)

or a pharmaceutically acceptable salt thereof; wherein:
n is an integer from 1 to 18;
X is O, S, or NH;
Y is O, S, or NH;
Z is alkyl, alkenyl, alkynyl, cycloalkyl, aryl, or heterocyclyl, each of which is optionally substituted; and
the group G is either G1 or G2:

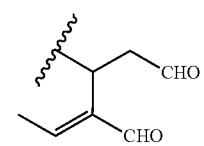

G1

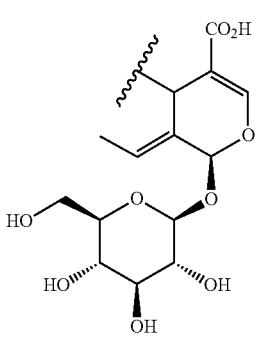

G2

In another embodiment, the invention further includes compounds of Formula (III):

Formula (III)

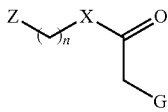

or a pharmaceutically acceptable salt thereof; wherein:
n is an integer from 0 to 18;
X is S or NH;
Z is alkyl, alkenyl, alkynyl, cycloalkyl, aryl, or heterocyclyl, each of which is optionally substituted; and
the group G is either G1 or G2:

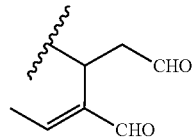

G1

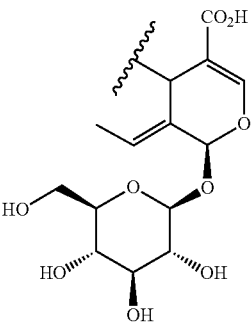

G2

Further embodiments of the invention include compounds selected from the group consisting of:

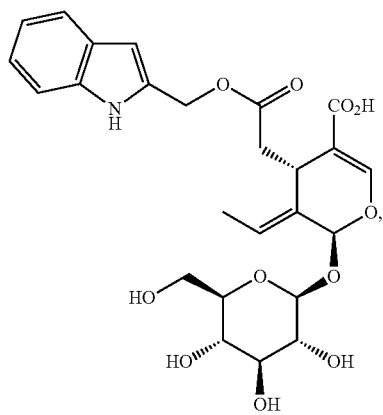

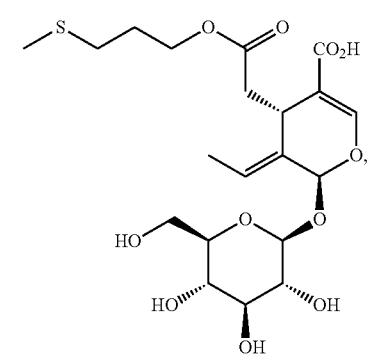

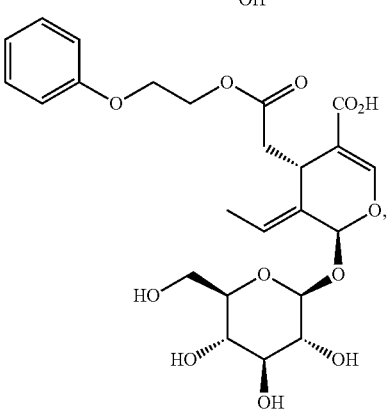

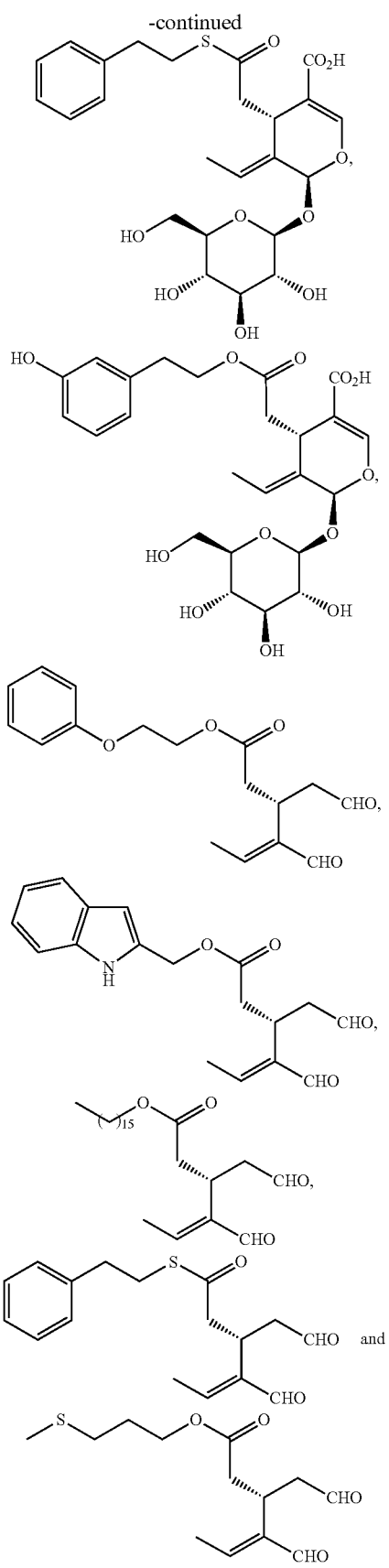

or a pharmaceutically acceptable salt thereof.

In another embodiment, the invention provides a method of treating an inflammatory disorder comprising administering to a subject in need thereof a therapeutically effective amount of a compound of Formula I:

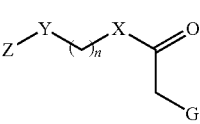

Formula I or a pharmaceutically acceptable salt thereof; wherein:

n is an integer from 0 to 18;

X is O, S, or NH;

Y is CH$_2$, O, S, or NH;

Z is alkyl, alkenyl, alkynyl, cycloalkyl, aryl, or heterocyclyl, each of which is optionally substituted;

the group G is either G1 or G2;

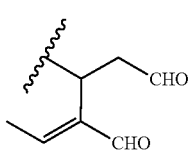

G1

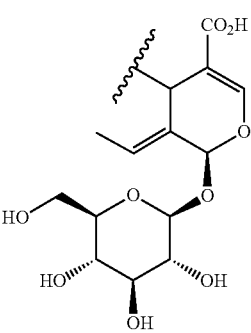

G2 and wherein the compound is not oleacein or oleocanthal.

In another embodiment, the invention provides a method of treating a cardiometabolic disorder comprising administering to a subject in need thereof a therapeutically effective amount of a compound of Formula I:

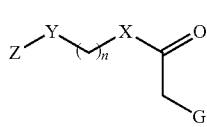

Formula I or a pharmaceutically acceptable salt thereof; wherein:

n is an integer from 0 to 18;

X is O, S, or NH;

Y is CH$_2$, O, S, or NH;

Z is alkyl, alkenyl, alkynyl, cycloalkyl, aryl, or heterocyclyl, each of which is optionally substituted;

the group G is either G1 or G2;

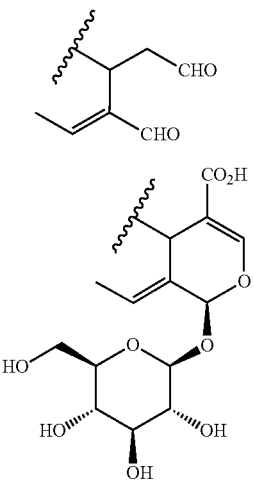

and wherein the compound is not oleacein or oleocanthal.

In another embodiment, the invention provides a method of inhibiting free radical damage in human skin by topical or transdermal administration to a subject in need thereof a therapeutically effective amount of a compound of Formula I:

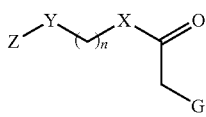

Formula I or a pharmaceutically acceptable salt thereof; wherein:
n is an integer from 0 to 18;
X is O, S, or NH;
Y is $CH_2$, O, S, or NH;
Z is alkyl, alkenyl, alkynyl, cycloalkyl, aryl, or heterocyclyl, each of which is optionally substituted;
the group G is either G1 or G2;

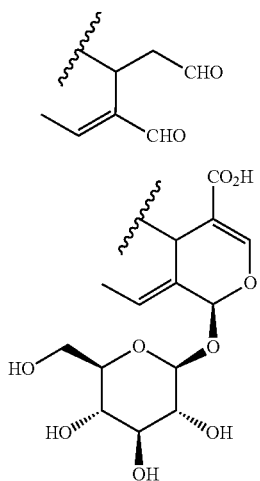

and wherein the compound is not oleacein or oleocanthal.

In yet another embodiment, the invention provides a method of treating cancer comprising administering to a subject in need thereof a therapeutically effective amount of a compound of Formula I:

Formula I or a pharmaceutically acceptable salt thereof; wherein:
n is an integer from 0 to 18;
X is O, S, or NH;
Y is $CH_2$, O, S, or NH;
Z is alkyl, alkenyl, alkynyl, cycloalkyl, aryl, or heterocyclyl, each of which is optionally substituted;
the group G is either G1 or G2;

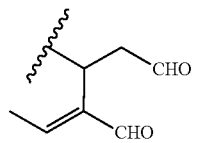

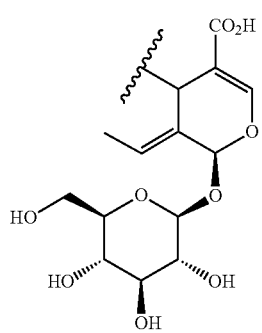

and wherein the compound is not oleacein or oleocanthal.

Embodiments of the invention also provide methods of inhibiting an ATP Citrate Lyase (ACLY)—associated disease comprising administering to a subject in need thereof a therapeutically effective amount of a compound of Formula (I-a):

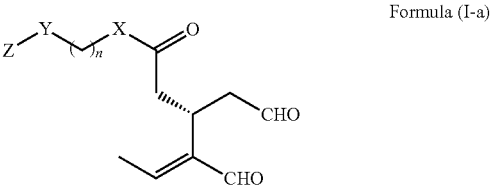

Formula (I-a)

or pharmaceutically acceptable salt thereof; wherein:
n is an integer from 0 to 18;
X is O, S, or NH;
Y is $CH_2$, O, S, or NH; and
Z is alkyl, alkenyl, alkynyl, cycloalkyl, aryl, or heterocyclyl, each of which is optionally substituted.

In yet another embodiment, the present invention provides a method of treating an ATP Citrate Lyase (ACLY)- associated disease comprising administering to a subject in need thereof a therapeutically effective amount of a compound of formula

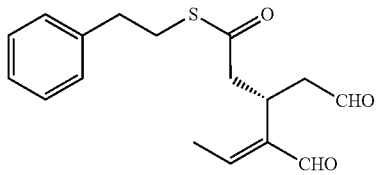 [SMILES: C/C=C(/C=O)[C@@H](CC=O)CC(=O)SCCc1ccccc1]

or pharmaceutically acceptable salt thereof;
wherein the compound has an inhibitory efficacy against the ACLY protein.

Other features and advantages of the present invention are described further in the following description, examples, claims and drawings.

DETAILED DESCRIPTION

1. Compounds and Definitions

Figure 1:
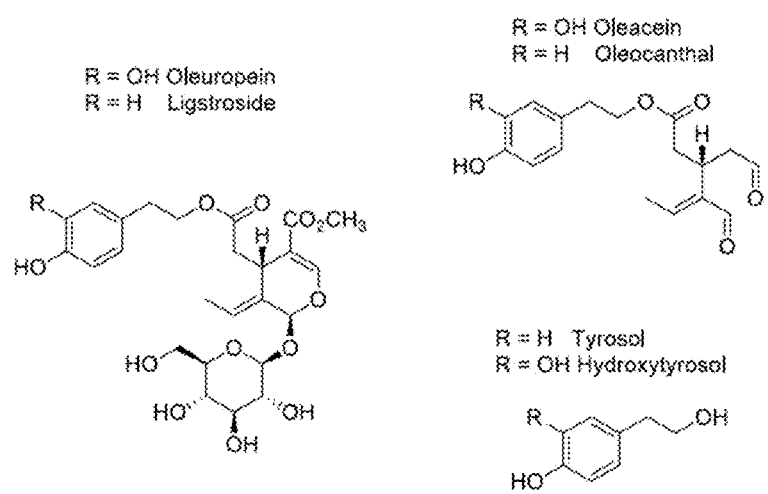
FIG. 1 shows the structures of phenolic compounds in extra virgin olive oil (EVOO).

The present invention provides novel analogues of the natural products oleuropein and oleacein having improved pharmacokinetic properties and more potent biological activity than the natural products. In some embodiments, such compounds include those of the formulas described herein, or a pharmaceutically acceptable salt thereof, wherein each variable is as defined and described herein. The present invention further provides pharmaceutical compositions comprising the inventive compounds and uses thereof.

General schemes for synthesizing the compounds of the invention can be found herein. Unless indicated otherwise, all references herein to the inventive compounds include references to salts, solvates, hydrates and complexes thereof, including polymorphs, stereoisomers, and isotopically labeled versions thereof.

It is believed that one skilled in the art can, based upon the description herein, utilize the present invention to its fullest extent. The following specific embodiments are to be construed as merely illustrative and not limitative of the remainder of the disclosure. All publications, patent applications, patents, and other references mentioned herein are incorporated by reference in their entirety.

Compounds of this invention include those described generally above, and are further illustrated by the classes, subclasses, and species disclosed herein. As used herein, the following definitions shall apply unless otherwise indicated.

When introducing elements of the present invention or the preferred embodiment(s) thereof, the articles "a", "an", "the", and "said" are intended to mean that there are one or more of the elements. The terms "comprising", "including" and "having" are intended to be inclusive and mean that there are additional elements other than the listed elements.

The term "alkyl" refers to a saturated aliphatic hydrocarbon group which may be straight or branched and having from 1 to about 20 carbon atoms in the chain, and all combinations and subcombinations of ranges therein. Preferred alkyl groups may be straight or branched and have from 1 to about 10 carbon atoms in the chain. Branched means that a lower alkyl group having from 1 to about 6 carbons, is attached to a linear alkyl chain. Representative alkyl groups include methyl, ethyl, propyl, i-propyl, butyl, i-butyl, s-butyl, t-butyl, pentyl, hexyl, heptyl, octyl, decyl, docecyl, etc. The alkyl group may optionally be substituted with one or more substituents described below.

The term "lower alkyl" refers to an alkyl group which may be straight or branched and having from 1 to about 6 carbon atoms in the chain. Representative lower alkyl groups are methyl, ethyl, propyl, butyl, isobutyl, and tert-butyl.

The term "cycloalkyl" refers to a cyclic, aliphatic ring system having from about 3 to about 12 carbon atoms in the ring. The ring system may be monocyclic, bicyclic, multicyclic, bridged, fused, etc. Representative examples of monocyclic cycloalkyl groups include propyl, cyclobutyl, cyclopentyl, cyclohexyl, cycloheptyl and the like. The cycloalkyl group may optionally be substituted with one or more substituents described below.

The term "perfluoroalkyl" refers to an alkyl group in which all the hydrogen atoms have been replaced with fluorine atoms. An example of a common perfluoroalkyl group is trifluoromethyl (—$CF_3$).

The term "alkenyl" refers to a branched or straight chain hydrocarbon group having one or more carbon-carbon double bonds. Representative examples of alkenyl groups include ethenyl, 1-propenyl, 2-propenyl, allenyl, 3-butenyl, 4-butenyl and the like. The alkenyl group may optionally be substituted with one or more substituents described below.

The term "alkenyl" refers to a branched or straight chain hydrocarbon group having one or more carbon-carbon triple bonds. Representative examples of alkynyl groups include ethynyl, 1-propynyl, 2-propynyl, 1-butynyl, and the like. The alkynyl group may optionally be substituted with one or more substituents described below.

The term "aryl" refers to a cyclic, aromatic hydrocarbon. Common aryl groups are six to fourteen membered rings. Aryl groups include, for example, phenyl, biphenyl, naphthyl, anthracyl, and the like. A preferred aryl group is phenyl. The aryl group may optionally be substituted with one or more substituents described below.

The term "heteroatom" means one or more of oxygen, sulfur, boron, nitrogen, phosphorus, or silicon (including, any oxidized form of the heteroatom (e.g., pyridine N-oxide) or substituted form of the heteroatom (e.g., N-substituted piperidinyl).

The term "heterocyclyl" refers to a ring system containing one or more rings in which one or more of the atoms in the ring is an element other than carbon (e.g., N, O, S, B, P, Si, etc.). Typically, a heterocyclyl group is a monocyclic or fused ring group having 3 to 14 rings atoms including carbon atoms, containing one, two, three or four rings heteroatoms which may be the same or different. Commonly, a heterocyclyl group will contain 1 to 4 heteroatoms selected from N, O, and S. The heterocyclyl group may optionally be substituted with one or more substituents described below.

Heterocyclyl groups may be aromatic or non-aromatic. The rings in a heterocyclyl groups may be saturated, partially unsaturated, or fully unsaturated. Representative examples of saturated heterocyclyl groups include tetrahydrofuranyl, tetrahydropyranyl, tetrahydrothiophenyl, pyrrolidinyl, piperidinyl, piperazinyl, morpholinyl, and the like. Representative examples of partially unsaturated heterocyclyl groups include dihydrofuranyl, dihydropyrrolyl, tetrahydropyridinyl, tetrahydroindolyl, and the like. Representative examples of fully unsaturated heterocyclyl groups (also called heteroaryl) include, for example, imidazolyl, pyrrolyl, furanyl, thienyl, tetrazolyl, indolyl, benzofuranyl, pyridyl, pyridazinyl, pyrimidinyl, isoquinolinyl, quinolinyl, purinyl, and the like. Examples of fused ring heteroaryl groups include benzofuranyl, benzothiophenyl, indolyl, benzimidazolyl, indazolyl, purinyl, and the like. A preferred heterocyclyl group is indolyl.

It is noted that cyclic ring groups, i.e., cycloalkyl, aryl, heterocyclyl, can comprise more than one ring. For example, the indole group has a bicyclic structure consisting of a six membered benzene ring fused to a five membered pyrrole ring. It is also within the scope of the invention that ring groups can have bridging atoms or a spiro orientation.

The term "unsubstituted" refers to a group having a hydrogen atom as a substituent. The term "substituted" refers to a group wherein one or more hydrogen atoms in the group is replaced with another atom or group.

Typical substituents include, for example, halo (e.g., F, Cl, Br, I), alkyl, alkenyl, alkynyl, aralkyl, aryl, heteroaryl, heterocyclyl, hydroxyl (OH), alkoxyl (OR'), oxo (=O), nitro ($NO_2$), nitrosyl (NO), cyano (CN), cyanato (CNO), thiocyanato (SCN), amino (e.g., $NH_2$, NHR', NR'R"), azido ($N_3$), carboxyl (COOH), C(O)R', C(O)OR', NHC(O)R', aminocarbonyl, thiol (SH), thiolato (SR'), sulfonic acid ($SO_3H$), phosphonic acid ($PO_3H$), $SO_2R'$, phosphino (PH', PHR', PR'R"), silyl, and the like. Each moiety R' can be, independently, any of alkyl, aryl, aralkyl, heteroaryl or heterocyclyl, for example.

The term "compound," as used herein, includes salts, solvates and polymorphs of the compound, as well as the free base. A "solvate" is a stable, solid or semi-solid form of a compound that comprises either a non-stoichiometric or a stoichiometric equivalent of solvent. If the solvent is water, the solvate is a hydrate. In certain embodiments, the hydrate has a stoichiometric equivalent of water chosen from about 0, about 0.5, and about $1H_2O$; that is, the hydrate is anhydrous, a hemihydrate, or a monohydrate. Non-stoichiometric hydrates and stoichiometric hydrates are both contemplated.

The term "pharmaceutically acceptable salt" refers to the relatively non-toxic, inorganic and organic, acid and base addition salts of compounds disclosed herein. The salts can be prepared by reacting a purified compound in its free base or acid form with a suitable organic or inorganic base or acid, and isolating the salt thus formed. Alternatively, the salts can be prepared in situ during the final isolation and purification of the a compound. Representative salts include, for example, those listed in Berge et al., "Pharmaceutical Salts," *J. Pharm Sci, Vol.* 66, pp. 1-19, (1977).

Acid addition salts can be obtained by reaction of the free base of the parent compound with inorganic acids, hydrochloric acid, hydrobromic acid, phosphoric acid, sulfuric acid and perchloric acid and the like, or with organic acids such as acetic acid, oxalic acid, tartaric acid, citric acid, methanesulfonic acid, malonic acid, succinic acid, salicylic acid and the like. Salts derived from appropriate bases include alkali metal salts, alkaline earth metal salt, ammonium salts, and quaternary ammonium salts.

Certain acidic or basic compounds may exist as zwitterions. All forms of the compounds, including free acid, free base, and zwitterions, are contemplated to be within the scope of the present invention.

The term "prodrug" refers to a derivative of a compound which may have little or no biological activity but, when administered to a patient, can be converted into a biologically active compound. Prodrugs of the inventive compounds are within the scope of the invention.

Compound of the present invention may exist in various solid states including crystalline states and an amorphous state. The term "polymorph" refers to a distinct crystalline form of a compound. A compound may be, for example, a polymorph of a free base, a polymorph of a salt, a polymorph of a hydrate, or a polymorph of a hydrate of a salt of a compound, and so forth. The different crystalline states and the amorphous state of the present compounds are contemplated as part of the invention. Compounds of the invention intended for pharmaceutical use may be administered as crystalline or amorphous solids or mixtures thereof.

Compounds of the present invention containing one or more asymmetric or chiral centers can exist as two or more stereoisomers. When the compounds according to the invention have at least one chiral center, they may exist as enantiomers. When the compounds possess two or more chiral centers, they may additionally exist as diastereomers. When the compound possesses a double bond, geometric cis/trans (or Z/E) isomers are possible. When the compound contains, for example, a keto or oxime group or an aromatic group, tautomeric isomerism may occur. Included within the scope of the invention are all stereoisomers, geometric isomers, and tautomeric forms of the inventive compounds, including compounds exhibiting more than one type of isomerism, and mixtures thereof.

In certain embodiments, the present invention is directed to a single stereoisomer of a compound represented by any of the structures described herein.

Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art.

The present invention also includes isotopically-labelled compounds which are identical to the those disclosed herein but for the fact that one or more atoms are replaced by an isotope. An "isotope" is a variant of a particular element which differs in number of neutrons in the nucleus, and consequently in atomic mass, from that usually found in nature. Examples of isotopes that can be incorporated into compounds of the present invention include isotopes of hydrogen (e.g., $^2H$, $^3H$); carbon (e.g., $^{11}C$, $^{13}C$, $^{14}C$), nitrogen (e.g., $^{15}N$); oxygen (e.g., $^{15}O$, $^{17}O$, $^{18}O$); phosphorus (e.g., $^{32}P$); sulfur ($^{35}S$); fluorine (e.g., $^{18}F$); chlorine (e.g., $^{36}Cl$); and iodine (e.g., $^{123}I$ and $^{125}I$).

An isotope labeled-compound of the present invention can be used in a number of beneficial ways. For example, an isotope-labeled compound of Formula I into which a radioisotope such as $^3H$ or $^{14}C$ has been incorporated is suitable for substrate tissue distribution assays. Incorporation of heavier isotopes such as $^2H$ into a compound of Formula I has therapeutic advantages due to the higher metabolic stability of this isotope-labeled compound. Higher metabolic stability can translate into an increased in vivo half-life or lower dosages, which under most circumstances would represent an preferred embodiment of the present invention.

Substitution with positron emitting isotopes such as $^{11}C$, $^{13}N$, $^{15}O$ and $^{18}F$ can be useful in positron emission topography (PET) studies.

Isotopically-labeled compounds of the invention can generally be prepared by conventional techniques known to those skill in the art or by processes described herein, using an appropriate isotopically-labeled reagent in place of the non-labeled reagent otherwise employed.

In some embodiments, the present invention provides compounds of Formula (I):

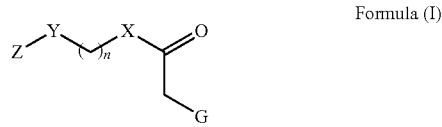

Formula (I)

or a pharmaceutically acceptable salt thereof; wherein:

n is an integer from 0 to 18;

X is O, S, or NH;

Y is $CH_2$, O, S, or NH;

Z is alkyl, alkenyl, alkynyl, cycloalkyl, aryl, or heterocyclyl, each of which is optionally substituted; and the group G is either G1 or G2:

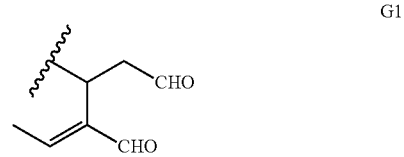

G1

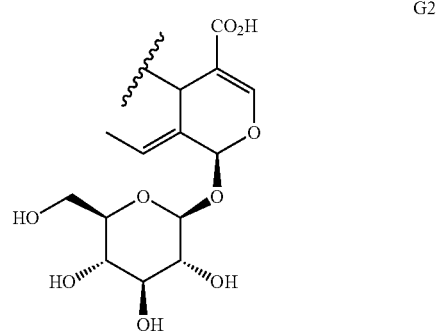

G2

In certain embodiments, if X=O and n=0, then Y=$CH_2$ and Z=aryl, substituted aryl, heteroaryl, or substituted heteroaryl. In certain embodiments, if X=O, n=1 and Y=$CH_2$, then Z is not cyclohexyl, phenyl, or substituted phenyl. In certain embodiments, the compound of Formula (I) is not (2S,3E,4S)-2H-pyran-4-acetic acid, 5-carboxy-3-ethylidene-2-(β-D-glucopyranosyloxy)-3,4-dihydro-4-hexadecyl ester or (3S,4E)-4-hexenoic acid, 4-formyl-3-(2-oxoethyl)-, pentyl ester.

In an embodiment, the invention provide compounds of Formula (I-a) or a pharmaceutically acceptable salt thereof, wherein the group G in Formula (I) is G1:

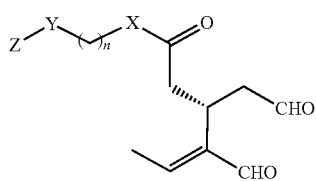

Formula (I-a)

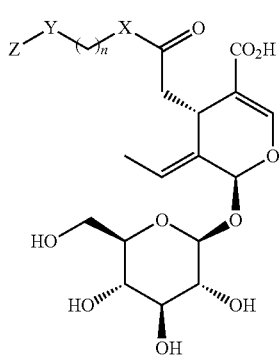

Formula (I-b)

In a preferred embodiment, a compound of Formula (I-a) is selected from the group consisting of:

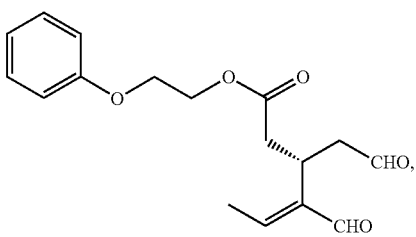

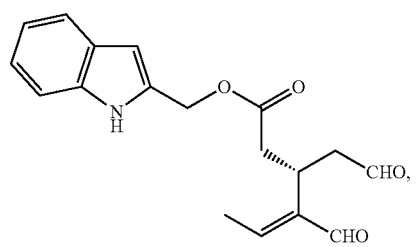

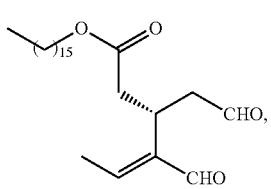

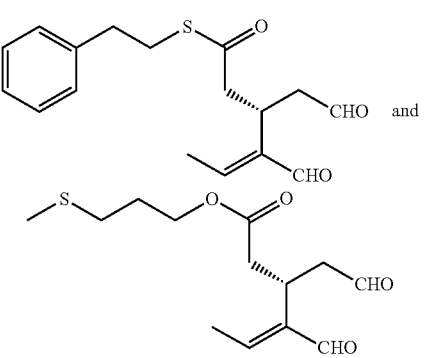

or a pharmaceutically acceptable salt thereof.

In an embodiment, the invention provides compounds of Formula (I-b) or a pharmaceutically acceptable salt thereof, wherein the group G in Formula (I) is G2:

In a preferred embodiment, a compound of Formula (I-b) is selected from the group consisting of:

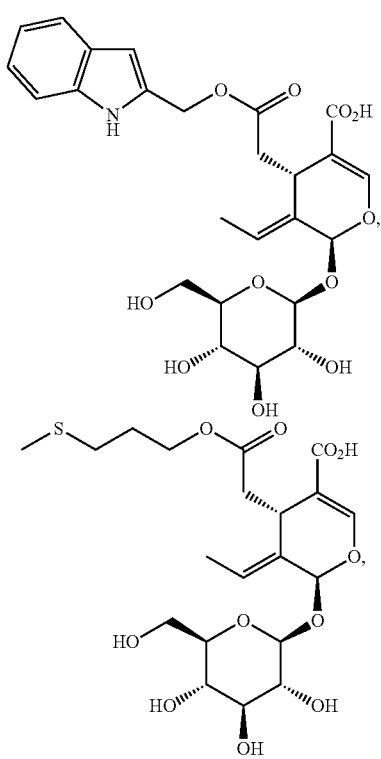

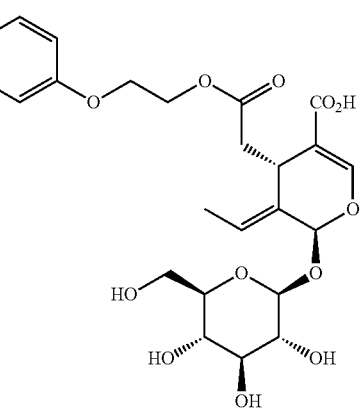

and

-continued

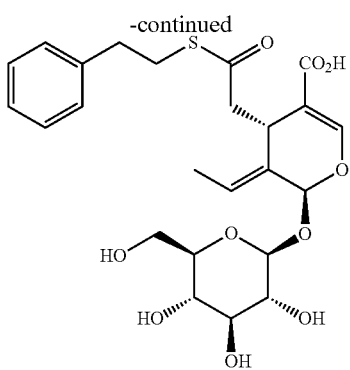

or a pharmaceutically acceptable salt thereof.

In certain embodiments, the invention further includes compounds of Formula (II):

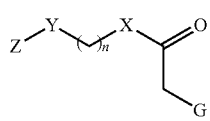

Formula (II)

or a pharmaceutically acceptable salt thereof; wherein:
n is an integer from 1 to 18;
X is O, S, or NH;
Y is O, S, or NH;
Z is alkyl, alkenyl, alkynyl, cycloalkyl, aryl, or heterocyclyl, each of which is optionally substituted; and
the group G is either G1 or G2:

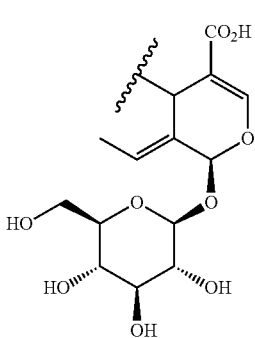

G1

G2

In another embodiment, the invention further includes compounds of Formula (III):

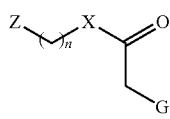

Formula (III)

or a pharmaceutically acceptable salt thereof; wherein:
n is an integer from 0 to 18;
X is S or NH;
Z is alkyl, alkenyl, alkynyl, cycloalkyl, aryl, or heterocyclyl, each of which is optionally substituted; and
the group G is either G1 or G2:

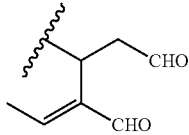

G1

G2

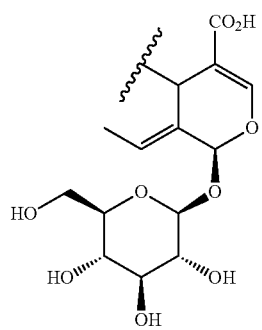

Moreover, embodiments of the invention include compounds selected from the group consisting of:

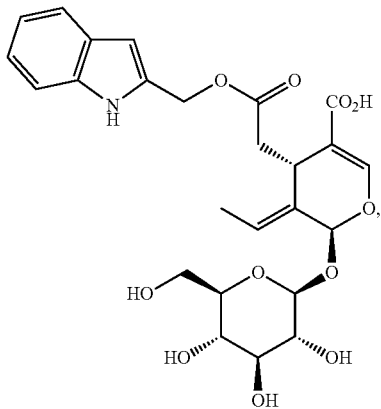

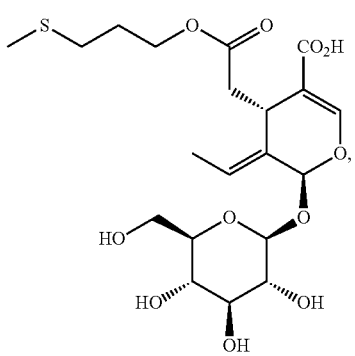

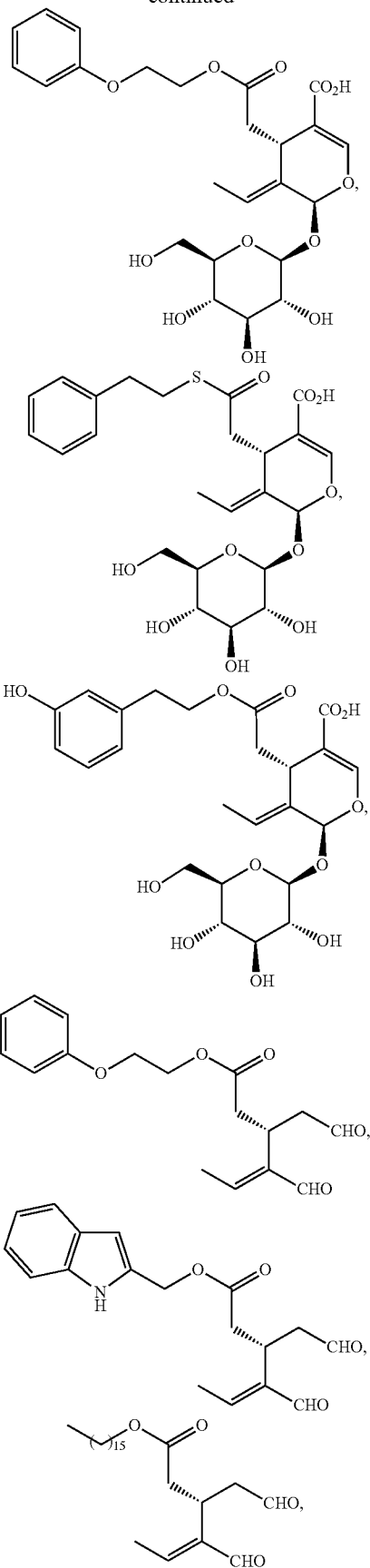

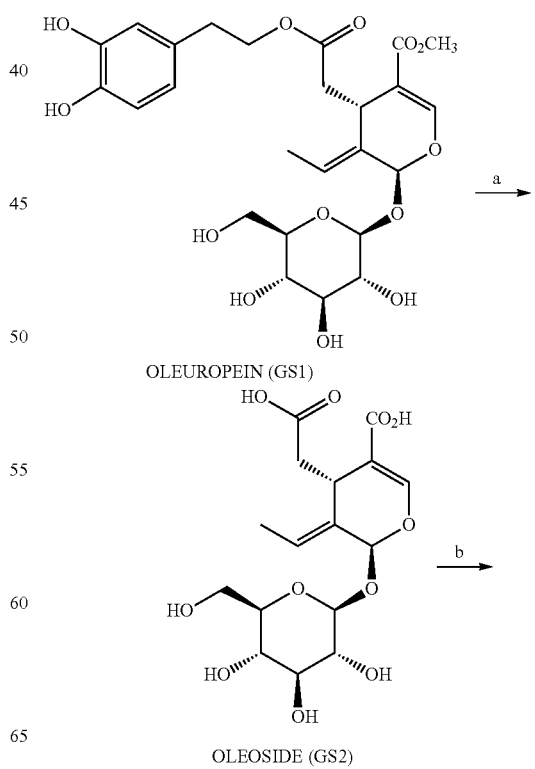

or a pharmaceutically acceptable salt thereof.

2. Preparation of Compounds of Formula I and Related Formulas

Compounds of the present invention as defined in the embodiments disclosed herein can be synthesized by synthetic routes that includes processes well known in the chemical art. In addition, many of the exemplary compounds can be further modified in light of this disclosure using conventional chemistry well known to those skilled I the art.

In some embodiments, the compounds of this invention are prepared according to the general synthetic scheme shown in Scheme I below.

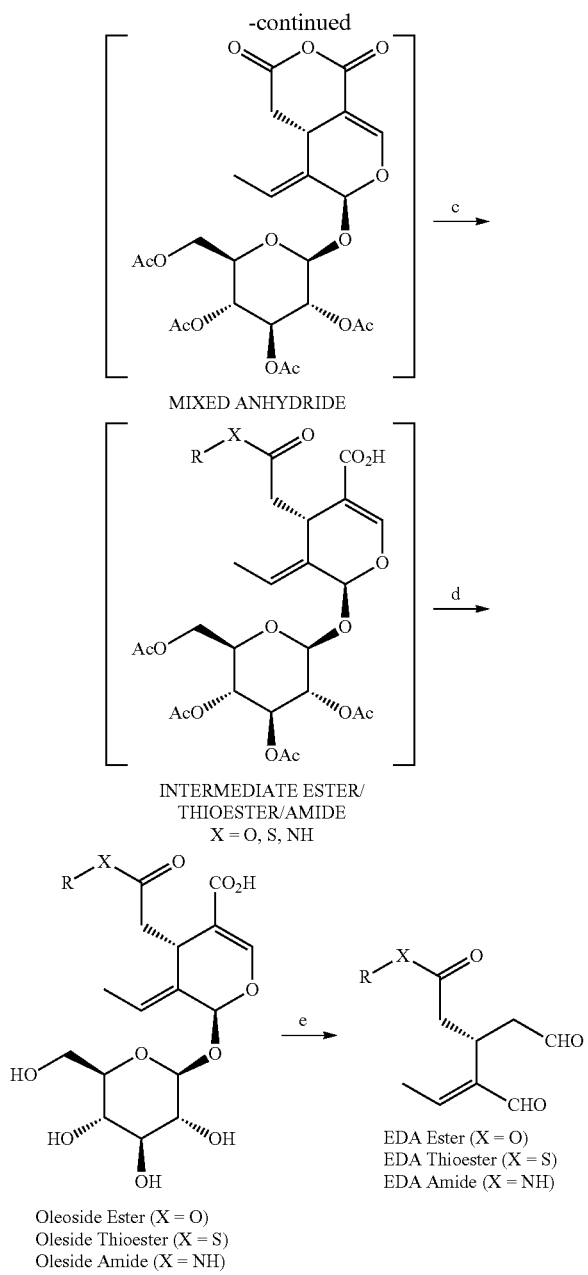

MIXED ANHYDRIDE

INTERMEDIATE ESTER/
THIOESTER/AMIDE
X = O, S, NH

Oleoside Ester (X = O)
Oleside Thioester (X = S)
Oleside Amide (X = NH)

EDA Ester (X = O)
EDA Thioester (X = S)
EDA Amide (X = NH)

As shown in Scheme I, the compounds of the present invention can be prepared from oleuropein (GS1), which is obtained via extraction of acetone leaves. In step (a), oleuropein can be saponified in the presence of base, such as aqueous sodium hydroxide, at room temperature to form oleoside (GS2). Oleoside can be prepared in large amounts (e.g., tens of grams scale) and provides a useful synthetic intermediate.

In step (b), oleoside can be converted to a mixed anhydride by treatment with reagents such as acetic anhydride in the presence of pyridine at room temperature. The mixed anhydride so obtained can be reacted with a suitable alcohol and coupling reagent in step (c) to give an intermediate ester (X=O) bearing an acetylated sugar group. Similarly, by reaction of the mixed anhydride with a suitable thiol or amine, an intermediate thioester (X=S) or thioamide (X=NH) can be obtained. The acetate groups on the sugar can be removed in step (d) using a deprotecting agent such as hydrazine or diethylamine. In this way, a wide variety of oleoside esters, thioesters, and amides can be conveniently prepared in four steps from oleuropein. Optionally, the overall transformation of oleoside to the corresponding ester, thioester or amide can be achieved without purification of the intermediate mixed anhydride or intermediate ester/thioester/amide.

The present invention further encompasses transformation of the oleoside ester, thioester, and amide to the corresponding dialdehyde in step (e). This can be achieved, for example, via incubation with β-glucosidase in acetic acid/sodium acetate buffer (pH 5) at a temperature of 37° C. Without being bound by theory, it is believed that the mechanism of step (e) involves hydrolysis of the sugar group followed by spontaneous decarboxylation.

For convenience, the dialdehydes prepared in accordance with Scheme I may be referred to as EDA aldehydes, as is common in the literature. Elenolic acid dialdehyde has the structure shown below.

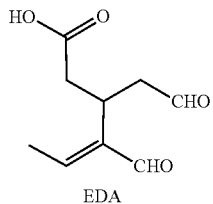

EDA

The starting materials, chemical intermediates and final products of the reaction may be isolated and purified if desired using conventional techniques, including but not limited to filtration, multiphase extraction, distillation, crystallization, chromatography and the like. Chromatography can involve any number of methods including, for example, normal phase and reverse phase chromatography; size exclusion chromatography; ion exchange chromatography; high, medium and low phase liquid chromatography; preparative thin or thick layer chromatography; as well as techniques of thin layer and flash chromatography. Such materials, intermediates and products may be characterized using conventional means, including physical constants and spectral data.

Diastereomeric mixtures can be separated into their individual diastereomers on the basis of their physical differences by methods well known to those skilled in the art, such as fractional crystallization and/or chromatography. Enantiomers can be separated by converting the racemic mixture into a diastereomeric mixture, separating the diastereomers and converting the individual diastereomers to the corresponding pure enantiomers. For example, racemic mixtures can be separated and isolated by formation of ionic, diastereomeric salts with chiral compounds and separation by fractional crystallization or other methods; formation of diastereomeric compounds with chiral auxiliaries, separation of the diastereomers and conversion to the pure stereoisomers. Racemic mixtures can also be separated by chromatography using a chiral stationary phase. Enriched or purified enantiomers can be characterized by methods used to distinguish other chiral molecules, such as circular dichroism and optical rotation.

The structures of various compounds prepared according to Scheme I from the starting material oleuropein (GS1) are shown in Table 1. Some of these GS compounds have been previously synthesized but, to our knowledge, their biological activity has not been examined (See, Sarikaki, Georgia et al., J Nat Prod, 2020, 83: 1735-1739).

TABLE 1

Structure of GS Compounds

| Compound No. | Common Name | Chemical Structure |
|---|---|---|
| GS1 | Oleuropein | 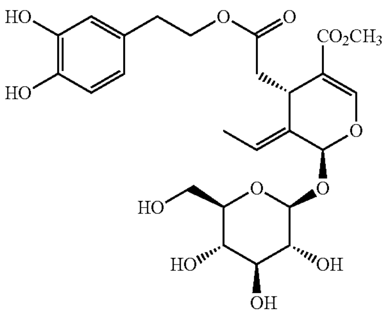 [SMILES: C/C=C1/[C@H](O[C@@H]2O[C@H](CO)[C@@H](O)[C@H](O)[C@H]2O)OC=C(C(=O)OC)[C@H]1CC(=O)OCCc1ccc(O)c(O)c1] |
| GS2 | Oleoside | 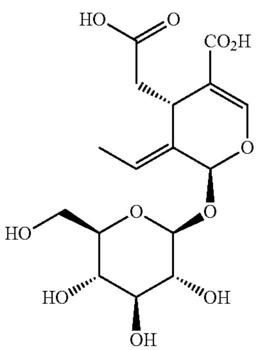 [SMILES: C/C=C1/[C@H](O[C@@H]2O[C@H](CO)[C@@H](O)[C@H](O)[C@H]2O)OC=C(C(=O)O)[C@H]1CC(=O)O] |
| GS3 | | 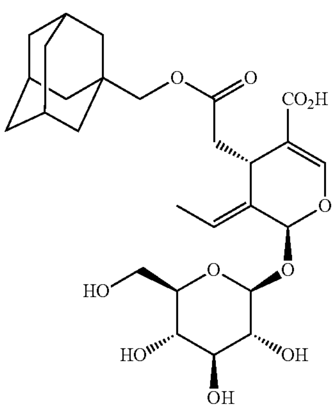 [SMILES: C/C=C1/[C@H](O[C@@H]2O[C@H](CO)[C@@H](O)[C@H](O)[C@H]2O)OC=C(C(=O)O)[C@H]1CC(=O)OCC12CC3CC(CC(C3)C1)C2] |
| GS4 | | 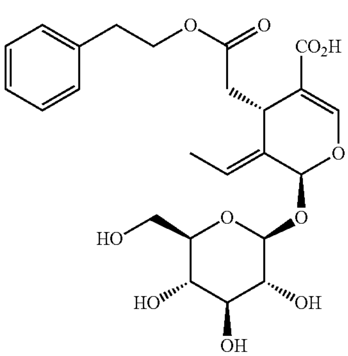 [SMILES: C/C=C1/[C@H](O[C@@H]2O[C@H](CO)[C@@H](O)[C@H](O)[C@H]2O)OC=C(C(=O)O)[C@H]1CC(=O)OCCc1ccccc1] |
| GS5 | | |
| GS6 | Demethyl-oleuropein | |
| GS7 | Demethyl-ligstroside | |
| GS8 | | |

TABLE 1-continued

Structure of GS Compounds

| Compound No. | Common Name | Chemical Structure |
|---|---|---|
| GS9 | | 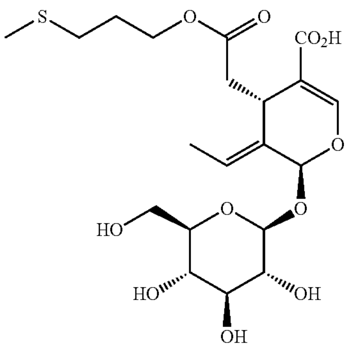 [SMILES: C/C=C1/[C@H](O[C@@H]2O[C@H](CO)[C@@H](O)[C@H](O)[C@H]2O)OC=C(C(=O)O)[C@H]1CC(=O)OCCCSC] |
| GS10 | | 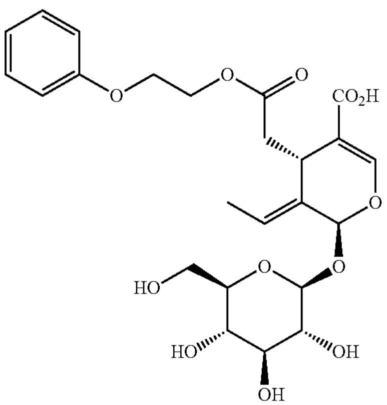 [SMILES: C/C=C1/[C@H](O[C@@H]2O[C@H](CO)[C@@H](O)[C@H](O)[C@H]2O)OC=C(C(=O)O)[C@H]1CC(=O)OCCOc1ccccc1] |
| GS11 | | 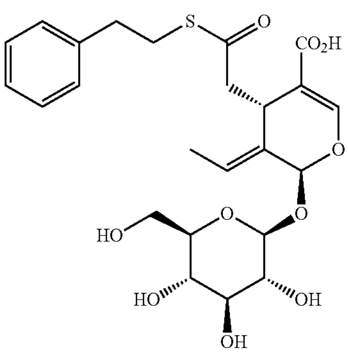 [SMILES: C/C=C1/[C@H](O[C@@H]2O[C@H](CO)[C@@H](O)[C@H](O)[C@H]2O)OC=C(C(=O)O)[C@H]1CC(=O)SCCc1ccccc1] |
| GS14 | | 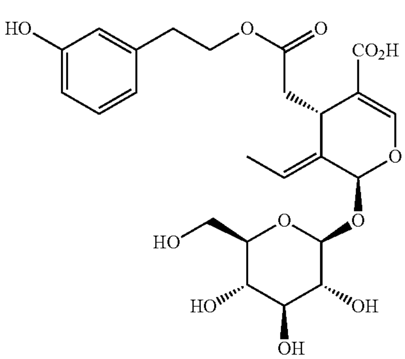 [SMILES: C/C=C1/[C@H](O[C@@H]2O[C@H](CO)[C@@H](O)[C@H](O)[C@H]2O)OC=C(C(=O)O)[C@H]1CC(=O)OCCc1cccc(O)c1] |
| GS15 | | 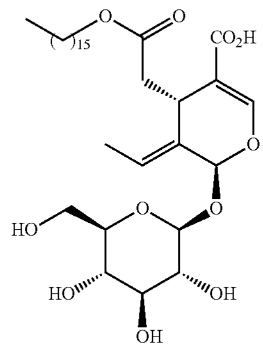 |
| GS16 | | 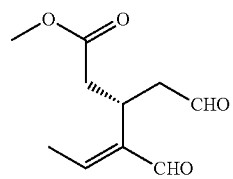 |
| GS17 | Oleacein | 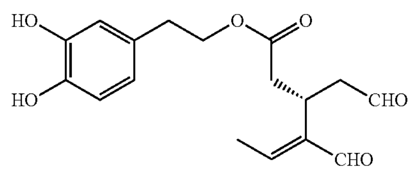 [SMILES: C/C=C(/C=O)[C@@H](CC=O)CC(=O)OCCc1ccc(O)c(O)c1] |
| GS19 | Oleocanthal | 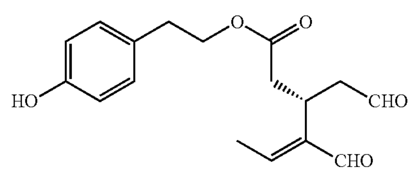 [SMILES: C/C=C(/C=O)[C@@H](CC=O)CC(=O)OCCc1ccc(O)cc1] |
| GS20 | | 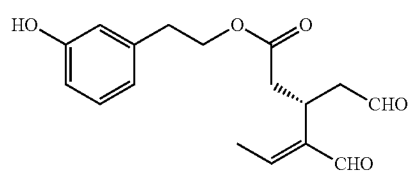 [SMILES: C/C=C(/C=O)[C@@H](CC=O)CC(=O)OCCc1cccc(O)c1] |
| GS21 | | 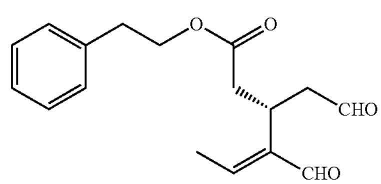 |
| GS22 | | 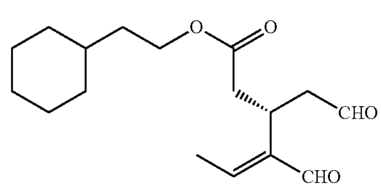 [SMILES: C/C=C(/C=O)[C@@H](CC=O)CC(=O)OCCC1CCCCC1] |

TABLE 1-continued

Structure of GS Compounds

| Compound No. | Common Name | Chemical Structure |
|---|---|---|
| GS23 | | (adamantyl-CH2-O-C(=O)-CH2-CH(CH2CHO)-C(=CHCH3)-CHO) |
| GS24 | | (PhO-CH2CH2-O-C(=O)-CH2-CH(CH2CHO)-C(=CHCH3)-CHO) |
| GS25 | | (indol-2-yl-CH2-O-C(=O)-CH2-CH(CH2CHO)-C(=CHCH3)-CHO) |
| GS26 | | (CH3-(CH2)15-O-C(=O)-CH2-CH(CH2CHO)-C(=CHCH3)-CHO) |
| GS27 | | (Ph-CH2CH2-S-C(=O)-CH2-CH(CH2CHO)-C(=CHCH3)-CHO) |
| GS28 | | (CH3-S-CH2CH2CH2-O-C(=O)-CH2-CH(CH2CHO)-C(=CHCH3)-CHO) |

3. Formulation and Administration of Compounds of Formulas I and Related Formulas The compounds of the present invention can be administered alone or in combination with one or more active agents. Generally, they will be administered as a formulation in association with one or more pharmaceutically acceptable excipients, carrier or vehicle.

The terms "active agent", "active pharmaceutical ingredient", and "therapeutic agent" are used interchangeably herein and include any compound, drug, active composition of matter or mixture which provides a pharmacologic effect that can be demonstrated in-vivo or in-vitro.

The term "excipient" or "inactive ingredient" as used herein means any component of a formulation or pharmaceutical composition other than an active ingredient. A pharmaceutically acceptable excipient refers to an inert substance added to a pharmaceutical composition to further facilitate administration of a compound. Examples of pharmaceutically acceptable excipients include, without limitation, starch, cellulose derivatives, various sugars, vegetable oils, polyethylene glycols, calcium phosphate, talc, silica, magnesium stearate, and the like.

The compounds of the present invention are administered to a subject in a therapeutically effective amount. The compounds can be administered alone or as part of a pharmaceutically acceptable formulation. The compounds or compositions can be administered all at once (e.g., oral administration of a tablet or bolus injection) or delivered over a period of time (e.g. by i.v. infusion). It is also contemplated in the present invention that the dose of the compound can be varied over time.

The terms "subject" and "patient" are used interchangeably herein and refer to a vertebrate, preferably a mammal. In some embodiments, a subject is a human. Human subjects include both children (ages 3 months to 18 years) and adults (18 years and older).

The term "pharmaceutically acceptable" refers to those compounds, materials, compositions, and/or dosage forms which are, within the scope of sound medical judgement, suitable for use in contact with the tissues of human beings and animals without excessive toxicity, irritation, allergic response or other problem or complication, commensurate with a reasonable benefit/risk ratio.

The term "therapeutically effective amount" as used herein means the amount of a compound or composition comprising a compound of the present invention that ameliorates, attenuates, or eliminates one or more symptoms of a particular disease or conditions, or prevents or delays the onset of one or more symptoms of a particular disease or condition.

A "therapeutically effective amount" will vary from subject to subject, the severity of the condition being treated, the particular drug form or combination of drugs employed, mode of administration, and the like. An appropriate "effective" amount in any individual case can be determined by one of ordinary skill in the art using routine experimentation based upon the information provided herein.

The term "treating" as used herein includes achieving a therapeutic benefit. By therapeutic benefit is meant eradication, amelioration, or prevention. Reference to "treating" or "treatment" of a subject is intended to include prophylaxis.

The invention also includes pharmaceutical compositions comprising one or more of the inventive compounds according to any of the previous embodiments along with a pharmaceutically acceptable excipient, carrier, or vehicle. Pharmaceutical compositions suitable for the delivery of compounds of the invention and methods for their preparation will be readily apparent to those skilled in the art. Such compositions and methods for their preparation can be found, for example, in Remington: The Science and Practice of Pharmacy, $22^{nd}$ Edition, (Pharmaceutical Press; 2013), and Aulton's Pharmaceutics, The Design and Manufacture of Medicines, $5^{th}$ Edition (Elsevier; 2018), the disclosures of which are incorporated by reference.

The compositions of the invention can be formulated so as to provide immediate-, sustained- or delayed-release of the active ingredient after administration to the patient by employing procedures known in the art.

Exemplary compositions include, but not limited to, tablets, capsules, pills, powders, wafers, lozenges, chewing gum, lollipop, sachets, solutions, syrups, slurries, suspensions, emulsions, aerosols, sprays, ointments, suppositories, gels, creams, patches, and the like. Compositions for use in accordance with the present invention may be formulated in a conventional manner using one or more pharmaceutically acceptable excipients comprising carriers, diluents, and auxiliaries which facilitate processing of the active compound into a preparation which can be used physiologically. The composition is dependent upon the route of administration chosen.

Any suitable method for administering a drug or treatment to a subject can be used. For example, the compounds of the present invention and other active agents can be administered to a subject orally, parenterally (e.g., intravenously, intramuscularly or subcutaneously), topically, and rectally.

In some embodiments, administering a drug to a subject comprises self-administration, administration to the subject by a non-medical professional, or administration to the subject by a medical professional. A suitable formulation and/or route of administration can be chosen by a medical professional (e.g., a physician) in view of, for example, a subject's disease, condition, symptoms, weight, age, and/or general health.

Oral Administration

In certain embodiments, the compounds of the present invention are administered orally. Solid formulations suitable for oral administration include, but are not limited to, tablets, capsules, pills, powers, wafers, lozenges, lollipops, chewing gum, and the like. Solid formulations for oral administration may be formulated to be immediate and/or modified release. Modified release formulations include delayed-, sustained-, controlled-, pulsed- and targeted-release. Also contemplated with the scope of the invention are fast dissolving oral films, which disintegrate or dissolve within 1 minute when placed in the mouth without drinking water or chewing.

Liquid formulations suitable for oral administration include, but are not limited to, sprays, suspensions, emulsions, solutions, syrups, and elixirs. Liquid formulations may be prepared by reconstitution of a solid, for example, from a sachet. Liquid formulations may also be used as fillers in hard or soft capsules.

In the case of tablets for oral use, the excipients may be, for example, inert diluents, such as dicalcium phosphate, calcium sulfate, mannitol and lactose; binders such as corn starch, gelatin, hydroxypropyl methylcellulose (HMPC) and polyvinylpyrrolidone; disintegrants such as croscarmellose, crospovidone, and sodium starch glycolate; lubricating agents such as magnesium stearate, stearic acid and talc; and glidants such as colloidal silicon dioxide. Tablets may be uncoated or may be coated by known techniques including microencapsulation to delay disintegration and adsorption in the gastrointestinal tract and thereby provide a sustained action over a longer period. For oral administration in a capsule form, useful diluents include fillers such as lactose, binders such as starches, lubricants such as talc or magnesium stearate and optionally, stabilizers. When aqueous suspensions are required for oral use, the active ingredient is typically combined with emulsifying and suspending agents. If desired, certain sweetening, flavoring or coloring agents may also be added.

Parenteral Administration

In certain embodiments, the compounds of the invention are administered parenterally. Parenteral administration includes, for example, intradermal, intravenous, subcutaneous, intramuscular, intrathecal, intra-arterial, intraperitoneal, intracranial, intra-articular, intracardiac, intracavernous, intralesion, intraosseous, intrauterine, intravaginal, intravesical, intravitreal, and the like. Devices for parenteral administration include needle injectors, needle free injectors, and infusion techniques.

Sterile injectable forms of the compositions of this invention may be aqueous or oil-based suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol or glycerol. Among the acceptable vehicles and solvents that may be employed are water, aqueous dextrose, Ringer's solution and isotonic sodium chloride solution. In addition, for oil-based suspensions, fatty oils such as sesame or castor oil or fatty acids esters such as ethyl oleate, triglycerides or liposomes are conventionally employed as a solvent or suspending medium.

Topical and Transdermal Administration

The compounds of the present invention may also be administered topically or transdermally to the skin or mucosa.

Compositions suitable for topical or transdermal administration include, but are not limited to, solutions, sprays, powders, gels, lotions, creams, ointments, pastes, films, patches, adhesive bandages, wipes, suppositories, tinctures, and the like. More recent approaches include the use of aerosol foams, microsponges, muco-adhesive bioadhesives, nanoemulsions, etc. Such compositions and methods for their preparation can be found, for example, in Sharadha M., et al. Int J Res Pharm Sci, 2020, 11(1): 368-385, the disclosure of which is incorporated by reference.

In certain embodiments, the invention includes pharmaceutical compositions comprising one or more of the inventive compounds according to any of the previous embodiments and an excipient, carrier or vehicle suitable for topical or transdermal administration. Such compositions are physiologically tolerable and do not typically produce an allergic or similar untoward reaction when applied to human skin. Accordingly, the excipients, carrier or vehicle are suitable for use in contact with human skin without undue toxicity, incompatibility, irritation, allergic response, and the like.

The topical compositions of the invention may be optionally combined with other ingredients such as moisturizers, anti-oxidants, anti-acne agent, depigmenting agents, anti-aging agents, sunscreens, bleaching agents, conditioners, foaming agents, humectants, fragrances, colorants, viscosifiers, buffering agents, surfactants, preservatives and the like.

In an embodiment, the topical compositions for use in the methods of the present invention may be applied up to four times daily for a period of up to about twelve weeks, preferably from about four to about eight weeks, and more preferably for up to 4 weeks. In certain embodiments, application of the topical composition is on a continuous, regular daily basis. Application may be continued as long as desired to maintain the condition of the skin, treat a condition associated with free radical damage, reduce the risk of free radical damage to the skin, or to reduce the risk of skin cancer.

The topically applied composition should be applied in an amount effective to achieve the desired changes in the skin. In one embodiment, the topical composition is applied to the skin surface such that, based upon a cm² of skin surface, from about 2 µL/cm² to about 500 µL/cm² of topically active agent is present.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Rectal Administration

Topical application for the lower intestinal tract can be in a effected in a rectal suppository formulation. Suppositories can be prepared by mixing the active agent with a suitable non-irritating excipient that is solid at room temperature but liquid at rectal temperature and therefore will melt in the rectum to release the drug. Such materials include cocoa butter, beeswax and polyethylene glycols. Topical application for the lower intestinal tract may also be effected in a suitable enema formulation.

Dosage

The compositions are preferably formulated in a unit dosage form for administration to a subject, each dosage containing from about 1 to about 2000 mg. In certain embodiments, the unit dosage form contains one or more of the inventive compounds in an amount of about 1, 5, 10, 20, 25, 50, 75, 100, 125, 200, 250, 300, 350, 400, 450, 500, 550, 600, 650, 700, 750, 800, 850, 900, 950 or 1,000 mg.

The term "unit dosage forms" refers to physically discrete units suitable as unitary dosages for human subjects and other mammals, each unit containing a predetermined quantity of active ingredient calculated to produce the desired therapeutic effect in association with a suitable pharmaceutical excipient. Preferably, the pharmaceutical composition comprises less than 20 wt. % of a compound of Formula I or related Formulas, more preferably it comprises less than 10 wt. % of a compound of Formula I or related Formulas, with the balance being inert ingredients.

In certain embodiments, a therapeutically effective amount of a composition disclosed herein comprises one or more doses administered to a subject, each comprising at least 0.01 mg, at least 0.1 mg, at least 5 mg, at least 10 mg, at least 15 mg, at least 20 mg, at least 25 mg, at least 50 mg, at least 100 mg, at least 250 mg, at least 500 mg, at least 1000 mg, at least 5000 mg, or at least 7000 mg of the active ingredient. For an adult human having a body weight of about 70 kg, a therapeutically effective dosage is typically in the range of about 0.01 mg/kg to about 300 mg/kg body weight, preferably about 0.01 mg/kg to about 35 mg/kg per day, in single or divided doses. For a 70 kg human, this would amount to about 0.07 to about 7000 mg/day, preferably about 0.7 to about 2500 mg/day.

The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

Combination Therapy

The compounds of the present invention can also be administered in combination with other pharmaceutically active agents. The other pharmaceutically active agent can be intended to treat the same disease, disorder or condition as the compounds of the present invention or a different disease, disorder or condition. It is noted that the term "active agent" can include biologics, such as antibodies against cytokines and interferon proteins, and vaccines. If a subject is to receive multiple pharmaceutically active agents, the active agents can be administered simultaneously (e.g., in one tablet) or sequentially (e.g., in separate tablets). All combinations, delivery methods, and administration sequences are contemplated in the present invention.

Kits

The invention further relates to combining two separate pharmaceutical compositions in kit form. The kit can comprise, for example, a compound of the instant invention and a second active agent. Representative examples of kits include a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing medical professional.

4. Methods of Use

The compounds of the present invention are therapeutically useful because of their antioxidant, anti-inflammatory, and/or anti-cancer properties.

Embodiments of the present invention include methods of treating an inflammatory disorder comprising administering to a subject in need thereof a therapeutically effective amount of a compound of Formula I or related Formulas described herein, or a pharmaceutically acceptable salt thereof, alone or in combination with one or more pharmaceutically acceptable excipient, carrier or vehicle.

In one embodiment, the invention provides a method of treating an inflammatory disorder comprising administering to a subject in need thereof a therapeutically effective amount of a compound of Formula I:

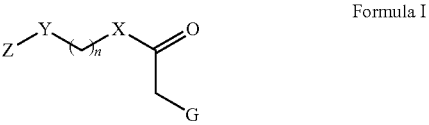

Formula I or a pharmaceutically acceptable salt thereof; wherein
n is an integer from 0 to 18;
X is O, S, or NH;
Y is $CH_2$, O, S, or NH;
Z is alkyl, alkenyl, alkynyl, cycloalkyl, aryl, or heterocyclyl, each of which is optionally substituted;
the group G is either G1 or G2;

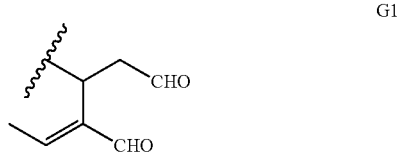

G1

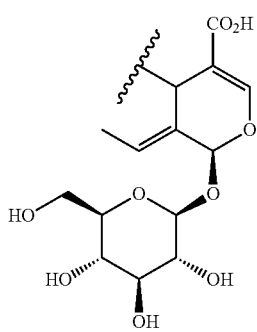

and wherein the compound is not oleacein or oleocanthal.

The term "inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

In certain embodiments, the inflammatory disorder is a gastrointestinal inflammatory disorder selected from the group consisting of ulcerative colitis, Crohn's disease, celial disease, primary sclerosing cholangitis, primary biliary cirrhosis, autoimmune hepatitis, eosinophilic esophagitis and Mooren's ulcer.

In certain embodiments, the inflammatory disorder is an autoimmune inflammatory disorder selected from the group consisting of systemic lupus erythematosus, psoriasis, rheumatoid arthritis, Type 1 diabetes, multiple sclerosis, Sjogren syndrome, atopic dermatitis, Behcet's Disease and Familial Mediterranean Fever.

In certain embodiments, the inflammatory disorder is a viral inflammatory disorder which is influenza virus infection or SARS-CoV2 infection.

In certain embodiments, the inflammatory disorder is a cardiovascular inflammatory disorder selected from the group consisting of coronary artery disease, atherosclerosis, hypercholesterolemia and hypertriglyceridemia.

Additional embodiments of the present invention include methods of treating a cardiometabolic disorder comprising administering to a subject in need thereof a therapeutically effective amount of a compound of Formula I or related Formulas described herein, or a pharmaceutically acceptable salt thereof, alone or in combination with one or more pharmaceutically acceptable excipient, carrier or vehicle. As used herein, the terms "cardiometabolic disorder" and "cardiometabolic disease" are used interchangeably and refer to diseases or disorders concerning both the cardiovascular system and the metabolic system. Examples of cardiometabolic disorders include, but are not limited to, diabetes and dyslipidemias. In cardiometabolic disorders, inflammation is a key component of pathogenesis and the anti-inflammatory properties of the compounds of the present invention are useful to treat these diseases.

In one embodiment, the invention provides a method of treating a cardiometabolic disorder comprising administering to a subject in need thereof a therapeutically effective amount of a compound of Formula I:

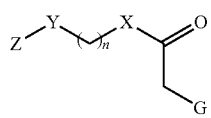

Formula I or a pharmaceutically acceptable salt thereof; wherein n is an integer from 0 to 18;
X is O, S, or NH;
Y is $CH_2$, O, S, or NH;
Z is alkyl, alkenyl, alkynyl, cycloalkyl, aryl, or heterocyclyl, each of which is optionally substituted;
the group G is either G1 or G2;

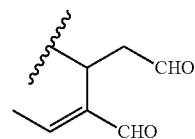

G1

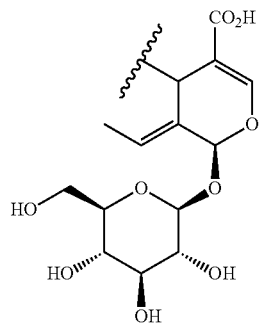

G2 and wherein the compound is not oleacein or oleocanthal.

In certain embodiments, the cardiometabolic disorder comprises Type II diabetes, vascular disease, myocardial ischemia, coronary artery disease, atherosclerosis, thrombosis, hypertension, hypercholesterolemia, or hypertriglyceridemia.

Additional embodiments of the present invention include methods of treating cancer comprising administering to a subject in need thereof a therapeutically effective amount of a compound of Formula I or related Formulas described herein, or a pharmaceutically acceptable salt thereof, alone or in combination with one or more pharmaceutically acceptable excipient, carrier or vehicle.

In one embodiment, the invention provides a method of treating cancer comprising administering to a subject in need thereof a therapeutically effective amount of a compound of Formula I:

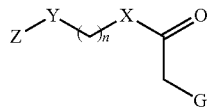

Formula I or a pharmaceutically acceptable salt thereof; wherein:
n is an integer from 0 to 18;
X is O, S, or NH;
Y is $CH_2$, O, S, or NH;

Z is alkyl, alkenyl, alkynyl, cycloalkyl, aryl, or heterocyclyl, each of which is optionally substituted;
the group G is either G1 or G2;

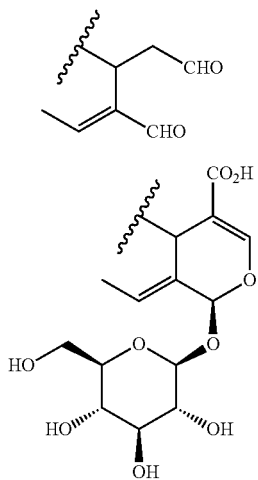

and wherein the compound is not oleacein or oleocanthal.

In certain embodiments, methods of treating cancer comprise administration of one or more compounds selected from the group consisting of:

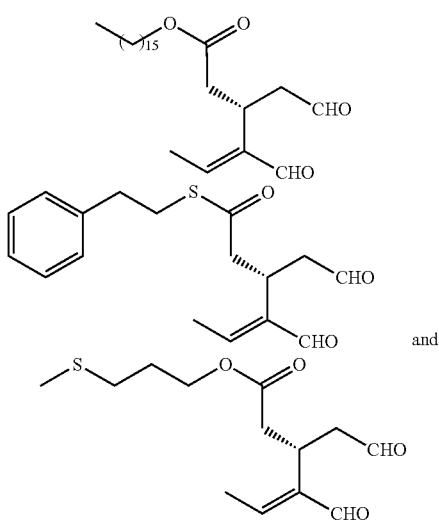

or a pharmaceutically acceptable salt thereof.

The term "cancer" refers to or describes the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer, lung cancer, breast cancer, colon cancer, rectal cancer, colorectal cancer, bladder cancer, anal cancer, cervical cancer, vulval cancer, endometrial or uterine cancer, cancer of the peritoneum, ovarian cancer, pancreatic cancer, liver cancer, gastric or stomach cancer, kidney or renal cancer, prostate cancer, penile cancer, glioblastoma, small-cell lung cancer, non-small cell lung cancer ("NSCLC"), adenocarcinoma of the lung and squamous carcinoma of the lung, hepatocellular cancer, as well as head and neck cancer.

The term "chemotherapeutic agent" refers to a chemical compound useful in the treatment of cancer, regardless of mechanism of action. Classes of chemotherapeutic agents include, but are not limited to, alkylating agents; cytotoxic/antitumor antibiotics; topoisomerase inhibitors; antibodies; photosensitizers; and kinase inhibitors.

Examples of chemotherapeutic agents include, but are not limited to, carboplatin (PARAPLATIN®); oxaliplatin (ELOXATIN®); cisplatin (PLATINOL®); vincristine (ONCOVIN®); paclitaxel (TAXOL®); docetaxel (TAXOTERE®); etoposide (ETOPOPHOS®); irinotecan (CAMPTOSAR®); topotecan (HYCAMTIN®); doxorubicin (ADRIAMYCIN®); mitomycin (MUTAMYCIN®); methotrexate (TREXALL®); 5-fluorouracil (ADRUCIL®); capecitabine (XELODA®); gemcitabine (GEMZAR®); cytarabine (CYTOSAR-U®); erlotinib (TARCEVA®); temozolomide (TEMODAR®); tamoxifen (NOLVADEX®); and rapamycin (SIROLIMUS®).

Also included in the definition of "chemotherapeutic agent" are therapeutic antibodies such as alemtuzumab (LEMTRADA®); bevacizumab (AVASTIN®); cetuximab (ERBITUX®); panitumumab (VECTIBIX®); rituximab (RITUXAN®); pertuzumab (PERJETA®); trastuzumab (HERCEPTIN®); radiolabeled antibodies such as I-131-tositumomab (BEXXAR®) and Y-90-ibritumomab tuxetan (ZEVALIN®); and antibody drug conjugates such as brentuximab vedotin (ADCETRIS®) and ado-trastuzumab emtansine (KADYCLA®).

Cancer is a disease driven by mutations in different genes. Specific genes and gene mutations are involved in the pathogenesis of specific cancer types. Importantly, there are genes that are drivers of oncogenesis for specific cancer types, thus inhibition of their expression have therapeutic effects in these cancers.

In certain embodiments, the cancer is a farnesyltransferase (FNTA)-associated cancer selected from the group consisting of HER2 positive breast cancer, non-small cell lung cancer (NSCLC), bladder cancer, pancreatic cancer, acute myeloid leukemia (AML), myelodysplastic syndrome, chronic myelogenous leukemia (CML) and multiple myeloma.

In certain embodiments, the cancer is a phosphodiesterase 10A (PDE10A)-associated cancer selected from the group consisting of lung, colon and prostate cancers.

In certain embodiments, the cancer is a β-hydroxy β-methylglutaryl-coenzyme A reductase (HMG-CoAR)-associated cancer selected from the group consisting of ovarian, breast, cancer and hepatocellular cancers.

In certain embodiments, the cancer is an ATP citrate lyase (ACLY)-associated cancer selected from the group consisting of lung, prostate, bladder, breast, ovarian, liver, stomach, pancreatic and colorectal cancers.

In certain embodiments, the cancer is a cyclin-dependent kinase 2 (CDK2)-associated cancer selected from the group consisting of gastric, bladder, prostate, MYNC-amplified neuroblastomas, KRAS mutant-lung cancer, CCNE-1-amplified ovarian cancer and sarcoma.

In certain embodiments, the cancer is a cyclin-dependent kinase 4 (CDK4)-associated cancer selected from the group consisting of ER-positive breast cancer, esophageal squamous cell cancer and small cell lung cancer.

In certain embodiments, the cancer is associated with overexpression of at least one of farnesyltransferase (FNTA), phosphodiesterase 10A (PDE10A), β-hydroxy β-methylglutaryl-coenzyme A reductase (HMG-CoAR), ATP citrate lyase (ACLY), cyclin-dependent kinase 2 (CDK2), or cyclin-dependent kinase 4 (CDK4) proteins.

ATP-citrate lyase (ACLY) is a cytosolic enzyme that converts mitochondria-derived citrate into acetyl CoA, which is a precursor for both fatty acid and mevalonate synthesis pathways. ACLY is reported to be upregulated in cancer cells, and its inhibition suppresses proliferation of certain types of tumor cells. Distinctive elevation of ACLY expression and activity has been reported in lung, prostate, bladder, breast, liver, stomach, and colon tumors. (See, Zaidi, Nousheen et al., Cancer Res, 2012, 72: 3709-3714).

In a preferred embodiment, methods of treating cancer associated with overexpression of ATP citrate lyase (ACLY) protein comprise administration of a therapeutically effective amount of:

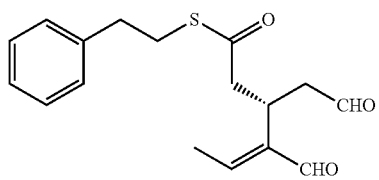

or a pharmaceutically acceptable salt thereof.

Also related to cancer treatment, embodiments of the invention include methods of inhibiting an ATP Citrate Lyase (ACLY)-associated disease comprising administering to a subject in need thereof a therapeutically effective amount of a compound of Formula (I-a):

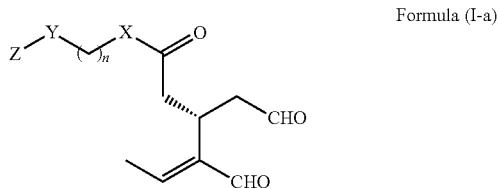

Formula (I-a)

or pharmaceutically acceptable salt thereof; wherein:
n is an integer from 0 to 18;
X is O, S, or NH;
Y is $CH_2$, O, S, or NH; and
Z is alkyl, alkenyl, alkynyl, cycloalkyl, aryl, or heterocyclyl, each of which is optionally substituted.

In a preferred embodiment of the invention, the compound of Formula (I-a) is a compound wherein X=S.

In certain embodiments, the ACLY-associated disease comprises hypercholesterolemia, Type II diabetes, atherosclerosis, chronic metabolic acidosis, hepatitis C, pancreatitis, nonalcoholic fatty liver disease (NAFLD) or cancer.

In certain embodiments, the ACLY-associated disease is a cancer selected from the group consisting of lung, prostate, bladder, breast, ovarian, liver, stomach, pancreatic and colorectal cancers.

In certain embodiments, the method of inhibiting an ATP Citrate Lyase (ACLY)-associated disease inhibits cancer cell growth, development, or metastasis. In certain embodiments, the method of inhibiting an ATP Citrate Lyase (ACLY)-associated disease suppresses ACLY phosphorylation and enzymatic activity in cancer cells.

In a preferred embodiment, the method of inhibiting an ACLY-associated disease comprises administration of a therapeutically effective amount of

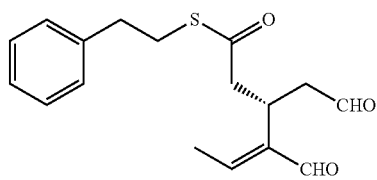

or a pharmaceutically acceptable salt thereof.

In yet another embodiment, the present invention is directed to a method of treating an ATP Citrate Lyase (ACLY)-associated disease comprising administering to a subject in need thereof a therapeutically effective amount of a compound of formula

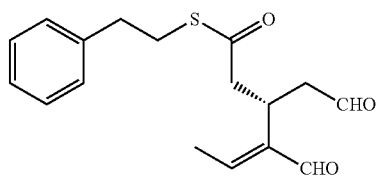

or a pharmaceutically acceptable salt thereof, wherein the compound has an inhibitory efficacy against the ACLY protein.

In certain embodiments, the ACLY-associated disease comprises hypercholesterolemia, type II diabetes, atherosclerosis, chronic metabolic acidosis, hepatitis C, pancreatitis, nonalcoholic fatty liver disease (NAFLD) or cancer.

In certain embodiments, the ACLY-associated disease is a cancer selected from the group consisting of lung, prostate, bladder, breast, ovarian, liver, stomach, pancreatic and colorectal cancers.

In certain embodiments, the method further comprises administering to the subject an additional chemotherapeutic agent, wherein the additional chemotherapeutic agent comprises carboplatin, oxaliplatin, cisplatin, vincristine, paclitaxel, docetaxel, etoposide, irinotecan, topotecan, doxorubicin, mitomycin, methotrexate, 5-fluorouracil, capecitabine, gemcitabine or cytarabine.

In certain embodiments, the method further comprises administering to the subject an immunotherapy agent, wherein the additional immunotherapy agent comprises a PD-1 inhibitor, a PD-L1 inhibitor, a CTLA-4 inhibitor, interleukin-2, a homologous or allogeneic CAR T-cell therapy or a tumor-infiltrating lymphocyte (TIL) therapy.

Accordingly, the compounds of the present specification may be of value as anti-tumor agents, in particular as selective inhibitors of the proliferation, survival, motility, dissemination and invasiveness of mammalian cancer cells leading to inhibition of tumor growth and survival and to inhibition of metastatic tumor growth. For example, the compounds of the present specification may be of value as anti-proliferative and anti-invasive agents in the containment and/or treatment of solid tumor disease. Particularly, the compounds of the present specification may be useful in the prevention or treatment of those tumors which are sensitive to inhibition of ATP Citrate Lyase (ACLY) and that are involved in the signal transduction steps which lead to the proliferation and survival of tumor cells and the migratory ability and invasiveness of metastasizing tumor cells.

Additional embodiments of the present invention include methods of inhibiting free radical damage in human skin by topical or transdermal administration to a subject in need thereof a therapeutically effective amount of a compound of Formula I or related Formulas described herein, or a pharmaceutically acceptable salt thereof, alone or in combination with one or more pharmaceutically acceptable excipient, carrier or vehicle.

In one embodiment, the invention provides a method of inhibiting free radical damage in human skin by topical or transdermal administration to a subject in need thereof a therapeutically effective amount of a compound of Formula I:

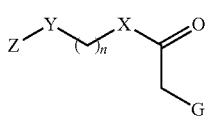

Formula I or a pharmaceutically acceptable salt thereof; wherein:
n is an integer from 0 to 18;
X is O, S, or NH;
Y is $CH_2$, O, S, or NH;
Z is alkyl, alkenyl, alkynyl, cycloalkyl, aryl, or heterocyclyl, each of which is optionally substituted;
the group G is either G1 or G2;

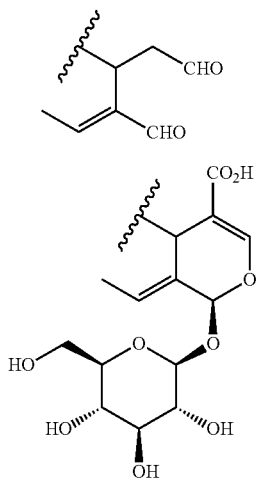

and wherein the compound is not oleacein or oleocanthal.

In another embodiment, the present invention provides methods of treating a condition or disorder associated with free radical damage in human skin by topical or transdermal administration to a subject in need thereof a therapeutically effective amount of a compound of Formula I or related Formulas described herein, or a pharmaceutically acceptable salt thereof, alone or in combination with a pharmaceutically acceptable excipient, carrier or vehicle.

In certain embodiments, the condition or disorder associated with free radical damage comprises sun-induced skin damage, skin aging, skin inflammatory disorders, melasma, skin acne, skin wrinkles, eczema, rosacea, seborrheic dermatitis, or skin degenerative or disorders such as granuloma annulare and follicular degeneration syndrome.

In certain embodiments, methods of treating a condition or disorder associated with free radical damage in human skin comprising administration of one or more compounds selected from the group consisting of:

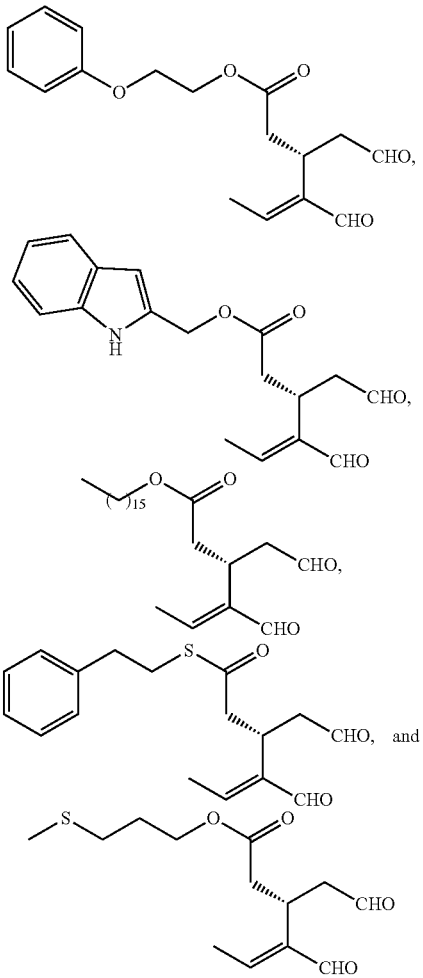

or a pharmaceutically acceptable salt thereof.

In certain embodiments, the pharmaceutical composition for topical or transdermal administration comprises one or more additional therapeutic agents.

Active agents that could be combined with the inventive compounds for skin care products include, but are not limited to: SPF-boosting ingredients (zinc oxide, titanium dioxide, avobenzone); vitamins A, C, D and E; hyaluronic acid; hydroquinone; salicylic acid; azelaic acid; urea; lactic acid; tacrolimus; and benzoyl peroxide.

The first line of screening for assessing the potential antioxidant activity exhibited by a compound comprises evaluating the proper biomarkers in vitro. A compound's antiradical capacity can be revealed spectrophotometrically by examining the scavenging ability of a compound against commercial (e.g., 2,2-diphenyl-1-picrylhydrazyl (DPPH.); 2,2'-azino-bis(3-ethylbenzothiazoline-6-sulphonic acid) (ABTS.$^+$)] and natural (e.g., superoxide ($O_2$.$^-$); hydroxyl (O.)] free radicals. A polyphenolic compound is considered an antioxidant when it donates one electron to free radicals leading to their neutralization and, therefore, protects biomolecules against detrimental oxidative modifications. The evaluation of the reducing capacity of a compound is reliably monitored via the reducing power assay, which examines its ability to reduce ferrous ($Fe^{+3}$) to ferric ($Fe^{+2}$) ions, meaning that it is a strong electron donor and, hence, a reducing agent capable of protecting cells against redox perturbations.

The second line of screening includes biomarkers for the evaluation of the protective activity of polyphenolic compounds against free radical-induced DNA damage. Specifically, the ability of a compound to inhibit the double stranded DNA scission induced by peroxyl (ROO.) radicals that are artificially generated using an agarose gel is a reliable indication of its antioxidant nature, at least in vitro. There is increasing research interest regarding the cytoprotective effects of dietary compounds in in vivo-like systems, specifically cell culture environment against oxidative stress aiming towards the discovery of potential therapeutic and chemopreventive agents. The physiological and cancer cell lines are quite useful tools in order to mechanistically examine the capacity of plant derived compounds to alter cell redox equilibrium and proliferation status.

The compounds of the present invention may be used in the manufacture of a medicament for the treatment of various diseases, disorders, or conditions.

In an embodiment, the compounds of Formula I and related Formulas described herein may be used in the manufacture of a medicament for the treatment of a gastrointestinal inflammatory disorder (e.g., hypercholesterolemia, Type II diabetes, atherosclerosis, chronic metabolic acidosis, hepatitis C, pancreatitis, nonalcoholic fatty liver disease (NAFLD) or cancer); an autoimmune inflammatory disorder (e.g., systemic lupus erythematosus, psoriasis, rheumatoid arthritis, Type 1 diabetes, multiple sclerosis, Sjogren syndrome, atopic dermatitis, Behcet's Disease and Familial Mediterranean Fever) a viral inflammatory disorder (e.g., influenza virus infection or SARS-CoV2 infection); or a cardiovascular inflammatory disorder (e.g., coronary artery disease, atherosclerosis, hypercholesterolemia and hypertriglyceridemia).

In another embodiment, the compounds of Formula I and related Formulas described herein may be used for the manufacture of a medicament for the treatment of a cardiometabolic disorder (e.g., Type II diabetes, vascular disease, myocardial ischemia, coronary artery disease, atherosclerosis, thrombosis, hypertension, hypercholesterolemia, or hypertriglyceridemia).

In yet another embodiment, the compounds of Formula I and related Formulas described herein may be used in the manufacture of a medicament for the treatment of an ATP Citrate Lyase (ACLY)-associated disease, such as hypercholesterolemia, Type II diabetes, atherosclerosis, chronic metabolic acidosis, hepatitis C, pancreatitis, nonalcoholic fatty liver disease (NAFLD) or cancer.

EXAMPLES

The following non-limiting examples are provided to further illustrate the present invention.

Unless otherwise indicated, all temperatures are expressed in ° C. (degrees Centigrade). All solvents used were commercially available and were used without further purification. Reactions were typically run using anhydrous solvents under an inert atmosphere. Flash chromatography was performed on Merck silica gel 60 (0.040-0.063 mm) (Merck, Kenilworth, NJ). Analytical TLC was carried out on precoated (0.25 mm) Merck silica gel F-254 plates.

$^1$H NMR and $^2$D spectra were recorded on a Bruker Avance III 600 spectrometer (Bruker, Billerica, MA), whereas $^{13}$C NMR spectra were recorded on a Bruker Avance III 600 spectrometer in deuterated solvents. Chemical shifts are expressed as δ values in parts per million (ppm), and the coupling constants (J) are given in hertz (Hz). The signals of $^1$H and $^{13}$C NMR spectra were unambiguously assigned by using 2D NMR techniques: 1H-1H COSY, HSQC, and HMBC. HRMS were obtained on a LTQ-Orbitrap Discovery Mass Spectrometer (Thermo Scientific, Brehmen, Germany).

Abbreviations

AA acetaldehyde
CH2Cl2 dichloromethane
CPC centrifugal partition chromatography
DMAP 4-dimethylaminopyridine
EDA elenolic acid dialdehyde
Et2NH diethylamine
Et3N triethylamine
EtOAC ethyl acetate
EtOH ethanol
H2O water
HCl hydrochloric acid
HOAc acetic acid
MeOH methanol
Na2SO4 sodium sulfate
NaOAc sodium acetate
NaOH sodium hydroxide
RT room temperature
TLC thin layer chromatography
v/v volume/volume

CHEMICAL SYNTHESIS EXAMPLES

Example 1—Synthesis of Oleoside (GS2)

Oleoside, also (2S,4S,E)-4-(carboxymethyl)-3-Ethylidene-2-{[(2R,3S,4R,5R,6S)-3,4,5-trihydroxy-6-(hydroxymethyl)tetrahydro-2H-pyran-2-yl]oxy}-3,4-dihydro-2H-pyran-5-carboxylic acid (GS2), was obtained by saponification of an acetone soluble fraction of olive leaves, which contain an abundant amount of oleuropein (GS1). It was found that yield depended on the variety of olive leaves used as starting material, since the concentration of oleuropein varies in different olive tree species.

Extraction of Koroneiki variety olive leaves with acetone followed by solvent evaporation yielded a crude material containing oleuropein (ca. 40% purity by HPLC). The crude material (20 g, 14.81 mmol) was dissolved in 130 mL of 1 N NaOH solution. The mixture was stirred at room temperature and the reaction was monitored with TLC. After completion (approximately 24 h), a 1 N HCl solution was added to reach a pH around 4-5. The solvent was evaporated under vacuum and the crude mixture of oleoside was subjected to fast centrifugal partition chromatography (FCPC) using a two-phase solvent system comprising EtOAc:isopropanol:EtOH:H2O:AA in a ratio of 8:2:1:10:0.5 (v:v:v:v:v) (6.45 L). The two phases were separated after thorough equilibration in a separatory funnel at room temperature. The lower aqueous phase was used as the stationary phase, and the upper organic phase was employed as the mobile phase. Initially the CPC column (1 L) was filled with the aqueous stationary phase with no rotation and a flow rate of 20 mL/min; then the mobile organic phase was pumped into the column in the ascending mode at a flow rate of 15 mL/min and with a rotation of 800 rpm.

This protocol afforded 4.54 g of oleoside (purity of 90%) from 380 g of olive leaves. Fractions containing oleoside of lower purity (1.0 g purity of 44% and 0.98 g purity of 32%) were also collected. All oleoside fractions were purified by crystallization from water to give a combined overall yield of 4.7 g of oleoside (81%) having a purity >95%. This sequence provides a simple and powerful approach to obtain large amounts (tens of gram scale) of key intermediate GS1. Overall, 4.7 g of oleoside (GS1) was obtained in a purity >95%.

Characterization of GS2.

$^1$H NMR (600 MHz, D$_2$O) δ 7.68 (s, 1H, H-3), 6.25 (q, $J_{8,10}$=7.09 Hz, 1H, H-8), 6.04 (s, 1H, H-1), 5.04 (d, $J_{1',2'}$=8.03 Hz, 1H, H-1'), 4.11 (dd, $J_{5,6b}$=9.63, $J_{5,6a}$=4.57 Hz, 1H, H-5), 4.01 (dd, $J_{6a',6b'}$=12.49, $J_{6a',5'}$=2.20 Hz, 1H, H-6a'), 3.83 (dd, $J_{6b',6a'}$=12.49, $J_{6b',5}$=5.92 Hz, 1H, H-6b'), 3.65-3.62 (m, 1H, H-3'), 3.61 (ddd, $J_{5',4'}$=8.20, $J_{5',6b'}$=5.92, $J_{5',6a'}$=2.20 Hz 1H, H-5'), 3.54-3.52 (m, 1H, H-4'), 3.52-3.50 (m, 1H, H-2'), 2.91 (dd, $J_{6a,6b}$=13.67, $J_{6a,5}$=4.57 Hz, 1H, H-6a), 2.54 (dd, $J_{6b,6a}$=13.67, $J_{6b,5}$=9.63 Hz, 1H, H-6b), 1.84 (dd, $J_{10,8}$=7.12, $J_{10,1}$=1.30 Hz, 3H, H-10).

$^{13}$C NMR (151 MHz, D$_2$O) δ 176.47 (C-7), 170.50 (C11), 154.62 (C-3), 128.46 (C-9), 125.06 (C-8), 108.68 (C-4), 99.73 (C-1'), 94.96 (C-1), 76.42 (C5'), 75.74 (C-3'), 72.73 (C-2'), 69.55 (C-4'), 60.71 (C-6'), 40.31 (C-6), 30.70 (C-5), 12.88 (C-10);

HRMS (ESI−) m/z 389.1091 (calcd for C$_{16}$H$_{21}$O$_{11}$ 389.1089).

Example 2—General Procedure for the Synthesis of Oleoside Esters and Thioesters

Acetic anhydride (1.69 mL, 17.94 mmol, 17.5 equiv) was added to a solution of GS2 (400.0 mg, 1.025 mmol, 1 equiv) in pyridine (0.8 mL, 10.25 mmol, 10 equiv) at 0° C., and the resulting mixture was stirred at room temperature (rt) for 3h, under argon. After completion of the reaction, as indicated upon TLC monitoring (Rf 0.50, c-hex-EtOAc 1:1), the mixture was concentrated under reduced pressure to afford a mixed anhydride intermediate. The crude mixed anhydride I, without any further purification, was dissolved in dry acetonitrile (5 mL) and the appropriate alcohol or thiol (1.2 equiv), Et3N (285.90 μL, 2.05 mmol, 2 equiv), and DMAP (125 mg, 1.025 mmol, 1 equiv) were added. The resulting solution was stirred at room temperature for 3h, acidified with 2N HCl (pH ~4-5), and vacuum-evaporated. The residue was dissolved in CH2Cl2, washed with water, dried (anhydrous Na2SO4), and concentrated to dryness to afford a crude intermediate ester or thioester. Without further purification, the residue was dissolved in MeOH and Et2NH (5-8 equiv) was added. The resulting solution was stirred for 6h at room temperature, acidified with HCl 9% (pH ~4-5), and evaporated to dryness. The residue was dissolved in EtOAc, washed with water, dried (anhydrous Na2SO4), and concentrated to dryness. The crude product was purified by flash chromatography (silica gel), using CH2Cl2/MeOH, 100→85:15 v/v as the eluent, to afford the corresponding products GS3-GS15.

Example 3—Synthesis of GS3

Oleoside 7-adamantan-1-ylmethyl ester, also (2S,4S,E)-4-(2-(adamantan-1-ylmethoxy)-2-oxoethyl)-3-ethylidene-2-{[(2R,3S,4R,5R,6S)-3,4,5-trihydroxy-6-(hydroxymethyl) tetrahydro-2H-pyran-2-yl]oxy}-3,4-dihydro-2H-pyran-5-carboxylic acid (GS3), was obtained in 39% yield according to the procedure of Example 2.

Characterization of GS3.

$^1$H NMR (600 MHz, D$_2$O) δ 7.33 (s, 1H, H-3), 6.17 (q, $J_{8,10}$=7.05 Hz, 1H, H-8), 5.95 (s, 1H, H-1), 5.01 (d, $J_{1'',2''}$=8.04 Hz, 1H, H-1''), 4.09 (dd, $J_{5,6b}$=9.61, $J_{5,6a}$=4.29 Hz, 1H, H-5), 4.01 (dd, $J_{6a'',6b''}$=12.39, $J_{6a'',5''}$=2.22 Hz, 1H, H-6a''), 3.87 (d, $J_{1a',1b'}$=10.88 Hz, 1H, H-1a'), 3.82 (dd, $J_{6b'',6a''}$=12.37, $J_{6b'',5''}$=6.02 Hz, 1H, H-6b''), 3.66 (d, $J_{1b',1a'}$=10.67 Hz, 1H, H-1b'), 3.65-3.62 (m, 1H, H-3''), 3.59 (ddd, $J_{5'',4''}$=8.33, $J_{5'',6b''}$=6.02, $J_{5'',6a''}$=2.20 Hz 1H, H-5''), 3.51-3.50 (m, 1H, H-4''), 3.49-3.48 (m, 1H, H-2''), 2.89 (dd, $J_{6a,6b}$=13.40, $J_{6a,5}$=4.30 Hz, 1H, H-6a), 2.65 (dd, $J_{6b,6a}$=13.40, $J_{6b,5}$=9.60 Hz, 1H, H-6b), 2.04 (b, 3H, H-4'/H-6'/H-8'), 1.82-1.80 (m, 6H, H-10/H-5a'/H-7a'/H-10a'), 1.75-1.73 (m, 3H, H-5b'/H-7b'/H-10b'), 1.61-1.60 (m, 6H, H-3'/H-9'/H-11');

$^{13}$C NMR (151 MHz, D$_2$O) δ 175.02 (C-7), 174.24 (C-11), 149.77 (C-3), 129.79 (C-9), 124.09 (C-8), 114.63 (C-4), 99.21 (C-1''), 94.03 (C-1), 76.46 (C-5''), 75.79 (C-3''), 75.22 (C-1'), 72.91 (C-2''), 69.72 (C-4''), 60.98 (C-6''), 40.06 (C-6), 38.63 (C-3'/C-9'/C-11'), 36.44 (C-5'/C-7'/C-10'), 32.65 (C-2'), 31.80 (C-5), 27.84 (C-4'/C-6'/C-8'), 12.92 (C-10);

HRMS (ESI−) m/z 537.2347 (calcd for C$_{27}$H$_{37}$O$_{11}$, 537.2341).

Example 4—Synthesis of GS4

Oleoside 7-phenylethyl ester, also (2S,4S,E)-3-ethylidene-4-(2-oxo-2-phenethoxyethyl)-2-{[(2R,3S,4R,5R,6S)-3,4,5-trihydroxy-6-(hydroxymethyl)tetrahydro-2H-pyran-2-yl]oxy}-3,4-dihydro-2H-pyran-5-carboxylic acid (GS4), was obtained in 37% yield according to the procedure of Example 2.

Characterization of GS4.

$^1$H NMR (600 MHz, methanol-d$_4$) δ 7.52 (s, 1H, H-3), 7.31-7.29 (m, 2H, H-5'/H-7'), 7.26-7.25 (m, 2H, H-4'/H-8'), 7.22-7.20 (m, 1H, H-6'), 6.10 (q, $J_{8,10}$=6.98 Hz, 1H, H-8), 5.93 (s, 1H, H-1), 4.83 (d, $J_{1'',2''}$=7.85 Hz, 1H, H-1''), 4.31 (dt, $J_{1a',1b'}$=10.75 Hz, $J_{1a',2'}$=6.95 Hz, 1H, H-1a'), 4.21 (dt, $J_{1b',1a'}$=10.75 Hz, $J_{1b',2'}$=7.05 Hz, 1H, H-1b'), 4.00 (dd, $J_{5,6b}$=9.29, $J_{5,6a}$=4.59 Hz, 1H, H-5), 3.92 (dd, $J_{6a'',6b''}$=11.96, $J_{6a'',5''}$=1.75 Hz, 1H, H-6a''), 3.71 (dd, $J_{6b'',6a''}$=11.96, $J_{6b'',5''}$=5.52 Hz, 1H, H-6b''), 3.46 (m, 1H, H-3''), 3.38-3.36 (m, 1H, H-5''), 3.35-3.34 (m, 2H, H-2''/H-4''), 2.95 (t, $J_{2',1a',1b'}$=6.96 Hz, 2H, H-2'), 2.79 (dd, $J_{6a,6b}$=14.12, $J_{6a,5}$=4.56 Hz, 1H, H-6a), 2.48 (dd, $J_{6b,6a}$=14.10, $J_{6b,5}$=9.26 Hz, 1H, H-6b), 1.67 (dd, $J_{10,8}$=7.10, $J_{10,1}$=1.05 Hz, 3H, H-10);

$^{13}$C NMR (151 MHz, methanol-d$_4$) δ 173.25 (C-7), 170.33 (C-11), 154.73 (C-3), 130.82 (C-9), 130.02 (C-4'/C-8'), 129.51 (C-5'/C-7'), 127.49 (C-6'), 124.57 (C-8), 110.14 (C-4), 100.87 (C-1''), 95.05 (C-1), 78.41 (C-5''), 77.96 (C-3''), 74.81 (C-2''), 71.55 (C-4''), 66.49 (C-1'), 62.80 (C-6''), 41.22 (C-6), 35.98 (C-2'), 31.93 (C-5), 13.52 (C-10);

HRMS (ESI−) m/z 493.1720 (calcd for C$_{24}$H$_{29}$O$_{11}$, 493.1715).

Example 5—Synthesis of GS5

Oleoside 7-cyclohexylethyl ester, also (2S,4S,E)-4-(2-(2-cyclohexylethoxy)-2-oxoethyl)-3-ethylidene-2-{[(2R,3S,4R,5R,6S)-3,4,5-trihydroxy-6-(hydroxymethyl)tetrahydro-2H-pyran-2-yl]oxy}-3,4-dihydro-2H-pyran-5-carboxylic acid (GS5), was obtained in 38% yield according to the procedure of Example 2.

Characterization of GS5.

$^1$H NMR (600 MHz, methanol-d$_4$): δ 7.52 (s, 1H, H-3), 6.14 (q, J8,10=7.03 Hz, 1H, H-8), 5.94 (s, 1H, H-1), 4.84 (d, J1'',2''=7.86 Hz, 1H, H-1''), 4.17 (dt, J1a',1b'=10.52 Hz, J1a',2'=6.87 Hz, 1H, H-1a'), 4.05 (dt, J1b',1a'=10.87 Hz, J1b',2'=6.67 Hz, 1H, H-1b'), 4.03 (dd, J5,6b=8.95, J5,6a=4.47 Hz, 1H, H-5), 3.92 (dd, J6a'',6b''=12.09, J6a'',5=2.02 Hz, 1H, H-6a''), 3.71 (dd, J6b'',6a''=12.09, J6b'',5''=5.84 Hz, 1H, H-6b''), 3.45 (m, 1H, H-3''), 3.38 (ddd, J5",4"=9.71, J5",6b"=5.84, J5",6a"=2.15 Hz 1H, H-5"), 3.35-3.34 (m, 2H, H-2"/H-4"), 2.80 (dd, J6a,6b=14.00, J6a,5=4.51 Hz, 1H, H-6a), 2.51 (dd, J6b,6a=13.97, J6b,5=9.34 Hz, 1H, H-6b), 1.77 (dd, J10,8=7.11, J10,1=1.44 Hz, 3H, H-10), 1.74-1.73 (m, 2H, H-4a'/H-8a'), 1.72-1.67 (m, 3H, H-5a'/H-6a'/H-7a'), 1.57-1.51 (m, 2H, H-2'), 1.44-1.37 (m, 1H, H-3'), 1.35 (m, 2H, H-5b'/H-7b'), 1.24-1.17 (m, 1H, H-6b'), 1.00-0.92 (m, 2H, H-4b'/H-8b');

$^{13}$C NMR (151 MHz, methanol-$d_4$): δ 173.48 (C-7), 170.39 (C-11), 154.62 (C-3), 131.03 (C-9), 124.39 (C-8), 110.29 (C-4), 100.77 (C-1"), 94.93 (C-1), 78.45 (C-5"), 77.98 (C-3"), 74.83 (C-2"), 71.62 (C-4"), 63.90 (C-1'), 62.88 (C-6"), 41.26 (C-6), 37.08 (C-2'), 35.69 (C-3'), 34.34 (C-4'), 34.22 (C-8'), 32.07 (C-5), 27.60 (C-6'), 27.31 (C-5'), 27.28 (C-7'), 13.61 (C-10);

HRMS (ESI−) m/z 499.2189 (calcd for $C_{24}H_{35}O_{11}$, 499.2185).

Example 6—Synthesis of GS6

Demethyloleuropein, also (2S,4S,E)-4-(2-(3,4-dihydroxyphenethoxy)-2-oxoethyl)-3-ethylidene-2{[(2R,3S,4R,5R,6S)-3,4,5-trihydroxy-6-(hydroxymethyl)tetrahydro-2H-pyran-2-yl]oxy}-3,4dihydro-2H-pyran-5-carboxylic acid (GS6), was obtained in 36% yield according to the procedure of Example 2.

Characterization of GS6.

$^1$H NMR (600 MHz, $D_2O$): δ 7.48 (s, 1H, H-3), 6.95 (d, $J_{7',8'}$=8.12 Hz, 1H, H-7'), 6.90 (d, $J_{4',8}$=2.00 Hz, 1H, H-4'), 6.81 (dd, $J_{8',7'}$=8.05 Hz, $J_{8',4'}$=1.99 Hz, 1H, H-8'), 6.10 (q, $J_{8,10}$=6.96 Hz, 1H, H-8), 5.81 (s, 1H, H-1), 4.95 (d, $J_{1",2"}$=7.95 Hz, 1H, H-1"), 4.39 (dt, $J_{1a',1b'}$=10.79, $J_{1a',2}$=6.52 Hz, 1H, H-1a'), 4.26 (dt, $J_{1b',1a'}$=10.95 Hz, $J_{1b',2}$=6.36 Hz, 1H, H-1b'), 3.99-3.96 (m, 1H, H-5), 3.98 (dd, $J_{6a",6b"}$=12.30, $J_{6a",5"}$=2.05 Hz, 1H, H-6a"), 3.82 (dd, $J_{6b",6a"}$=12.30, $J_{6b",5"}$=5.55 Hz, 1H, H-6b"), 3.65-3.62 (m, 1H, H-3"), 3.58 (ddd, $J_{5",4"}$=9.97, $J_{5",6b"}$=5.26, $J_{5",6a"}$=1.94 Hz 1H, H-5"), 3.54-3.52 (m, 1H, H-4"), 3.52-3.49 (m, 1H, H-2"), 2.91 (t, $J_{2',1a',1b'}$=6.05 Hz, 2H, H-2'), 2.80 (dd, $J_{6a,6b}$=13.67, $J_{6a,5}$=4.71 Hz, 1H, H-6a), 2.57 (dd, $J_{6b,6a}$=13.64, $J_{6b,5}$=8.91 Hz, 1H, H-6b), 1.65 (dd, $J_{10,8}$=7.17, $J_{10,1}$=1.14 Hz, 3H, H-10);

$^{13}$C NMR (151 MHz, $D_2O$): δ 174.33 (C-7), 172.00 (C-11), 152.66 (C-3), 143.93 (C-5'), 142.98 (C-6'), 131.28 (C-3'), 128.89 (C-9), 124.74 (C-8), 121.34 (C-8'), 116.85 (C-4'), 116.38 (C-7'), 110.87 (C-4), 99.59 (C-1"), 76.34 (C-5"), 75.74 (C-3"), 72.75 (C-2"), 69.51 (C-4"), 66.32 (C-1'), 60.71 (C-6"), 39.98 (C-6), 33.42 (C-2'), 30.87 (C-5), 12.61 (C-10);

HRMS (ESI−) m/z 525.1620 (calcd for $C_{24}H_{29}O_{13}$ 525.1614).

Example 7—Synthesis of GS7

Demethyl-ligstroside, also (2S,4S,E)-3-ethylidene-4-(2-(4-hydroxyphenethoxy)-2-oxoethyl)-2{[(2R,3 S,4R,5R,6S)-3,4,5-trihydroxy-6-(hydroxymethyl)tetrahydro-2H-pyran-2-yl]oxy}-3,4dihydro-2H-pyran-5-carboxylic acid (GS7), was obtained in 39% yield according to the procedure of Example 2.

Characterization of GS7.

$^1$H NMR (600 MHz, $D_2O$): δ 7.58 (s, 1H, H-3), 7.25 (d, $J_{4',5'/8',7'}$=7.74 Hz, 2H, H-4'/H-8'), 6.94 (d, $J_{5',4'/7',8'}$=7.85 Hz, 2H, H-5'/H-7'), 6.12 (q, $J_{8,10}$=6.85 Hz, 1H, H-8), 5.86 (s, 1H, H-1), 4.96 (d, $J_{1",2"}$=8.04 Hz, 1H, H-1"), 4.39 (dt, $J_{1a',1b'}$=10.52 Hz, $J_{1a',2}$=6.73 Hz, 1H, H-1a'), 4.27 (dt, $J_{1b',1a'}$=10.56 Hz, $J_{1b',2}$=6.14 Hz, 1H, H-1b'), 3.98 (dd, $J_{6a",6b"}$=12.38, $J_{6a",5"}$=1.68 Hz, 1H, H-6a"), 3.97-3.96 (m, 1H, H-5), 3.82 (dd, $J_{6b",6a"}$=12.33, $J_{6b",5"}$=5.51 Hz, 1H, H-6b"), 3.65-3.62 (m, 1H, H-3"), 3.57 (ddd, $J_{5",4"}$=10.02, $J_{5",6b"}$=5.41, $J_{5",6a"}$=1.89 Hz 1H, H-5"), 3.55-3.52 (m, 1H, H-4"), 3.52-3.50 (m, 1H, H-2"), 2.95 (t, $J_{2',1a',1b'}$=5.98 Hz, 2H, H-2'), 2.78 (dd, $J_{6a,6b}$=13.81, $J_{6a,5}$=4.75 Hz, 1H, H-6a), 2.56 (dd, $J_{6b,6a}$=13.57, $J_{6b,5}$=8.95 Hz, 1H, H-6b), 1.66 (d, $J_{10,8}$=7.10 Hz, 3H, H-10);

$^{13}$C NMR (151 MHz, $D_2O$): δ 174.19 (C-7), 170.78 (C-11), 154.08 (C-3), 130.37 (C-3'/C-4'/C-8'), 128.51 (C-9), 124.98 (C-8), 115.51 (C-5'/C-7'), 109.07 (C-4), 99.57 (C-1"), 94.78 (C-1), 76.38 (C-5"), 75.76 (C-3"), 72.77 (C-2"), 69.44 (C-4"), 66.36 (C-1'), 60.77 (C-6"), 39.87 (C-6), 33.29 (C-2'), 30.53 (C-5), 12.68 (C-10);

HRMS (ESI−) m/z 509.1670 (calcd for C24H29O12 509.1664).

Example 8—Synthesis of GS8

Oleoside 7-(1H-Indole-2)-methyl ester, also (2S,4S,E)-4-(2-((1H-indol-2-yl)methoxy)-2-oxoethyl)-3-ethylidene-2-{[(2R,3S,4R,5R,6S)-3,4,5-trihydroxy-6-(hydroxymethyl)tetrahydro-2H-pyran-2-yl]oxy}-3,4-dihydro-2H-pyran-5-carboxylic acid (GS8), was obtained in 35% yield according to the procedure of Example 2.

Characterization of GS8.

$^1$H NMR (600 MHz, methanol-$d_4$) δ 7.52 (d, $J_{8',7'}$=7.97 Hz, 1H, H-8'), 7.50 (s, 1H, H-3), 7.39 (dd, $J_{5',6'}$=8.13, $J_{5',7'}$=0.68 Hz, 1H, H-5'), 7.14 (dt, $J_{6',5',7'}$=7.31 Hz, $J_{6',8'}$=0.97 Hz, 1H, H-6'), 7.02 (dt, $J_{7',6',8'}$=7.13 Hz, $J_{7',5'}$=1.02 Hz, 1H, H-7'), 6.46 (s, 1H, H-10'), 5.94 (s, 1H, H-1), 5.89 (q, $J_{8,10}$=6.86 Hz, 1H, H-8), 5.32 (d, $J_{1a',1b'}$=12.68 Hz, 1H, H-1a'), 5.17 (d, $J_{1b',1a'}$=12.68 Hz, 1H, H-1b'), 4.80 (d, $J_{1",2"}$=7.83 Hz, 1H, H-1"), 4.01 (dd, $J_{5,6b}$=9.75, $J_{5,6a}$=4.55 Hz, 1H, H-5), 3.95 (d, $J_{6a",6b"}$=11.95, $J_{6a",5"}$=1.21 Hz, Hz, 1H, H-6a"), 3.73 (dd, $J_{6b",6a"}$=11.95, $J_{6b",5"}$=5.15 Hz, 1H, H-6b"), 3.46-3.42 (m, 1H, H-3"), 3.41-3.39 (m, 2H, H-5"), 3.39-3.38 (m, 2H, H-4"), 3.38-3.36 (m, 1H, H-2"), 2.86 (dd, $J_{6a,6b}$=13.77, $J_{6a,5}$=4.53 Hz, 1H, H-6a), 2.56 (dd, $J_{6b,6a}$=13.77, $J_{6b,5}$=9.91 Hz, 1H, H-6b), 1.51 (dd, $J_{10,8}$=7.13, $J_{10,1}$=1.32 Hz, 3H, H-10);

$^{13}$C NMR (151 MHz, methanol-$d_4$): δ 172.97 (C-7), 170.34 (C-11), 154.93 (C-3), 138.37 (C-4'), 134.25 (C-2'), 130.20 (C-9), 129.29 (C-9'), 124.79 (C-8), 122.93 (C-6'), 121.41 (C-8'), 120.29 (C-7'), 112.20 (C-5'), 110.07 (C-4), 103.65 (C-10'), 101.30 (C-1"), 95.46 (C-1), 78.38 (C-5"), 77.99 (C-3"), 74.82 (C-2"), 71.63 (C-4"), 62.71 (C-6"), 60.70 (C-1'), 41.15 (C-6), 32.03 (C-5), 13.35 (C-10);

HRMS (ESI−) m/z 518.16734 (calcd for $C_{25}H_{28}O_{11}N$, 518.1668).

Example 9—Synthesis of GS9

Oleoside 7-(3-(methylthio))-1-propyl ester, also (2S,4S,E)-3-ethylidene-4-(2-(3-(methylthio)propoxy)-2-oxoethyl)-2-{[(2R,3S,4R,5R,6S)-3,4,5-trihydroxy-6-(hydroxymethyl)tetrahydro-2H-pyran-2-yl]oxy}-3,4-dihydro-2H-pyran-5-carboxylic acid (GS9), was obtained in 39% yield according to the procedure of Example 2.

Characterization of GS9.

$^1$H NMR (600 MHz, methanol-$d_4$) δ 7.41 (s, 1H, H-3), 6.11 (q, $J_{8,10}$=7.03 Hz, 1H, H-8), 5.90 (s, 1H, H-1), 4.84 (d, $J_{1",2"}$=7.92 Hz, 1H, H-1"), 4.24 (dt, $J_{1a',1b'}$=11.00 Hz, $J_{1a',2}$=6.41 Hz, 1H, H-1a'), 4.08 (dt, $J_{1b',1a'}$=10.61 Hz, $J_{1b',2}$=6.40 Hz, 1H, H-1b'), 4.06-4.04 (m, 1H, H-5), 3.92 (dd, $J_{6a",6b"}$=11.92, $J_{6a",5"}$=1.89 Hz, 1H, H-6a"), 3.72 (dd, $J_{6b",6a"}$=11.92, $J_{6b",5"}$=5.31 Hz, 1H, H-6b"), 3.45-3.42 (m, 1H, H-3"), 3.38-3.36 (m, 1H, H-5"), 3.36-3.35 (m, 2H, H-4"), 3.35-3.34 (m, 2H, H-2"), 2.88 (dd, $J_{6a,6b}$=14.29, $J_{6a,5}$=4.53 Hz, 1H, H-6a), 2.59 (t, $J_{3',2'}$=7.10 Hz, 2H, H-3'), 2.49 (dd, $J_{6b,6a}$=13.93, $J_{6b,5}$=9.75 Hz, 1H, H-6b), 2.10 (b, 3H, H-5'), 1.94-1.89 (m, 2H, H2'), 1.77 (dd, $J_{10,8}$=7.10, $J_{10,1}$=1.36 Hz, 3H, H-10);

$^{13}$C NMR (151 MHz, methanol-$d_4$): δ 173.57 (C-7), 172.30 (C-11), 152.83 (C-3), 131.54 (C-9), 123.94 (C-8), 112.79 (C-4), 100.84 (C-1"), 94.73 (C-1), 78.39 (C-5"), 77.99 (C-3"), 74.86 (C-2"), 71.58 (C-4"), 64.32 (C-1'), 62.86 (C-6"), 41.28 (C-6), 32.60 (C-5), 31.39 (C-3'), 29.20 (C-2'), 15.24 (C-5'), 13.66 (C-10);

HRMS (ESI−) m/z 477.1439 (calcd for $C_{20}H_{29}O_{11}S$, 477.1436).

Example 10—Synthesis of GS10

Oleoside 7-phenoxyethyl ester, also (2S,4S,E)-3-ethylidene-4-(2-oxo-2-(2-phenoxyethoxy)ethyl)-2-{[(2R,3S,4R,5R,6S)-3,4,5-trihydroxy-6-(hydroxymethyl)tetrahydro-2H-pyran-2-yl]oxy}-3,4-dihydro-2H-pyran-5-carboxylic acid (GS10), was obtained in 37% yield according to the procedure of Example 2.

Characterization of GS10.

$^1$H NMR (600 MHz, methanol-$d_4$) δ 7.52 (s, 1H, H-3), 7.30-7.27 (m, 2H, H-5'/H-7'), 6.96-6.94 (m, 3H, H-4'/H-6'/H-8'), 6.13 (q, $J_{8,10}$=7.07 Hz, 1H, H-8), 5.95 (s, 1H, H-1), 4.82 (d, $J_{1",2"}$=7.90 Hz, 1H, H-1"), 4.44 (dt, $J_{1a',1b'}$=12.18 Hz, $J_{1a',2'}$=4.76 Hz, 1H, H-1a'), 4.37 (dt, $J_{1b',1a'}$=12.03 Hz $J_{1b',2'}$=4.80 Hz, 1H, H-1b'), 4.20 (t, $J_{2',1a',1b'}$=4.91 Hz, 2H, H-2'), 4.05 (dd, $J_{5,6b}$=9.31, $J_{5,6a}$=4.16 Hz, 1H, H-5), 3.90 (dd, $J_{6a",6b"}$=12.30, $J_{6a",5"}$=1.66 Hz, 1H, H-6a"), 3.69 (dd, $J_{6b",6a"}$=12.20, $J_{6b",5"}$=5.53 Hz, 1H, H-6b"), 3.45-3.42 (m, 1H, H-3"), 3.37-3.35 (m, 1H, H-5"), 3.35-3.34 (m, 2H, H-4"), 3.32-3.31 (m, 2H, H-2"), 2.85 (dd, $J_{6a,6b}$=14.40, $J_{6a,5}$=4.11 Hz, 1H, H-6a), 2.56 (dd, $J_{6b,6a}$=14.08, $J_{6b,5}$=9.53 Hz, 1H, H-6b), 1.76 (dd, $J_{10,8}$=7.10, $J_{10,1}$=1.30 Hz, 3H, H-10);

$^{13}$C NMR (151 MHz, methanol-$d_4$): δ 173.17 (C-7), 170.36 (C-11), 160.00 (C-3'), 154.78 (C-3), 130.83 (C-9), 130.49 (C-5'/C-7'), 124.66 (C-8) 122.08 (C-6'), 115.74 (C-4'/C-8'), 110.11 (C-4), 100.87 (C-1"), 95.08 (C-1), 78.36 (C-5"), 77.95 (C-3"), 74.79 (C-2"), 71.52 (C-4"), 66.96 (C-2'), 64.32 (C-1'), 62.77 (C-6"), 41.08 (C-6), 31.92 (C-5), 13.62 (C-10);

HRMS (ESI−) m/z 509.1664 (calcd for $C_{24}H_{29}O_{12}$, 509.1667).

Example 11—Synthesis of GS11

Oleoside 7-(S-2-phenethyl) thioester, also (2S,4S,E)-3-ethylidene-4-(2-oxo-2-(phenethylthio)ethyl)-2-{[(2R,3S,4R,5R,6S)-3,4,5-trihydroxy-6-(hydroxymethyl)tetrahydro-2H-pyran-2-yl]oxy}-3,4-dihydro-2H-pyran-5-carboxylic acid (GS11), was obtained in 58% yield according to the procedure of Example 2.

Characterization of GS11.

$^1$H NMR (600 MHz, methanol-$d_4$) δ 7.55 (s, 1H, H-3), 7.31-7.28 (m, 2H, H-5'/H-7'), 7.24-7.23 (m, 2H, H-4'/H-8'), 7.22-7.19 (m, 1H, H-6'), 6.14 (q, $J_{8,10}$=7.06 Hz, 1H, H-8), 5.96 (s, 1H, H-1), 4.84 (d, $J_{1",2"}$=7.90 Hz, 1H, H-1"), 4.06 (dd, $J_{5,6b}$=9.55, $J_{5,6a}$=3.92 Hz, 1H, H-5), 3.92 (d, $J_{6a",6b"}$=11.89 Hz, 1H, H-6a"), 3.72 (dd, $J_{6b",6a"}$=11.72, $J_{6b",5"}$=4.20 Hz, 1H, H-6b"), 3.46-3.43 (m, 1H, H-3"), 3.39-3.38 (m, 1H, H-4"), 3.37-3.36 (m, 1H, H-5"), 3.36-3.34 (m, 1H, H-2"), 3.13-3.05 (m, 2H, H-1'), 3.00 (dd, $J_{6a,6b}$=14.14, $J_{6a,5}$=4.07 Hz, 1H, H-6a), 2.85 (t, $J_{2',1'}$=7.85 Hz, 2H, H-2'), 2.77 (dd, $J_{6b,6a}$=14.00, $J_{6b,5}$=9.78 Hz, 1H, H-6b), 1.72 (d, $J_{10,8}$=7.08 Hz, 3H, H-10);

$^{13}$C NMR (151 MHz, methanol-$d_4$): δ 198.73 (C-7), 169.88 (C-11), 155.25 (C-3), 141.44 (C-3'), 130.24 (C-9), 129.59 (C-4'/C-8'), 129.49 (C-5'/C-7'), 127.45 (C-6'), 124.92 (C-8) 109.46 (C-4), 100.98 (C-1"), 95.30 (C-1), 78.32 (C-5"), 77.95 (C-3"), 74.77 (C-2"), 71.47 (C-4"), 62.77 (C-6"), 49.67 (C-6), 36.87 (C-2'), 32.52 (C-5), 31.59 (C-1'), 13.75 (C-10).

Example 12—Synthesis of GS12

Oleoside 7-methyl ester, also (2S,4S,E)-3-ethylidene-4-(2-methoxy-2-oxoethyl)-2-{[(2R,3S,4R,5R,6S)-3,4,5-trihydroxy-6-(hydroxymethyl)tetrahydro-2H-pyran-2-yl]oxy}-3,4dihydro-2H-pyran-5-carboxylic acid (GS12), was obtained in 62% yield according to the procedure of Example 2.

Characterization of GS12.

$^1$H NMR (600 MHz, methanol-$d_4$) δ 7.47 (s, 1H, H-3), 6.12 (q, $J_{8,10}$=7.00 Hz, 1H, H-8), 5.90 (s, 1H, H-1), 4.83 (d, $J_{1",2"}$=8.08 Hz, 1H, H-1"), 4.05 (dd, $J_{5,6b}$=9.60, $J_{5,6a}$=4.32 Hz, 1H, H-5), 3.91 (dd, $J_{6a",6b"}$=11.90, $J_{6a",5"}$=1.47 Hz, 1H, H-6a"), 3.72 (dd, $J_{6b",6a"}$=11.91, $J_{6b",5"}$=5.61 Hz, 1H, H-6b"), 3.65 (s, 3H, H-1'), 3.45-3.42 (m, 1H, H-3"), 3.37-3.36 (m, 1H, H-5"), 3.35-3.34 (m, 1H, H-4"), 3.34-3.33 (m, 1H, H-2"), 2.86 (dd, $J_{6a,6b}$=14.19, $J_{6a,5}$=4.46 Hz, 1H, H-6a), 2.47 (dd, $J_{6b,6a}$=14.15, $J_{6b,5}$=9.51 Hz, 1H, H-6b), 1.81 (dd, $J_{10,8}$=7.12, 1.42 Hz, 3H, H-10);

$^{13}$C NMR (151 MHz, methanol-$d_4$) δ 173.81 (C-7), 171.28 (C11), 153.80 (C-3), 131.16 (C-9), 124.29 (C-8), 111.41 (C-4), 100.95 (C-1"), 94.96 (C-1), 78.38 (C5"), 77.99 (C-3"), 74.83 (C-2"), 71.49 (C-4"), 62.73 (C-6"), 52.05 (C-1'), 41.12 (C-6), 32.23 (C-5), 13.52 (C-10);

HRMS (ESI−) m/z 403.1251 (calcd for $C_{17}H_{23}O_{11}$ 403.1246).

Example 13—Synthesis of GS14

Oleoside 7-(3-Hydroxyphenethyl) ester, also (2S,4S,E)-3-ethylidene-4-(2-(3-hydroxyphenethoxy)-2-oxoethyl)-2-{[(2R,3S,4R,5R,6S)-3,4,5-trihydroxy-6-(hydroxymethyl)tetrahydro-2H-pyran-2-yl]oxy}-3,4-dihydro-2H-pyran-5-carboxylic acid (GS14), was obtained in 39% yield according to the procedure of Example 2.

Characterization of GS14.

$^1$H NMR (600 MHz, methanol—$d_4$) δ 7.54 (s, 1H, H-3), 7.13 (t, $J_{7',6',8'}$=7.84 Hz, 1H, H-7'), 6.73 (d, $J_{8',7'}$=7.68 Hz, 1H, H-8'), 6.70 (t, $J_{4',6',8'}$=2.03 Hz, 1H, H-4'), 6.66 (dd, $J_{6',7'}$=8.10, $J_{6',4',8'}$=2.45 Hz, 1H, H-6'), 6.11 (q, $J_{8,10}$=7.00 Hz, 1H, H-8), 5.93 (s, 1H, H-1), 4.83 (d, $J_{1",2"}$=7.76 Hz, 1H, H-1"), 4.28 (dt, $J_{1a',1b}$=10.77 Hz, $J_{1a',2'}$=7.02 Hz, 1H, H-1a'), 4.19 (dt, $J_{1b',1a}$=10.77 Hz, $J_{1b',2'}$=7.06 Hz, 1H, H-1b'), 4.00 (dd, $J_{5,6b}$=9.16, $J_{5,6a}$=4.46 Hz, 1H, H-5), 3.92 (dd, $J_{6a",6b"}$=12.25, $J_{6a",5"}$=1.90 Hz, 1H, H-6a"), 3.71 (dd, $J_{6b",6a"}$=12.25, $J_{6b",5"}$=5.40 Hz, 1H, H-6b"), 3.46-3.43 (m, 1H, H-3"), 3.39-3.37 (m, 1H, H-5"), 3.36-3.35 (m, 1H, H-4"), 3.35-3.34 (m, 1H, H-2"), 2.88 (t, $J_{2',1a',1b}$=7.02 Hz, 2H, H-2'), 2.78 (dd, $J_{6a,6b}$=14.02, $J_{6a,5}$=4.53 Hz, 1H, H-6a), 2.48 (dd, $J_{6b,6a}$=14.02, $J_{6b,5}$=9.32 Hz, 1H, H-6b), 1.69 (dd, $J_{10,8}$=7.09, $J_{10,1}$=1.25 Hz, 3H, H-10);

$^{13}$C NMR (151 MHz, methanol—$d_4$): δ 173.24 (C-7), 170.00 (C-11), 158.48 (C-5'), 155.10 (C-3), 140.75 (C-3'), 130.67 (C-9), 130.51 (C-7'), 124.71 (C-8), 121.24 (C-8'), 116.81 (C-4'), 114.48 (C-6'), 109.68 (C-4), 100.91 (C-1"), 95.16 (C-1), 78.37 (C-5"), 77.94 (C-3"), 74.77 (C-2"), 71.49 (C-4"), 66.49 (C-1'), 62.74 (C-6"), 41.21 (C-6), 35.94 (C-2'), 31.82 (C-5), 13.52 (C-10);

Example 14—Synthesis of GS15

Oleoside 7-hexadecanyl ester, also (2S,4S,E)-3-ethylidene-4-(2-(hexadecyloxy)-2-oxoethyl)-2-{[(2R,3S,4R,5R,6S)-3,4,5-trihydroxy-6-(hydroxymethyl)tetrahydro-2H-pyran-2-yl]oxy}-3,4-dihydro-2H-pyran-5-carboxylic acid (G15), was obtained in 38% yield according to the procedure of Example 2.

Characterization of GS15.

$^1$H NMR (600 MHz, methanol—d$_4$): δ 7.35 (s, 1H, H-3), 6.09 (q, $J_{8,10}$=7.22 Hz, 1H, H-8), 5.87 (s, 1H, H-1), 4.83 (d, $J_{1",2"}$=8.30 Hz, 1H, H-1"), 4.10-4.08 (m, 1H, H-1a'), 4.08-4.06 (m, 1H, H-5), 4.00 (dt, $J_{1b',1a'}$=10.75 Hz, $J_{1b',2'}$=6.77 Hz, 1H, H-1b'), 3.91 (dd, $J_{6a",6b"}$=12.09, $J_{6a",5"}$=1.19 Hz, 1H, H-6a"), 3.72 (dd, $J_{6b",6a"}$=12.09, $J_{6b",5"}$=5.18 Hz, 1H, H-6b"), 3.45-3.43 (m, 1H, H-3"), 3.35-3.34 (m, 2H, H-4"/H-5"), 3.32-3.31 (m, 1H, H-2"), 2.90 (dd, $J_{6a,6b}$=13.96, $J_{6a,5}$=4.16 Hz, 1H, H-6a), 2.44 (dd, $J_{6b,6a}$=14.03, $J_{6b,5}$=9.90 Hz, 1H, H-6b), 1.76 (dd, $J_{10,8}$=7.06, $J_{10,1}$=1.01 Hz, 3H, H-10), 1.66 (quint, $J_{2',1b',3'}$=7.20 Hz, 2H, H-2'), 1.39-1.36 (m, 2H, H-3'), 1.31 (s, 24H, H-4'-15'), 0.93 (t, $J_{16',15'}$=7.17 Hz, 3H, H-16');

$^{13}$C NMR (151 MHz, methanol—d$_4$): δ 173.80 (C-7), 173.26 (C-11), 151.86 (C-3), 131.90 (C-9), 123.61 (C-8), 114.06 (C-4), 100.90 (C-1"), 94.71 (C-1), 78.34 (C-5"), 77.98 (C-3"), 74.87 (C-2"), 71.59 (C-4"), 65.77 (C-1'), 62.84 (C-6"), 41.46 (C-6), 33.04 (C-14'), 32.75 (C-5), 30.75 (C-6"-12'), 30.63 (C-5'), 30.43 (C-4'), 30.41 (C-13'), 29.71 (C-2'), 27.01 (C-3'), 23.70 (C-15'), 14.40 (C-16'), 13.68 (C-10).

Example 15—General Procedure for the Synthesis of EDA Derivatives

To an aqueous HOAC/NaOAc 0.05M pH=5 (5 mL) buffer solution, a 7-oleoside ester or thioester GS3-GS15 (1 equiv) and β-glucosidase (17.46 units/mg, 1 equiv) were added and the resulting mixture was stirred at 37° C. for 3 h. After completion of the reaction, the mixture washed with CH2Cl2 (3×5 mL), the combined organic extracts were dried (anhydrous Na2SO4) and vacuum-evaporated. The residue was purified by flash chromatography (silica gel) using a mixture of CH2Cl2/MeOH, 100→95:5 v/v, to obtain the corresponding EDA derivative.

Example 16—Synthesis of GS16

EDA methyl ester, also (3S,4E)-4-Formyl-3-(2-oxoethyl) hex-4-enoic acid methyl ester (GS16), was prepared in 39% yield from GS12 according to the procedure of Example 15.

Characterization of GS16.

$^1$H NMR (600 MHz, CDCl$_3$) δ 9.67 (brs, 1H, H-3), 9.29 (d, $J_{1,5}$=1.97 Hz, 1H, H-1), 6.71 (q, $J_{8,10}$=7.04 Hz, 1H, H-8), 3.69-3.64 (m, 1H, H-5), 3.63 (s, 3H, H-1'), 3.02 (ddd, $J_{4a,4b}$=18.12, $J_{4a,4b}$=8.42, $J_{4a,3}$=1.19 Hz, 1H, H-4a), 2.83 (dd, $J_{4b,4a}$=18.30, $J_{4b,5}$=5.74 Hz, 1H, H-4b), 2.75 (dd, $J_{6a,6b}$=16.11, $J_{6a,5}$=8.57 Hz, 1H, H6a), 2.66 (dd, $J_{6b,6a}$=16.11, $J_{6b,5}$=6.47 Hz, 1H, H-6b), 2.13 (d, $J_{10,8}$=7.09 Hz, 3H, H-10);

$^{13}$C NMR (151 MHz, CDCl$_3$) δ 200.47 (C-3), 195.21 (C-1), 154.34 (C-8), 51.71 (C-1'), 46.44 (C-4), 36.83 (C6), 27.44 (C-5), 15.38 (C-10);

HRMS (ESI+) m/z 221.0781 (calcd for C$_{10}$H$_{14}$O$_4$Na 221.0784).

Example 17—Synthesis of GS17

Oleacein, also (3S,4E)-4-formyl-3-(2-oxoethyl)-4-hexenoic acid 2-(3,4-dihydroxyphenyl)ethyl ester (GS17), was prepared in 30% yield from GS6 according to the procedure of Example 15.

Characterization of GS17.

$^1$H NMR (600 MHz, CDCl$_3$) δ 9.65 (brs, 1H, H-3), 9.21 (d, $J_{1,5}$=1.88 Hz, 1H, H-1), 6.79 (d, $J_{7',8'}$=8.05 Hz, 1H, H-7'), 6.72 (d, $J_{4',8'}$=1.95 Hz, 1H, H-4'), 6.67 (q, $J_{8,10}$=7.12 Hz, 1H, H-8), 6.61 (dd, $J_{8',7'}$=8.12, $J_{8',4'}$=1.94 Hz, 1H, H-8'), 4.25 (dt, $J_{1a',1b'}$=10.92, $J_{1a',2'}$=6.51 Hz, 1H, H-1a'), 4.18 (dt, $J_{1b',1a'}$=10.92, $J_{1b',2'}$=6.35 Hz, 1H, H-1b'), 3.66-3.61 (m, 1H, H-5), 2.96 (ddd, $J_{4a,4b}$=8.20, $J_{4a,5}$=8.18, $J_{4a,3}$=1.19 Hz, 1H, H-4a), 2.80-2.78 (m, 1H, H-4b), 2.78 (t, $J_{2',1'}$=6.19 Hz, 2H, H-2'), 2.75 (dd, $J_{6a,6b}$=15.59, $J_{6a,5}$=8.73 Hz, 1H, H-6a), 2.63 (dd, $J_{6b,6a}$=15.59, $J_{6b,5}$=6.53 Hz, 1H, H-6b), 2.06 (d, $J_{10,8}$=7.07 Hz, 3H, H-10);

$^{13}$C NMR (151 MHz, CDCl$_3$) δ 201.01 (C-3), 195.85 (C-1), 172.00 (C-7), 155.09 (C-8), 143.57 (C-5'), 143.41 (C-9), 142.90 (C-6'), 130.75 (C-3'), 121.46 (C-8'), 116.34 (C-4'), 115.43 (C-7'), 65.33 (C-1'), 46.44 (C-4), 37.14 (C-6), 34.40 (C-2'), 27.37 (C-5), 15.42 (C-10);

HRMS (ESI+) m/z 343.1150 (calcd for C$_{17}$H$_{20}$O$_6$Na 343.1152).

Example 18—Synthesis of GS19

Oleocanthal, also (3S,4E)-4-formyl-3-(2-oxoethyl)-4-hexenoic acid 2-(4-hydroxyphenyl)ethyl ester (GS19), was prepared from GS7 in 33% yield according to the procedure of Example 15.

Characterization of GS19.

$^1$H NMR (600 MHz, CDCl$_3$) δ 9.62 (brs, 1H, H-3), 9.23 (d, $J_{1,5}$=1.97 Hz, 1H, H-1), 7.04 (d, $J_{4',5'/8',7'}$=8.42 Hz, 2H, H-4'/H-8'), 6.76 (d, $J_{5',4'/7',8'}$=8.45 Hz, 2H, H-5'/H-7'), 6.65 (q, $J_{8,10}$=7.08 Hz, 1H, H-8), 4.24 (dt, $J_{1a',1b'}$=10.86, $J_{1a',2'}$=6.99 Hz, 1H, H-1a'), 4.20 (dt, $J_{1b',1a'}$=10.77, $J_{1b',2'}$=6.97 Hz, 1H, H-1b'), 3.63-3.58 (m, 1H, H-5), 2.99 (ddd, $J_{4a,4b}$=18.26, $J_{4a,5}$=8.61, $J_{4a,3}$=1.16 Hz, 1H, H-4a), 2.83 (t, $J_{2',1'}$=6.92 Hz, 2H, H-2'), 2.75 (dd, $J_{4b,4a}$=18.33, $J_{4b,5}$=5.64 Hz, 1H, H-4b), 2.70 (dd, $J_{6a,6b}$=15.87, $J_{6a,5}$=8.26 Hz, 1H, H-6a), 2.63 (dd, $J_{6b,6a}$=15.91, $J_{6b,5}$=6.66 Hz, 1H, H-6b), 2.07 (d, $J_{10,8}$=7.06 Hz, 3H, H-10);

$^{13}$C NMR (151 MHz, CDCl$_3$) δ 200.62 (C-3), 195.32 (C-1), 172.13 (C-7), 154.64 (C-6'), 154.45 (C-8), 143.49 (C-9), 130.15 (C-3'), 129.82 (C-4'/C-8'), 115.55 (C-5'/C-7'), 65.34 (C-1'), 46.36 (C-4), 37.07 (C-6), 34.32 (C-2'), 27.45 (C-5), 15.35 (C-10);

HRMS (ESI+) m/z 327.1200 (calcd for C$_{17}$H$_{20}$O$_5$Na 327.1203).

Example 19—Synthesis of GS20

EDA 3-hydroxyphenethyl ester, also (3S,4E)-3-(2-oxoethyl)-4-hexenoic acid 3-hydroxyphenethyl ester (GS20), was prepared in 33% yield from GS14 according to the procedure of Example 15.

Characterization of G20.

$^1$H NMR (600 MHz, CDCl$_3$) δ 9.63 (brs, 1H, H-3), 9.21 (d, $J_{1,5}$=1.68 Hz, 1H, H-1), 7.16 (t, $J_{7,6',8'}$=7.80 Hz, 1H, H-7'), 6.73-6.72 (m, 1H, H-8'), 6.72-6.71 (m, 2H, H-6'), 6.68 (brs, 1H, H-4'), 6.65 (q, $J_{8,10}$=7.02 Hz, 1H, H-8), 4.28 (dt, $J_{1a',1b'}$=10.84, $J_{1a',2'}$=6.75 Hz, 1H, H-1a'), 4.22 (dt, =10.84, $J_{1b',2'}$=6.56 Hz, 1H, H-1b'), 3.64-3.60 (m, 1H, H-5), 2.97 (ddd, $J_{4a,4b}$=18.35, $J_{4a,5}$=8.35, $J_{4a,3}$=0.86 Hz, 1H, H-4a), 2.85 (t, $J_{2',1'}$=6.76 Hz, 2H, H-2'), 2.79 (dd, $J_{4b,4a}$=18.35, $J_{4b,5}$=5.68 Hz, 1H, H-4b), 2.73 (dd, $J_{6a,6b}$=15.76, $J_{6a,5}$=8.73 Hz, 1H, H-6a), 2.63 (dd, $J_{6b,6a}$=15.76, $J_{6b,5}$=6.45 Hz, 1H, H-6b), 2.05 (d, $J_{10,8}$=7.04 Hz, 3H, H-10);
$^{13}$C NMR (151 MHz, CDCl$_3$) δ 200.98 (C-3), 195.75 (C-1), 172.11 (C-7), 156.13 (C-5'), 155.11 (C-8), 143.26 (C-9), 139.68 (C-3'), 129.84 (C-7'), 121.09 (C-8'), 116.14 (C-4'), 113.83 (C-6'), 65.02 (C-1'), 46.33 (C-4), 37.05 (C-6), 34.90 (C-2'), 27.31 (C-5), 15.40 (C-10).

Example 20—Synthesis of GS21

EDA 2-phenylethyl ester, also (3S,4E)-4-formyl-3-(2-oxoethyl)-4-hexenoic acid 2-phenylethyl ester (GS21), was prepared in 31.5% yield from GS4 according to the procedure of Example 15.
Characterization of G21.
$^1$H NMR (600 MHz, CDCl$_3$) δ 9.62 (brs, 1H, H-3), 9.23 (d, $J_{1,5}$=1.96 Hz, 1H, H-1), 7.30-7.28 (m, 2H, H-7'/H-5'), 7.23-7.21 (m, 1H, H-6'), 7.19-7.18 (m, 2H, H-4'/H-8'), 6.62 (q, $J_{8,10}$=6.95 Hz, 1H, H-8), 4.29 (dt, $J_{1a',1b'}$=10.87, $J_{1a',2}$=7.03 Hz, 1H, H-1a'), 4.26 (dt, $J_{1b',1a'}$=10.87, $J_{1b',2}$=6.94 Hz, 1H, H-1b'), 3.63-3.58 (m, 1H, H-5), 2.99 (ddd, $J_{4a,4b}$=18.28, $J_{4a,5}$=8.64, $J_{4a,3}$=1.29 Hz, 1H, H-4a), 2.91 (t, $J_{2',1'}$=6.97 Hz, 2H, H-2'), 2.75 (ddd, $J_{4b,4a}$=18.29, $J_{4b,5}$=5.45, $J_{4b,3}$=0.86 Hz 1H, H-4b), 2.70 (dd, $J_{6a,6b}$=15.87, $J_{6a,5}$=8.39 Hz, 1H, H-6a), 2.63 (dd, $J_{6b,6a}$=15.85, $J_{6b,5}$=6.58 Hz, 1H, H-6b), 2.07 (d, $J_{10,8}$=7.05 Hz, 3H, H-10);
$^{13}$C NMR (151 MHz, CDCl$_3$) δ 200.43 (C-3), 195.16 (C-1), 172.01 (C-7), 154.21 (C-8), 143.49 (C-9), 137.86 (C-3'), 129.01 (C-4'/C-8'), 128.65 (C-5'/C7'), 126.72 (C-6'), 65.06 (C-1'), 46.35 (C-4), 37.02 (C-6), 35.19 (C-2'), 27.43 (C-5), 15.33 (C-10);
HRMS (ESI+) m/z 311.1253 (calcd for C$_{17}$H$_{20}$O$_4$Na 311.1254).

Example 21—Synthesis of GS22

EDA 2-cyclohexylethyl ester, also 2-cyclohexylethyl (S,E)-4-formyl-3-(2-oxoethyl)hex-4-enoate (GS22), was prepared in 29% yield from GS5 according to the procedure in Example 15.
Characterization of G22.
$^1$H NMR (600 MHz, CDCl$_3$) δ 9.62 (brs, 1H, H-3), 9.23 (d, $J_{1,5}$=1.96 Hz, 1H, H-1), 7.30-7.28 (m, 2H, H-7'/H-5'), 7.23-7.21 (m, 1H, H-6'), 7.19-7.18 (m, 2H, H-4'/H-8'), 6.62 (q, $J_{8,10}$=6.95 Hz, 1H, H-8), 4.29 (dt, $J_{1a',1b'}$=10.87, $J_{1a',2}$=7.03 Hz, 1H, H-1a'), 4.26 (dt, $J_{1b',1a'}$=10.87, $J_{1b',2}$=6.94 Hz, 1H, H-1b'), 3.63-3.58 (m, 1H, H-5), 2.99 (ddd, $J_{4a,4b}$=18.28, $J_{4a,5}$=8.64, $J_{4a,3}$=1.29 Hz, 1H, H-4a), 2.91 (t, $J_{2',1'}$=6.97 Hz, 2H, H-2'), 2.75 (ddd, $J_{4b,4a}$=18.29, $J_{4b,5}$=5.45, $J_{4b,3}$=0.86 Hz 1H, H-4b), 2.70 (dd, $J_{6a,6b}$=15.87, $J_{6a,5}$=8.39 Hz, 1H, H-6a), 2.63 (dd, $J_{6b,6a}$=15.85, $J_{6b,5}$=6.58 Hz, 1H, H-6b), 2.07 (d, $J_{10,8}$=7.05 Hz, 3H, H-10);
$^{13}$C NMR (151 MHz, CDCl$_3$) δ 200.43 (C-3), 195.16 (C-1), 172.01 (C-7), 154.21 (C-8), 143.49 (C-9), 137.86 (C-3'), 129.01 (C-4'/C-8'), 128.65 (C-5'/C7'), 126.72 (C-6'), 65.06 (C-1'), 46.35 (C-4), 37.02 (C-6), 35.19 (C-2'), 27.43 (C-5), 15.33 (C-10);
HRMS (ESI+) m/z 311.1253 (calcd for C$_{17}$H$_{20}$O$_4$Na 311.1254).

Example 22—Synthesis of GS23

EDA adamantan-1-ylmethyl ester, also (3S,4E)-4-formyl-3-(2-oxoethyl)hex-4-enoic acid adamantan-1-ylmethyl ester (GS23), was prepared in 28% yield from GS3 according to the procedure of Example 15.

Characterization of G23.
$^1$H NMR (600 MHz, CDCl$_3$) δ 9.67 (brs, 1H, H-3), 9.29 (d, $J_{1,5}$=1.96 Hz, 1H, H-1), 6.70 (q, $J_{8,10}$=7.10 Hz, 1H, H-8), 3.68-3.65 (m, 1H, H-5), 3.64-3.59 (m, 2H, H-1'), 3.04 (ddd, $J_{4a,4b}$=18.22, $J_{4a,5}$=8.74 and $J_{4a,3}$=1.21 Hz, 1H, H-4a), 2.81 (dd, $J_{4b,4a}$=18.22 and $J_{4b,5}$=5.47 Hz, 1H, H-4b), 2.74 (dd, $J_{6a,6b}$=15.93 and $J_{6a,5}$=8.28 Hz, 1H, H-6a), 2.68 (dd, $J_{6b,6a}$=15.93 and $J_{6b,5}$=6.64 Hz, 1H, H-6b), 2.12 (d, $J_{10,8}$=7.05 Hz, 3H, H-10), 1.96 (b, 3H, H-4'/H-6'/H-8'), 1.73-1.71 (m, 3H, H-5a'/H-7a'/H-10a'), 1.64-1.62 (m, 3H, H-5b'/H-7b'/H-10b'), 1.48 (m, 6H, H-3'/H-9'/H-11');
$^{13}$C NMR (151 MHz, CDCl$_3$) δ 200.52 (C-3), 195.22 (C-1), 172.37 (C-7), 154.32 (C-8), 143.66 (C-9), 74.31 (C-1'), 46.46 (C-4), 39.39 (C-3'/C-9'/C-11'), 37.08 (C-5'/C-7'/C-10'), 37.02 (C-6), 33.24 (C-2'), 28.16 (C-4'/C-6'/C-8'), 27.55 (C-5), 15.42 (C-10);
HRMS (ESI+) m/z 355.1877 (calcd for C$_{20}$H$_{28}$O$_4$Na, 355.1880).

Example 23—Synthesis of GS24

EDA 2-phenoxyethyl ester or (3S,4E)-4-formyl-3-(2-oxoethyl)-4-hexenoic acid 2-phenoxyethyl ester (GS24), was prepared in 31% yield from GS10 according to the procedure of Example 15.
Characterization of G24.
$^1$H NMR (600 MHz, CDCl$_3$) δ 9.65 (brs, 1H, H-3), 9.26 (d, $J_{1,5}$=2.00 Hz, 1H, H-1), 7.30-7.27 (m, 2H, H-5'/H-7'), 6.98-6.95 (m, 1H, H-6'), 6.89-6.88 (m, 2H, H-4'/H-8'), 6.66 (q, $J_{8,10}$=7.04 Hz, 1H, H-8), 4.39 (td, $J_{1',2'}$, =4.68, $J_{1a',1b'}$=1.59 Hz, 2H, H-1'), 4.14 (t, $J_{2',1'}$=4.68 Hz, 2H, H-2'), 3.69-3.64 (m, 1H, H-5), 3.02 (ddd, $J_{4a,4b}$=18.28, $J_{4a,5}$=8.67, $J_{4a,3}$=1.19 Hz, 1H, H-4a), 2.83 (ddd, $J_{4b,4a}$=18.28, $J_{4b,5}$=5.56, $J_{4b,3}$=0.76 Hz 1H, H-4b), 2.79 (dd, $J_{6a,6b}$=16.02, $J_{6a,5}$=8.64 Hz, 1H, H-6a), 2.70 (dd, $J_{6b,6a}$=16.02, $J_{6b,5}$=6.40 Hz, 1H, H-6b), 2.07 (d, $J_{10,8}$=7.03 Hz, 3H, H-10);
$^{13}$C NMR (151 MHz, CDCl$_3$) δ 200.40 (C-3), 195.16 (C-1), 172.02 (C-7), 158.58 (C-3'), 154.29 (C-8), 143.44 (C-9), 129.70 (C-5'/C-7'), 121.40 (C-6'), 114.74 (C-4'/C-8'), 65.89 (C-2'), 63.04 (C-1'), 46.43 (C-4), 36.95 (C-6), 27.43 (C-5), 15.38 (C-10).

Example 24—Synthesis of GS25

EDA (1H-indol-2-yl)methyl ester, also (3S,4E)-4-formyl-3-(2-oxoethyl)-4-hexenoic acid (1H-indol-2-yl)methyl ester (GS25), was prepared in 25% yield from GS8 according to the procedure of Example 15.
Characterization of G25.
$^1$H NMR (600 MHz, CDCl$_3$) δ 9.65 (brs, 1H, H-3), 9.21 (d, $J_{1,5}$=1.94 Hz, 1H, H-1), 8.53 (br, 1H, H-3'), 7.59 (d, $J_{8',7'}$=8.18 Hz, 1H, H-8'), 7.35 (d, $J_{5',6'}$=8.13 Hz, 1H, H-5'), 7.22 (dt, =7.55 Hz, $J_{6',8'}$=0.98 Hz, 1H, H-6'), 7.11 (t, $J_{7',6',8}$=7.45 Hz, 1H, H-7'), 6.52 (q, $J_{8,10}$=7.09 Hz, 1H, H-8), 6.50 (s, 1H, H-10'), 5.19 (d, $J_{1',10'}$=1.25 Hz, 2H, H-1'), 3.69-3.64 (m, 1H, H-5), 2.98 (ddd, $J_{4a,4b}$=18.38, $J_{4a,5}$=8.13 and $J_{4a,3}$=0.76 Hz, 1H, H-4a), 2.83 (dd, $J_{4b,4a}$=18.43, $J_{4b,5}$=5.87 Hz, 1H, H-4b), 2.79 (dd, $J_{6a,6b}$=15.46 and $J_{6a,5}$=8.88 Hz, 1H, H-6a), 2.69 (dd, $J_{6b,6a}$=15.55 and $J_{6b,5}$=6.36 Hz, 1H, H-6b), 1.98 (d, $J_{10,8}$=7.12 Hz, 3H, H-10);
$^{13}$C NMR (151 MHz, CDCl$_3$) δ 200.32 (C-3), 195.15 (C-1), 173.17 (C-7), 154.32 (C-8), 143.22 (C-9), 136.72 (C-4'), 132.95 (C-2'), 127.73 (C-9'), 123.01 (C-6'), 121.08 (C-8'), 120.21 (C-7'), 111.20 (C-5'), 104.14 (C-10'), 59.91 (C-1'), 46.48 (C-4), 37.13 (C-6), 27.56 (C-5), 15.23 (C-10).

Example 25—Synthesis of GS26

EDA hexadecyl ester, also (3S,4E)-4-formyl-3-(2-oxoethyl)-4-hexenoic acid hexadecyl ester (GS26), was prepared in 32% yield from GS15 according to the procedure of Example 15.
Characterization of G26.
$^1$H NMR (600 MHz, CDCl$_3$) δ 9.67 (brs, 1H, H-3), 9.29 (d, $J_{1,5}$=1.92 Hz, 1H, H-1), 6.70 (q, $J_{8,10}$=7.02 Hz, 1H, H-8), 4.03 (td, $J_{1',2a'}$=6.77, $J_{1',2b'}$=2.30 Hz, 2H, H-1'), 3.69-3.65 (m, 1H, H-5), 3.03 (ddd, $J_{4a,4b}$=18.20, $J_{4a,4b}$=8.59, $J_{4a,3}$=1.08 Hz, 1H, H-4a), 2.82 (dd, $J_{4b,4a}$=18.20, $J_{4b,5}$=5.38 Hz, 1H, H-4b), 2.73 (dd, $J_{6a,6b}$=15.88, $J_{6a,5}$=8.48 Hz, 1H, H6a), 2.65 (dd, $J_{6b,6a}$=15.88, $J_{6b,5}$=6.61 Hz, 1H, H-6b), 2.13 (d, $J_{10,8}$=7.07 Hz, 3H, H-10), 1.59-1.55 (m, 2H, H-2'), 1.31-1.28 (m, 2H, H-3'), 1.26 (s, 24H, H-4'-15'), 0.89 (t, $J_{16',15'}$=6.94 Hz, 3H, H-16')

Example 26—Synthesis of GS27

EDA S-phenethyl thioester, also S-phenethyl (3S,4E)-4-formyl-3-(2-oxoethyl)hex-4-enethioate (GS27), was prepared in 41% yield from GS11 according to the procedure of Example 15.
Characterization of G27.
$^1$H NMR (600 MHz, CDCl$_3$) δ 9.65 (brs, 1H, H-3), 9.27 (d, $J_{1,5}$=1.96 Hz, 1H, H-1), 7.30-7.28 (m, 2H, H-5'/H-7'), 7.23-7.20 (m, 1H, H-6'), 7.20-7.18 (m, 2H, H-4'/H-8'), 6.67 (q, $J_{8,10}$=7.04 Hz, 1H, H-8), 3.74-3.68 (m, 1H, H-5), 3.10 (td, $J_{1',2a'}$=7.68, $J_{1',2b'}$=1.33 Hz, 2H, H-1'), 3.03 (ddd, $J_{4a,4b}$=18.35, $J_{4a,5}$=8.78, $J_{4a,3}$=1.10 Hz, 1H, H-4a), 2.97 (dd, $J_{6a,6b}$=15.39, $J_{6a,5}$=8.42 Hz, 1H, H-6a), 2.87 (dd, $J_{6b,6a}$=15.39, $J_{6b,5}$=6.47 Hz, 1H, H-6b), 2.76 (ddd, $J_{4b,4a}$=18.35, $J_{4b,5}$=5.37, $J_{4b,3}$=0.57 Hz, 1H, H-4b), 2.09 (d, $J_{10,8}$=7.06 Hz, 3H, H-10);
$^{13}$C NMR (151 MHz, CDCl$_3$) δ 200.29 (C-3), 197.64 (C-7), 195.19 (C-1), 154.40 (C-8), 143.12 (C-9), 139.95 (C-3'), 128.74 (C-4'/C-8'), 128.64 (C-5'/C-7'), 126.71 (C-6'), 46.19 (C-4/C-6), 35.91 (C-2'), 30.41 (C-1'), 27.98 (C-5), 15.41 (C-10).

Example 27—Synthesis of GS28

EDA 3-(methylthio)propyl ester or (3S,4E)-4-formyl-3-(2-oxoethyl)-4-hexenoic acid 3-(methylthio)propyl ester (GS28), was prepared in 28% yield from GS9 according to the procedure of Example 15.
Characterization of G28.
$^1$H NMR (600 MHz, CDCl$_3$) δ 9.67 (brs, 1H, H-3), 9.29 (d, $J_{1,5}$=1.90 Hz, 1H, H-1), 6.71 (q, $J_{8,10}$=7.11 Hz, 1H, H-8), 4.15-4.12 (m, 1H, H-1a'), 4.12-4.09 (m, 1H, H-1b'), 3.68-3.63 (m, 1H, H-5), 3.02 (ddd, $J_{4a,4b}$=18.24, $J_{4a,5}$=8.52, $J_{4a,3}$=0.95 Hz, 1H, H-4a), 2.82 (dd, $J_{4b,4a}$=18.24, $J_{4b,5}$=5.60 Hz, 1H, H-4b), 2.74 (dd, $J_{6a,6b}$=16.03, $J_{6a,5}$=8.63 Hz, 1H, H-6a), 2.66 (dd, $J_{6b,6a}$=16.03, $J_{6b,5}$=6.46 Hz, 1H, H-6b), 2.53 (t, $J_{3',2',1'}$=7.26 Hz, 1H, H-3'), 2.13 (d, $J_{10,8}$=7.08 Hz, 3H, H-10), 2.09 (s, 3H, H-5'), 1.90-1.86 (m, 2H, H-2');
$^{13}$C NMR (151 MHz, CDCl$_3$) δ 200.42 (C-3), 195.19 (C-1), 172.07 (C-7), 154.35 (C-8), 143.576 (C-9), 63.22 (C-1'), 46.45 (C-4), 36.95 (C-6), 30.72 (C-3'), 28.26 (C-2'), 27.43 (C-5), 15.64 (C-5'), 15.43 (C-10).

EVALUATION OF BIOLOGICAL ACTIVITY

Example 28—Antioxidant Activity of GS Compounds

The following six assays were used in testing the antioxidant activity of the compounds of the present invention.

1. DPPH Radical Scavenging Assay

The method of assessing the antioxidant capacity through the binding of the stable DPPH. radical was performed for the first time by Brand-Williams et al. in 1995 (Brand-William, W. et al., Lebensm Wiss Technol, 1995, 28: 25-30, "Use of a free radical method to evaluate antioxidant activity"). The method used herein is a variation of the original method and is one of the most characteristic and simple methods for the initial assessment of the antioxidant activity of antioxidant molecules or extracts rich in compounds with antioxidant properties.

Figure 2:
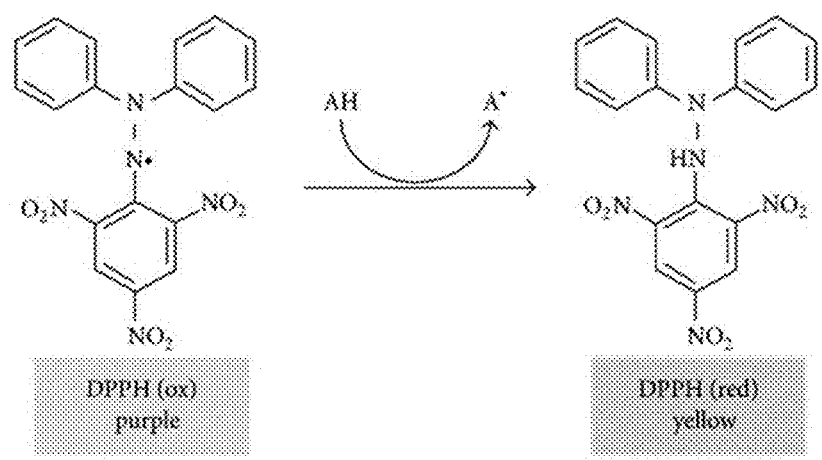
FIG. 2 shows the DPPH radical scavenging assay.

The assessment of antioxidant capacity is based on the interaction of the tested molecules with the stable radical of 2,2-diphenyl-1-picrylydrazyl (DPPH). The DPPH. radical can be inactivated either by the addition of an electron or by a hydrogen atom. It is a stable organic nitrogen radical that is purple in color and absorbs at 517 nm. When a substance with antioxidant activity is added to the radical solution, then 2,2-diphenyl-1-picrylydrazyl (DPPH.) is reduced by the addition of a hydrogen atom (or electron) and converted to 2,2-diphenyl-1-picrylhydrazine (DPPH) which has a yellow color, resulting in reduction to the visual absorption (FIG. 2).

The effects of GS compounds on DPPH radical was evaluated as described previously (Spanou, C et al., Anticancer Research, 2007, 27: 3403-3410). Briefly, the assay was carried out in 1 mL of methanol containing 100 μM freshly made DPPH in methanol and the tested GS compound at different concentrations. The contents were vigorously mixed, incubated at room temperature in the dark for 20 minutes and the absorbance was read at 517 nm using a Hitachi U-1500 Spectrophotometer (San Jose, USA). In each experiment, the tested extract alone in methanol was used as blank and DPPH alone in methanol was used as control. All experiments were carried out in triplicate. The radical scavenging capacity (RSC) of the tested extracts was expressed as a percentage of DPPH elimination calculated according to the following equation: % RSC=[(absorbance of control−absorbance of GS compound)/absorbance of control]×100.

2. ABTS Radical Cation Scavenging Assay

The method of estimating antioxidant capacity, based on the ability to interact with the ABTS.+ radical cation was first performed by Miller et al. in 1993 (Miller, Nicholas et al., Clinical Science, 1993, 84: 407-412, "A novel method for measuring the antioxidant capacity and its application to monitoring the antioxidant status in premature neonates"). The mechanism of interaction of the antioxidant agents to be examined with the ABTS.+ radical is similar to that of the DPPH. radical, which can be inactivated either by the addition of an electron or by the addition of a hydrogen atom. However, unlike the DPPH. radical, which is a stable radical from the beginning, the ABTS.+ radical must be produced by the oxidation of ABTS. Thus, in order to estimate the antioxidant capacity of a substance, the formation of the ABTS.+ radical must first precede and the addition of the substance to be examined must follow. The addition of the antioxidant agent is performed after the production of the root ABTS.+ to avoid the interaction of the antioxidant agents with the oxidizing agents used for the oxidation of ABTS.

The oxidation of ABTS takes place either through chemical reactions with various reagents or through the action of enzymes such as peroxidases. The ABTS.+ radical from the moment it is formed is stable, has a green color and absorbs at 730 nm. When a substance with antioxidant activity is added to the solution, then the ABTS.+ radical is reduced by the addition of a hydrogen (or electron) atom, resulting in reduced visual absorption.

Figure 3:
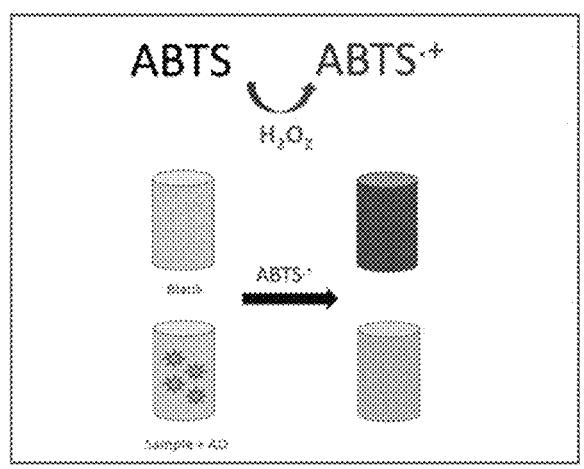
FIG. 3 shows the ABTS radical scavenging assay.

To assess the antioxidant capacity of the samples, the oxidation of ABTS was performed enzymatically through the action of horseradish peroxidase (HRP), in the presence of $H_2O_2$ (FIG. 3)

The anti-oxidant capacity of the GS compounds was evaluated by performing the ABTS assay as previously described (Kouka, Paraskevi et al., Oxid Med Cell Longev. 2019, Article ID 1870965). Briefly, in a total reaction volume of 1 mL in distilled water ($dH_2O$), $ABTS.^+$ (1 mM), $H_2O_2$ (30 µM), and horseradish peroxidase (HRP) (6 µM) in 50 mM phosphate-buffered saline were added. The solution was incubated for 45 min at room temperature (RT) in the dark. Finally, 10 µL of the tested GS compound at various concentrations was added, and the absorbance was monitored on a Hitachi U-1900 radio beam spectrophotometer (serial no. 2023-029; Hitachi Ltd.) at 730 nm. In each experiment, a blank without the HRP was used, while the $ABTS.^+$ radical solution without the extract was used as the control. The RSC percentage of the tested extracts was calculated using the following equation: RSC (%)=[(ODcontrol−ODcompound)/ODcontrol]×100, where ODcontrol and OD sample are the optical density (OD) values of the control and the test sample, respectively.

3. Superoxide Anion Radical Scavenging Assay

Superoxide radicals have been observed to kill cells, inactivate enzymes, and degrade DNA, cell membranes, and polysaccharides. These radicals may also play an important role in the peroxidation of unsaturated fatty acids and possibly other susceptible substances.

Figure 4:
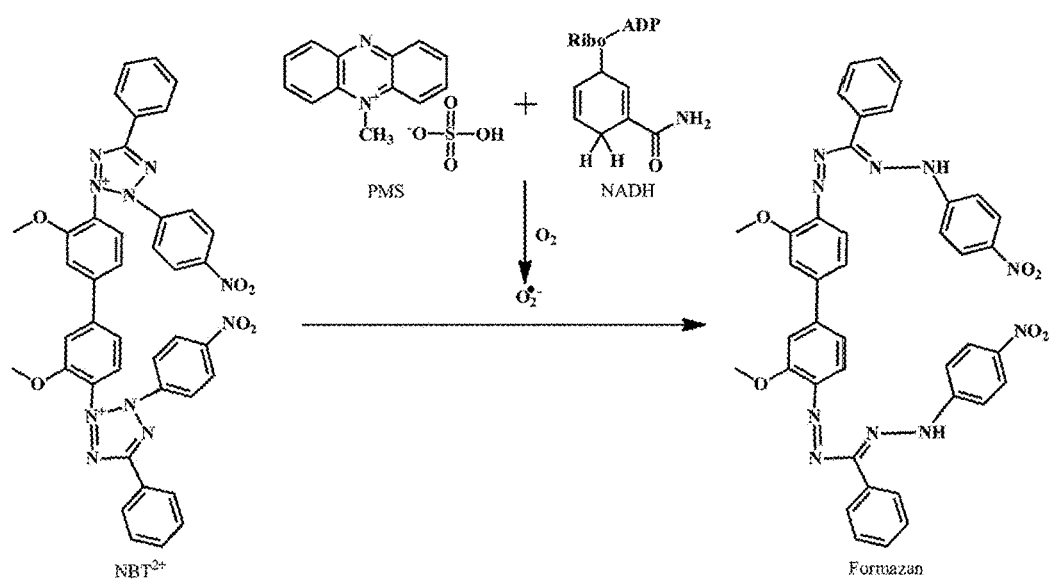
FIG. 4 shows the superoxide anion radical scavenging assay.

Under aerobic conditions, superoxide anion radicals are generated nonenzymatically in a NADH-PMS system by oxidation of nicotinamide adenine nucleotide (NADH) with phenazine methosulphate (PMS) in the presence of dissolved oxygen. (See, Nimse, Satish B. et al., RSC Adv, 2015, 5: 27986, "Free radicals, natural antioxidants, and their reaction mechanisms"). The superoxide anion radical $O2.^-$ reduces the pale yellow colored nitroblue tetrazolium cation ($NBT^{2+}$) to a blue colored formazan dye, which is measured spectrophotometrically at 560 nm. The decrease of absorbance at 560 nm with antioxidant indicates the consumption of $O2.^+$ in the reaction mixture (FIG. 4).

The superoxide anion radical scavenging activity of each GS compound was determined using the nitro-blue tetrazolium (NBT) reduction method (Cos, Paul et al., J Nat Prod. 1998; 61(1): 71-76). The results were calculated as the percentage of inhibition according to the following formula: I (%)=100 [1−(S−SB)/(C−CB)] Where S, SB, C, and CB are the absorbance of the sample, the blank sample, the control, and the blank control, respectively.

4. Deoxyribose Degradation Assay

The hydroxyl radical (OH.) is an extremely reactive in biological systems and has been implicated as highly damaging species in free radical pathology, capable of damaging biomolecules of the living cells. These radical combines with nucleotides in DNA and cause strand breakage leading to carcinogenesis, mutagenesis and cytotoxicity. Hydroxyl radical (OH.) scavenging capacity of an extract is directly related to its antioxidant activity.

Figure 5:
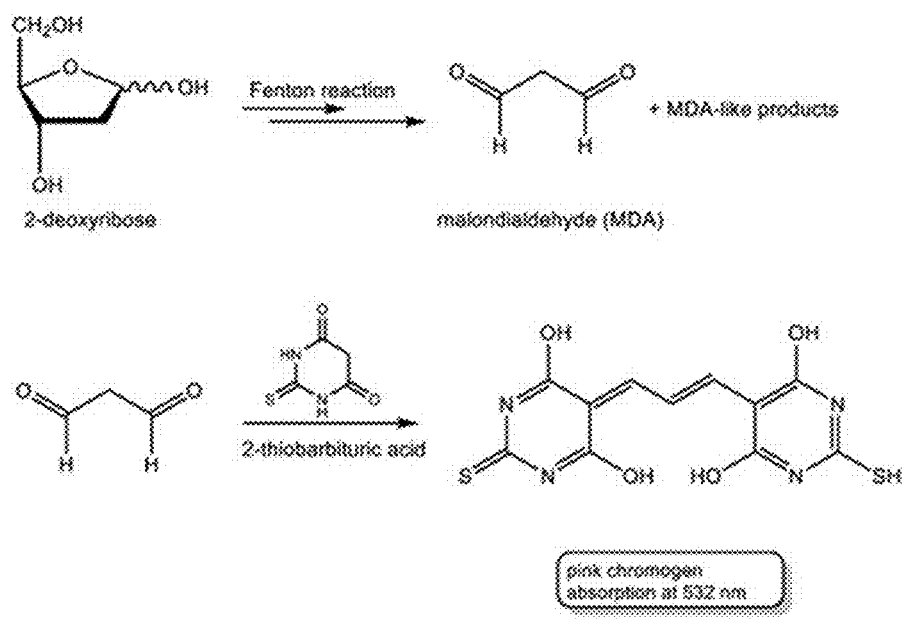
FIG. 5 shows the deoxyribose degradation assay.

The effect of extracts on hydroxyl radicals was assayed by using the deoxyribose method. 2-Deoxyribose is degraded on exposure to hydroxyl radicals generated by Fenton's reaction. The ability to neutralize the OH. is estimated as the rate of inhibition of the oxidation of 2-deoxyribose by the OH. (FIG. 5).

The measurement of the hydroxyl radical scavenging activity was evaluated for each of the GS compound by evaluating the pink chromogen absorption at 532 nm by spectrophotometry as described previously (Perjesi, Pal et al., Open Med Chem J., 2011, 5: 61-67

5. Ferric Reducing Antioxidant Power (FRAP) Assay

Reducing power is associated with antioxidant activity and may serve as a significant reflection of the antioxidant activity. Compounds with reducing power indicate that they are electron donors and can reduce the oxidized intermediates of lipid peroxidation processes, so that they can act as primary and secondary antioxidants.

Figure 6:
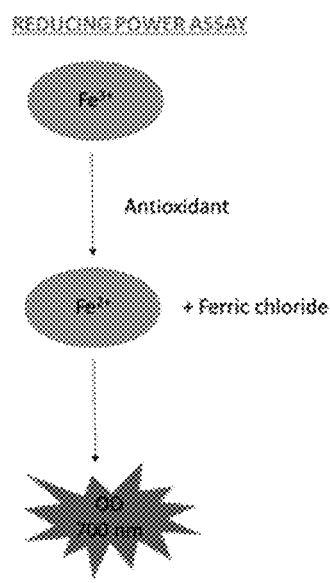
FIG. 6 shows the ferric reducing antioxidant power (FRAP) assay.

In this assay, the yellow color of the test solution changes to various shades of green and blue depending on the reducing power of each compound. Presence of reducers causes the conversion of the Fe3+/ferricyanide complex used in this method to the ferrous form which when it reacts with iron chloride it gives a complex which absorbs at 700 nm. The higher the absorption at 700 nm, the greater the reducing capacity (FIG. 6).

The ferric reducing antioxidant capacity of the GS compounds was investigated by using the potassium ferricyanide-ferric chloride method (Tundis, Rosa et al. LWT—Food Science and Technology, 2013, 53: 370-377). Briefly, 0.2 mL of each of the GS compounds, 2.5 mL of phosphate buffer (0.2 M, pH 6.6), and 2.5 mL of potassium ferricyanide K3Fe(CN)6 (1%) were mixed and incubated at 50° C. for 20 min, to reduce ferricyanide into ferrocyanide. The reaction was stopped by adding 2.5 mL of 10% (w/v) trichloroacetic acid followed by centrifugation at 1000 rpm for 10 min. Finally, 2.5 mL of the upper layer was mixed with 2.5 mL of distilled water and 0.5 mL of FeCl3 (0.1%) and the absorbance was measured at 700 nm.

6. Plasmid Relaxation Assay

Topoisomerases are nuclear enzymes that play essential roles in DNA replication, transcription, chromosome segregation, and recombination. Type I topoisomerases (classified into three distinct subfamilies—Type IA, IB, and IC based on structural considerations) are enzymes which make single-stranded cuts in DNA. DNA topoisomerases are important targets of approved and experimental anti-cancer agents. The protocol described here are of assays used to assess the ability of GS compounds to inhibit topoisomerase Type I activity based on relaxation of supercoiled DNA.

Plasmid DNA is a circular double-stranded DNA molecule that is mainly found in bacteria and has the ability to self-replicate on its own. Bacteria may have one or more copies of plasmid DNA that help them survive adverse conditions, as they usually carry antibiotic resistance genes. Even with the help of plasmids being transferred from bacterium to bacterium, it is possible to transfer information that contributes to their survival.

Figure 7:
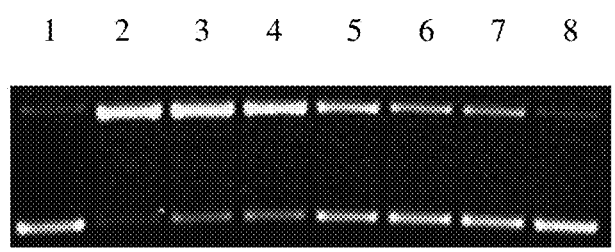
FIG. 7 shows the plasma relaxation assay.

When plasmid DNA runs in an electrophoresis gel it appears mainly in three configurations: (1) The supercoiled conformation, in which the plasmid is intact (without fractures), is its most compact form; (2) The open circular, relaxed conformation, to which it goes when single-stranded fractures are caused. This is caused either from enzymatic or other factors (e.g., free radicals) that have the ability to cause DNA breakage; (3) The linear configuration to which it goes when it has double-stranded fractures. These configurations run at different speeds in an electrophoresis gel. The smaller the configuration, the faster it penetrates the agarose pores. Thus, the supercoiled runs first, the linear second, and the open circular third. The effect of compounds with antioxidant properties to inhibit topoisomerase I activity based on relaxation of supercoiled DNA is shown in FIG. 7.

The ability of GS compounds to inhibit topoisomerase Type I activity was assessed based on the relaxation of supercoiled DNA as previously described (Kouka, Paraskevi et al., Oxid Med Cell Longev. 2019, Article ID 1870965). Briefly, in a total reaction volume of 10 μL, 2 μL of DNA was mixed with PBS and a range of different concentrations of the tested GS compound. The tubes were incubated for 45 min at 37° C. Finally, 3 μL of loading buffer (containing bromophenol blue 0.25%+30% glycerol) was mixed, and the samples were loaded on a 0.8% agarose gel. The samples were run at 70 V for 60 min. Subsequently, the gel was stained with 12.5 μL of ethidium bromide (10 mg/mL) in 250 mL of $dH_2O$ for 30 min. Consequently, the gel was washed with 250 ml of $dH_2O$ for 30 min. Finally, the gels were exposed to UV, the MultiImage Light Cabinet (Alpha Innotech, San Leandro, CA, USA) was used to capture the gel photos, and the results were analyzed with the Alpha View suite. For negative control, DNA was mixed with PBS only, and for positive control, DNA was mixed with both PBS and AAPH. The maximum tested concentrations were mixed with DNA and PBS, without the AAPH, to check the putative effects of the extracts on plasmid DNA.

A total of 25 GS compounds were examined for their anti-oxidant activity. Results of the DPPH Radical Scavenging Assay, ABTS Radical Cation Scavenging Assay, Superoxide Anion Radical Scavenging Assay, Deoxyribose Degradation Assay, Ferric Reducing Antioxidant Power (FRAP) Assay, and Plasmid Relaxation Assay are shown in Table 2 below. Data not statistically significant is notated NS.

TABLE 2

Evaluation of Anti-oxidant Properties of GS Compounds

| Compound | DPPH Radical Scavenging Assay IC50 (μg extract/mL) | ABTS Radical Cation Scavenging Assay IC50 (μg extract/mL) | Superoxide Anion Radical Scavenging Assay IC50 (μg extract/mL) | Deoxyribose Degradation Assay IC50 (μg extract/mL) | Ferric Reducing Power Antioxidant Assay RP0.5AU (μg extract/mL) | Plasmid Relaxation Assay IC50 (μg extract/mL) |
|---|---|---|---|---|---|---|
| GS1 | 13.8 | 20.9 | 40.5 | 80.8 | 35 | 9.91 |
| GS2 | NS | NS | NS | NS | NS | NS |
| GS3 | NS | NS | NS | NS | NS | NS |
| GS4 | NS | NS | NS | NS | NS | NS |
| GS5 | NS | NS | NS | NS | NS | NS |
| GS6 | 5.9 | 8.2 | 23.2 | 41.9 | 36 | 5.94 |
| GS7 | NS | NS | NS | NS | NS | NS |
| GS8 | NS | NS | NS | NS | NS | NS |
| GS9 | NS | NS | NS | NS | NS | NS |
| GS10 | NS | NS | NS | NS | NS | NS |
| GS11 | NS | NS | NS | NS | NS | NS |
| GS14 | NS | 66 | NS | NS | NS | NS |
| GS15 | NS | NS | NS | NS | NS | NS |
| GS16 | NS | NS | NS | NS | NS | NS |
| GS17 | 11.5 | 8 | NS | 21.7 | 4.48 | 9.5 |
| GS19 | NS | 38 | NS | 31.9 | 133 | NS |
| GS20 | NS | 50.2 | NS | 20 | NS | NS |
| GS21 | NS | NS | NS | 14.4 | NS | NS |
| GS22 | NS | NS | NS | 16.8 | NS | NS |
| GS23 | NS | NS | NS | 17.6 | NS | NS |
| GS24 | NS | NS | NS | 16.1 | NS | NS |
| GS25 | NS | NS | NS | 16.2 | NS | NS |
| GS26 | NS | NS | NS | 21.3 | NS | NS |
| GS27 | NS | NS | NS | 16.4 | NS | NS |
| GS28 | NS | NS | NS | 12.3 | NS | NS |

Example 29—Anti-Cancer Activity of GS Compounds

The following three assays were used to evaluate the anti-cancer activity and mechanism of action of the compounds of the present invention.

1. XTT Assay

The XTT assay is used to measure cellular metabolic activity as an indicator of cell viability, proliferation and cytotoxicity. This non-radioactive, colorimetric assay system was first described by Scudiero, et al. in 1988 (Paull, Kenneth D. et al., J Heterocycl Chem, 1988, 25: 911-914; Scudiero, Dominic A. et al., Cancer Res, 1988, 48: 4827-4833) and improved in subsequent years by several other investigators (Weislow, Owen S. et al., J Natl Cancer Inst, 1989, 81(8): 577-586; Roehm, N. W. et al., J Immunol Methods, 1991, 142: 257-265).

Figure 8:
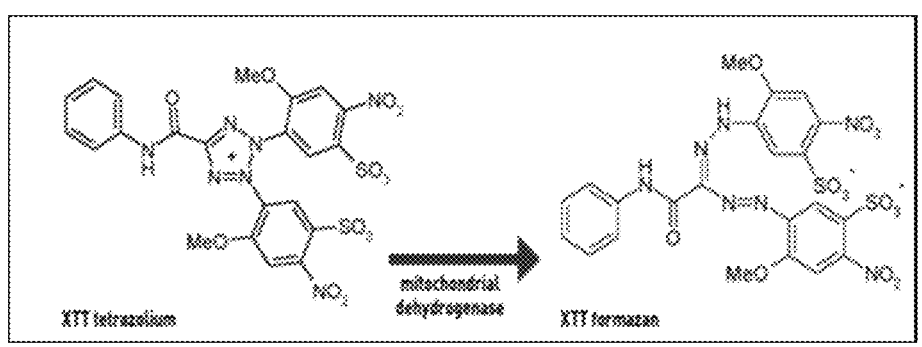
FIG. 8 shows the metabolism of XTT in the XTT assay.

The XTT assay is based on the reduction of a yellow tetrazolium salt (sodium 3'-[1-(phenylaminocarbonyl)-3,4-tetrazolium]-bis (4-methoxy6-nitro) benzene sulfonic acid hydrate or XTT) to an orange formazan dye by metabolically active cells (FIG. 8). The formazan dye formed is soluble in aqueous solutions and is directly quantified using a scanning multiwell spectrophotometer (ELISA reader). An increase in number of living cells results in an increase in the overall activity of mitochondrial dehydrogenases in the sample. This increase directly correlates to the amount of orange formazan formed, as monitored by the absorbance. Reduced number of living cells leads to reduced metabolism of quaternary salt and therefore reduced absorption.

Cell viability was assessed using the XTT assay kit (Roche, Mannheim, Germany) as described previously (Kouka, Paraskevi et al., Oxid Med Cell Longev. 2019, Article ID 1870965). Briefly, cancer cells per well were cultured in a 96-well plate in Dulbecco's modified Eagle's medium (DMEM). Following a 24 h incubation, 5, 10 and 50 µM of the tested GS compound was diluted in a serum-free DMEM and administered for 24 h. Subsequently, 50 µL of the XTT reagent (50:1) was added to each well. After 4 h of incubation, the absorbance was monitored at 450 nm and also at 630 nm as a reference wavelength in a BioTek ELx800 microplate reader (BioTek Instruments Inc., Winooski, VT, USA). As a negative control, samples containing serum-free DMEM only were used.

2. CellTiter Glo® Luminescent Cell Viability Assay

The CellTiter-Glo® Luminescent Cell Viability Assay (Promega Corporation; Madison, WI) is a homogeneous method of determining the number of viable cells in culture based on quantitation of the ATP present, an indicator of metabolically active cells. The homogeneous assay procedure involves adding the single reagent (CellTiter-Glo® Reagent) directly to cells cultured in serum-supplemented medium. The homogeneous "add-mix-measure" format results in cell lysis and generation of a luminescent signal proportional to the amount of ATP present. The amount of ATP is directly proportional to the number of cells present in culture.

Cancer cells (3,000 cells/well) were harvested in a 96-well plate. Then, the cancer cells were treated with GS compounds and incubated for 24 hours. The MT Cell Viability Substrate, NanoLuc® Enzyme and cell culture medium was equilibrated to 37° C. The 2× RealTime-Glo™ reagent was prepared by diluting the MT Cell Viability Substrate and NanoLuc® Enzyme in 37° C. cell culture medium to a 2× concentration for each reagent. For example, 1 mL of 2× RealTime-Glo™ reagent was prepared by adding 2 µL of MT Cell Viability Substrate, 1,000×, and 2 µL of NanoLuc® Enzyme, 1,000×, to 996 µL of cell culture medium to form the 2× RealTime-Glo™ reagent. Then, an equal volume of 2× RealTime-Glo™ reagent was added to the cancer cells. The cells were kept for ~20 minutes in the cell culture incubator and then luminescence was measured by using a plate-reading luminometer.

3. ELISA Assay

ELISA assay was used to evaluate the effect of GS compounds on protein activity levels in PANC-1 cancer cells. PANC-1 cells were serum-starved overnight and then treated with rIGF1 (100 ng/mL) for 24 hours, with or without GS27 (5 µM). The levels of the following proteins were evaluated by ELISA assay: a) p70 S6 (T389) (cat no. 54164C, Cell Signaling); b) pAKT (S473), (cat no. 80895, Cell Signaling); c) pACLY (S455), (cat no. okag1672, Avivasysbio); d) pAMPK (T172) (cat no. 7959C, Cell Signaling) and e) p65/NFKB (S536), (cat no. 7173, Cell Signaling).

Cell Lines

A total of eight cancer cell lines and 1 "normal" cell line were used in order to evaluate the effects of GS compounds on cancer and normal cell viability. The cell lines used include the following:

MIA PaCa-2 is a human pancreatic ductal adenocarcinoma cell line derived from the carcinoma of a 65-year-old male.

Hep G2 (or HepG2) is a human liver cancer cell line. Hep G2 is an immortal cell line which was derived from the liver tissue of a 15-year-old African American adolescent boy with a well-differentiated hepatocellular carcinoma. Hep G2 cells are a suitable in vitro model system for the study of polarized human hepatocytes.

HeLa is a human immortal cell line used in scientific research. It is the oldest and most commonly used human cell line. The line was derived from cervical cancer cells taken on Feb. 8, 1951 from Henrietta Lacks, a patient who died of cancer on Oct. 4, 1951.

MCF-7 ER+ is a human breast cancer cell line isolated in 1970 from a 69-year-old Caucasian woman. Prior to MCF-7, it was not possible for cancer researchers to obtain a mammary cell line that was capable of living longer than a few months.

MDA-MB-231 is a human epithelial breast cancer cell line that was established from a pleural effusion of a 51-year-old Caucasian female with a metastatic mammary adenocarcinomal and is one of the most commonly used breast cancer cell lines in medical research laboratories.

MKN-45 is a human gastric adenocarcinoma, established from the poorly differentiated adenocarcinoma of the stomach (medullary type) of a 62-year-old woman.

HCT-116 is a human colorectal cancer cell lines that has a mutation in RAS proto-oncogene.

MCF-10A is a human non-tumorigenic mammary epithelial cell line derived from a 36-year old female.

PANC-1 is a human pancreatic ductal adenocarcinoma cell line derived from the carcinoma of a 56-year-old male.

Statistical Analysis

The results were analyzed by one-way ANOVA followed by Tukey's test multiple comparisons test. The results are expressed as mean±SEM. The level of statistical significance was set at p<0.05. All statistical analyses were performed using the SPSS software (version 20.0; SPSS, Inc., Chicago, IL, USA).

The effects of exemplary compounds on cancer cell lines and one non-tumorigenic cell line (control) were investigated using a high throughput screening assay. More specifically, the effects of the GS compounds on cell growth was evaluated by the XTT assay for cell lines HepG2, HeLa, MCF7 ER+, MDA-MB-231, and MKN-45, and by the Cell Glo luminescence assay for cell lines MIA PaCa-2, HCT-116, MCF-10A, and PANC-1.

The results of these investigations is shown below. Data not statistically significant is notated in the Tables as NS.

Figure 9A:
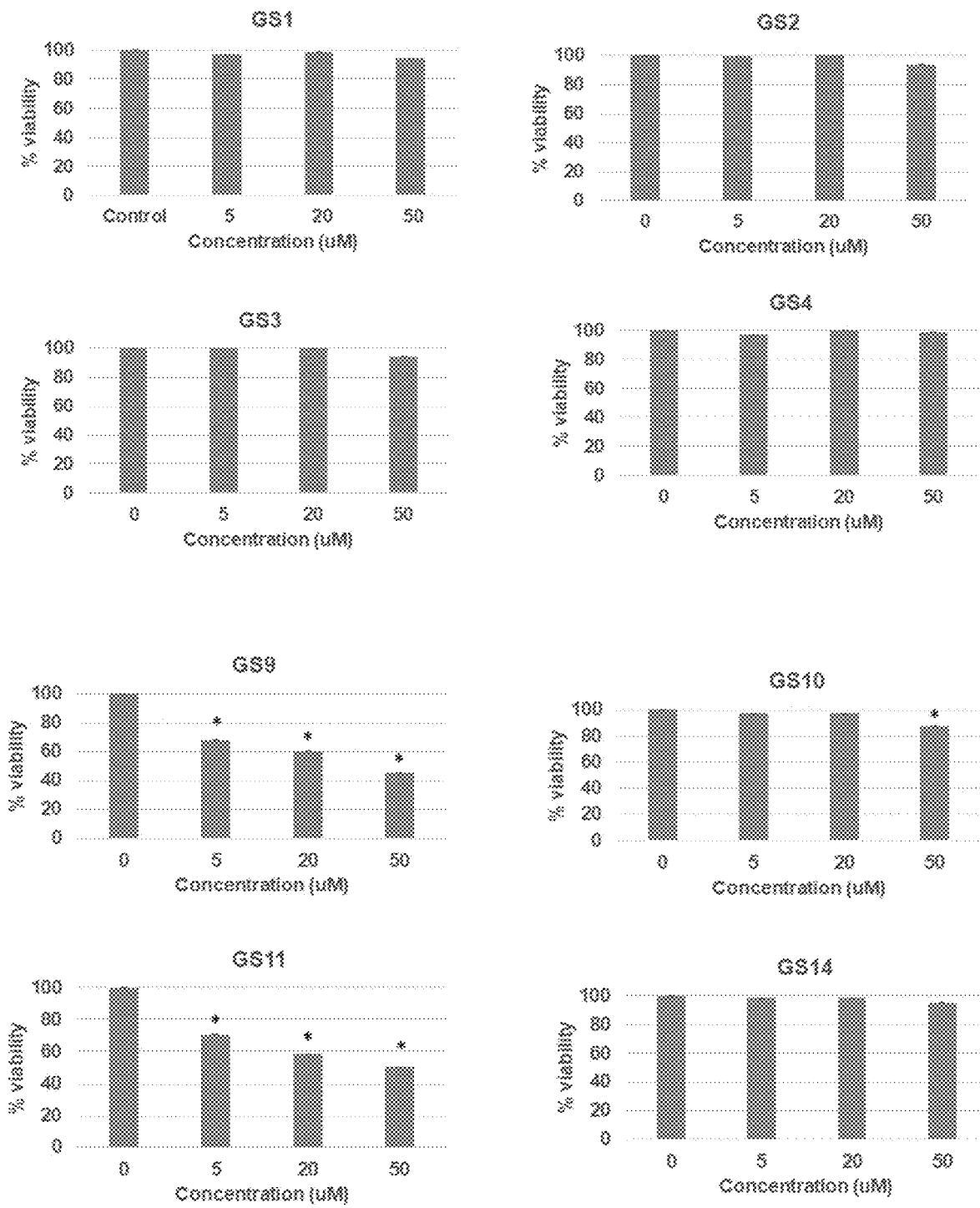
FIG. 9A to 9C show the effects of GS compounds (5, 20, 50 μM) in MiaPaCa-2 pancreatic cancer cell growth (24h) post treatment.
Figure 9B:
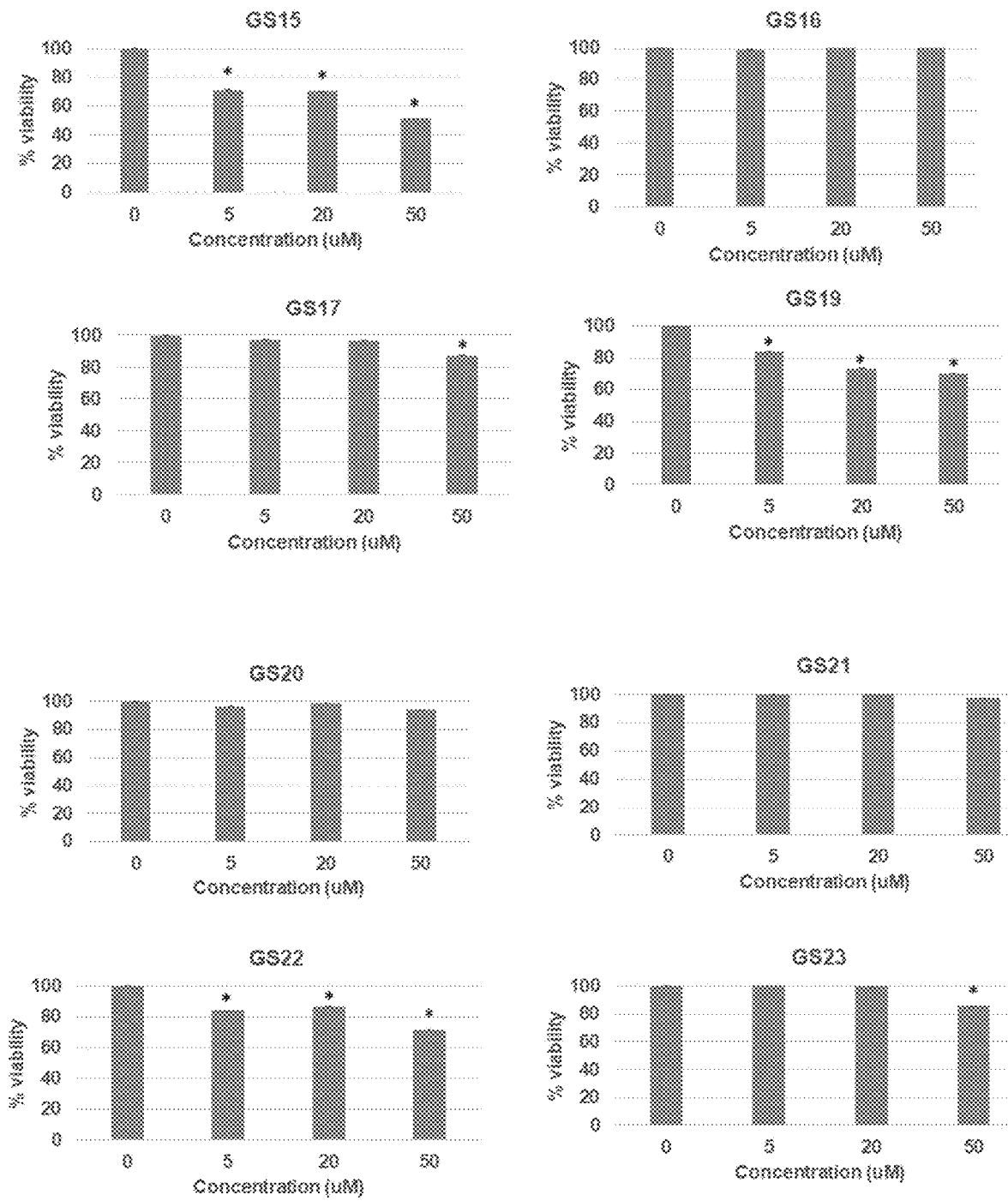
Figure 9C:
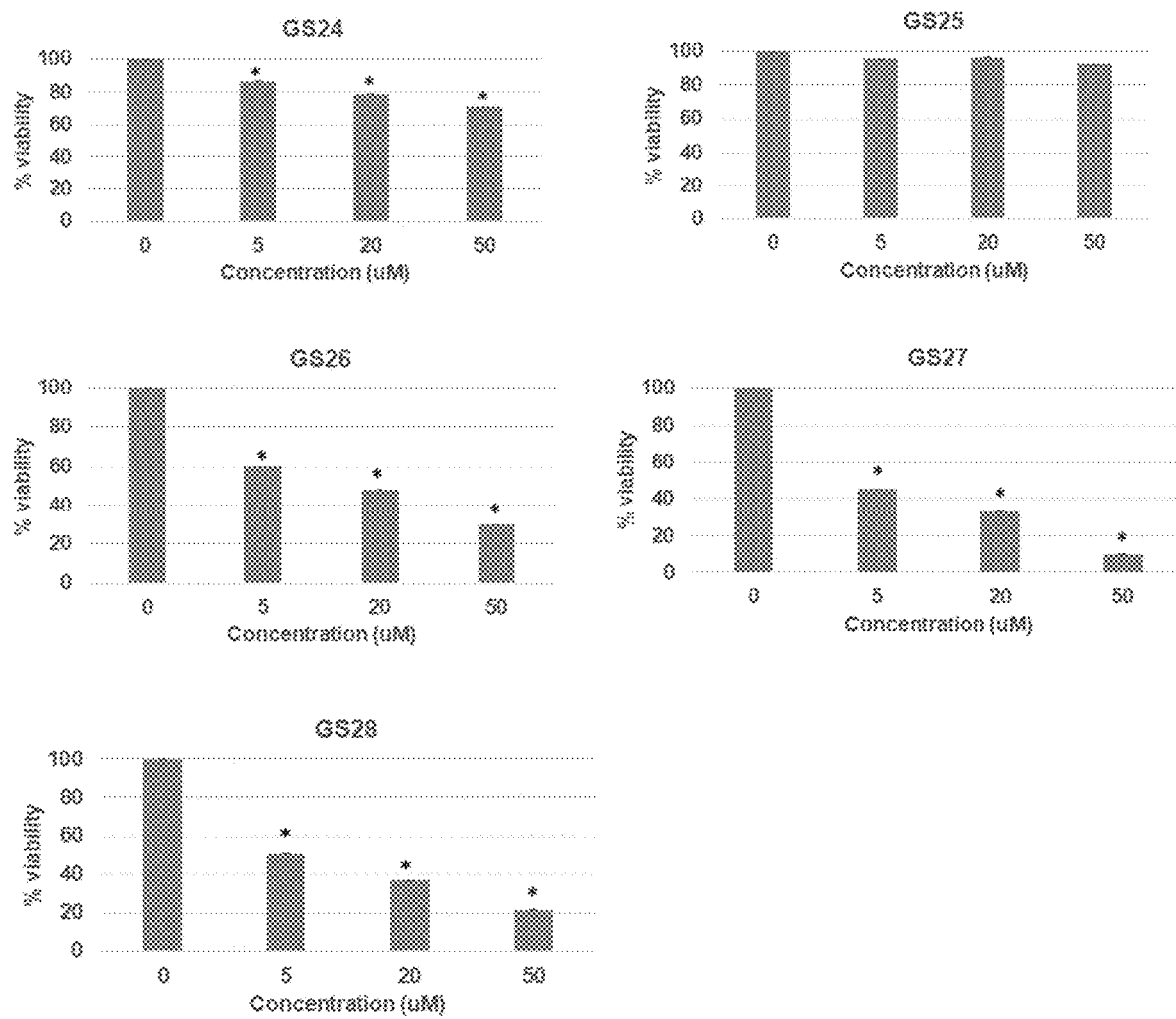
Figure 10A:
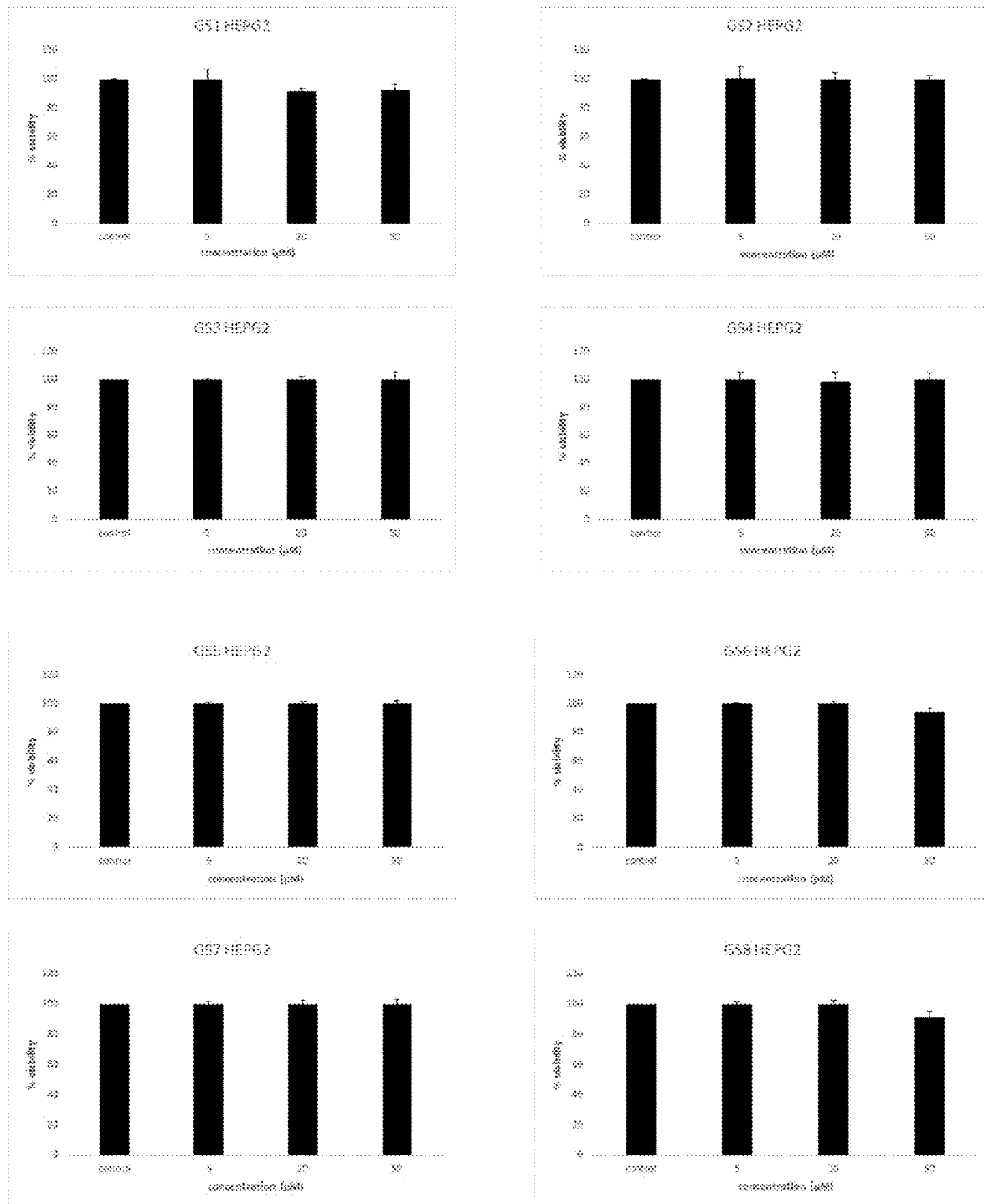
FIG. 10A to 10D show the effects of GS compounds (5, 20, 50 μM) in HepG2 liver cancer cell growth (24h) post treatment.
Figure 10B:
Figure 10C:
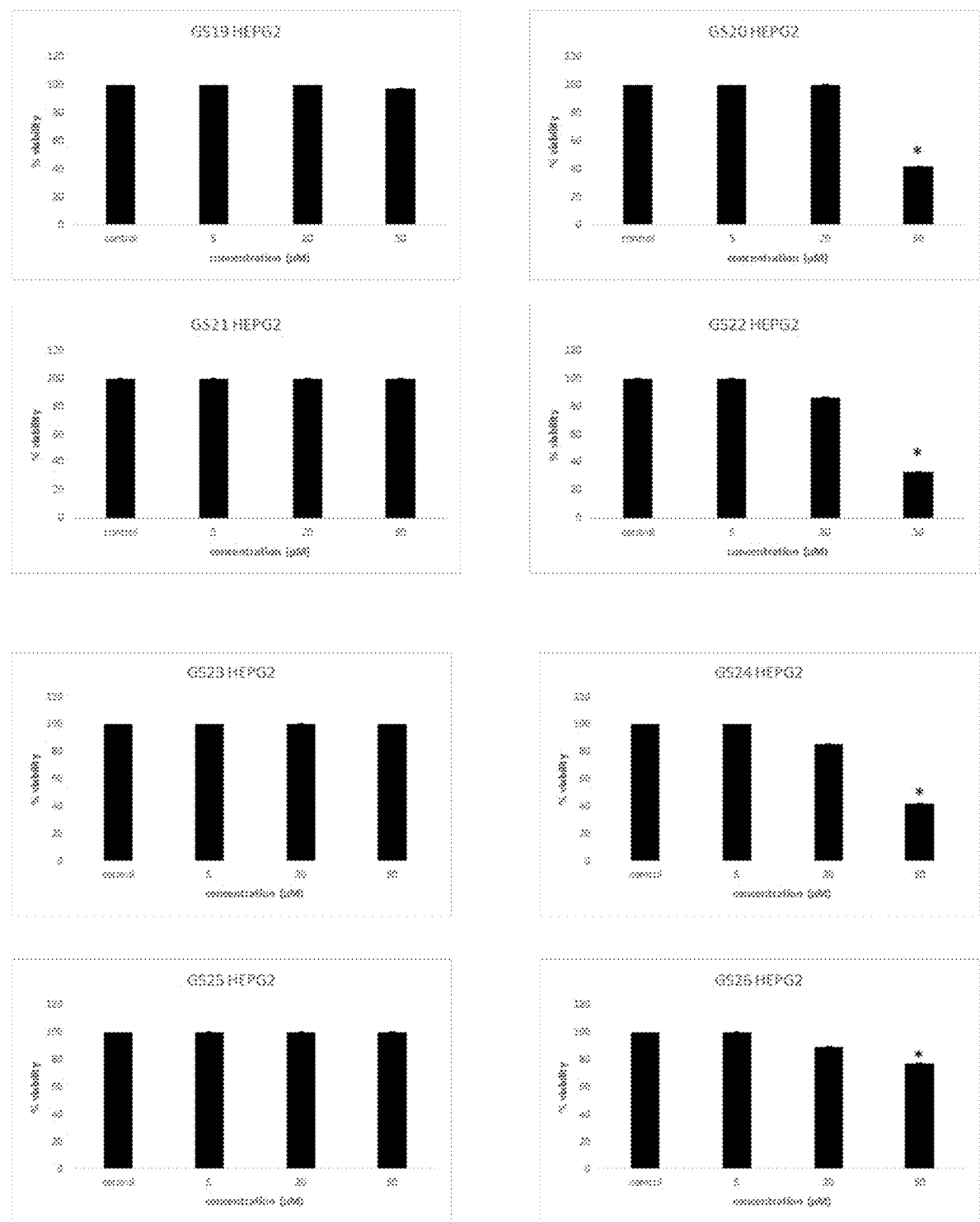
Figure 10D:
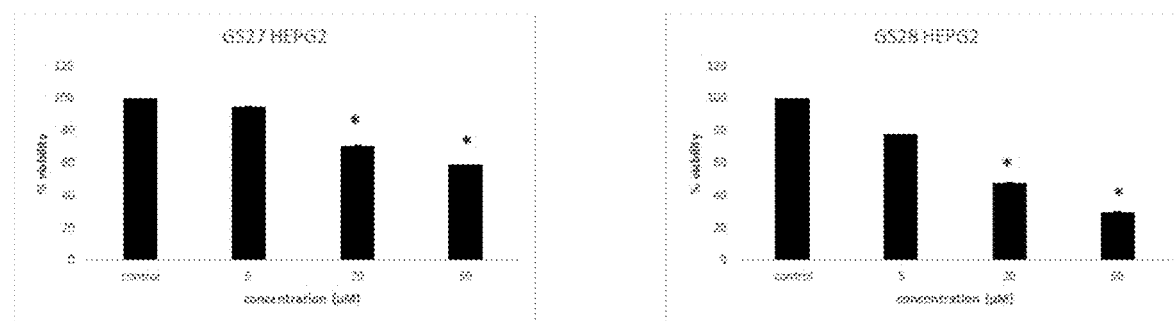
Figure 11A:
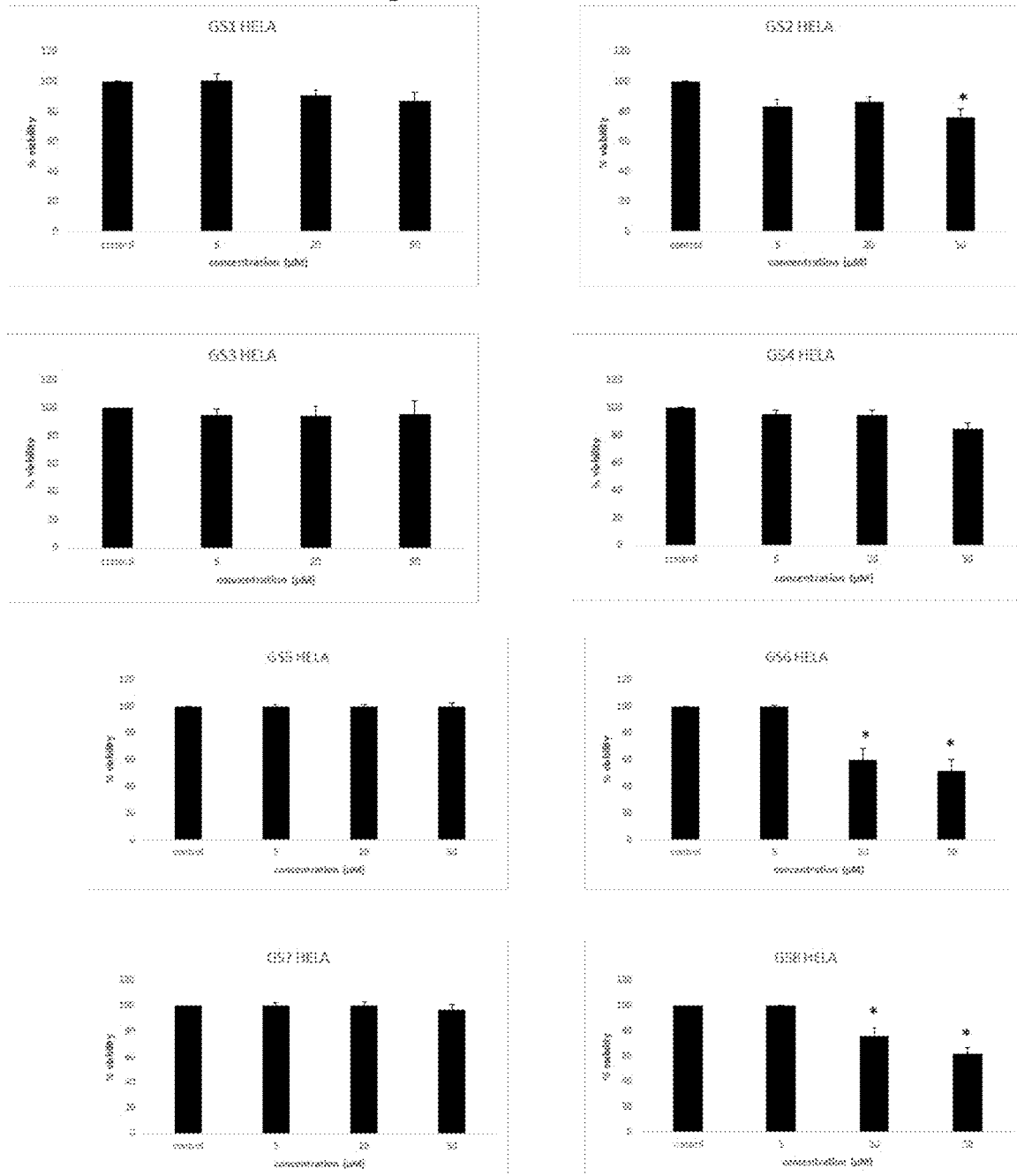
FIG. 11A to 11D show the effects of GS compounds (5, 20, 50 μM) in HeLa cervical cancer cell growth (24h) post treatment.
Figure 11B:
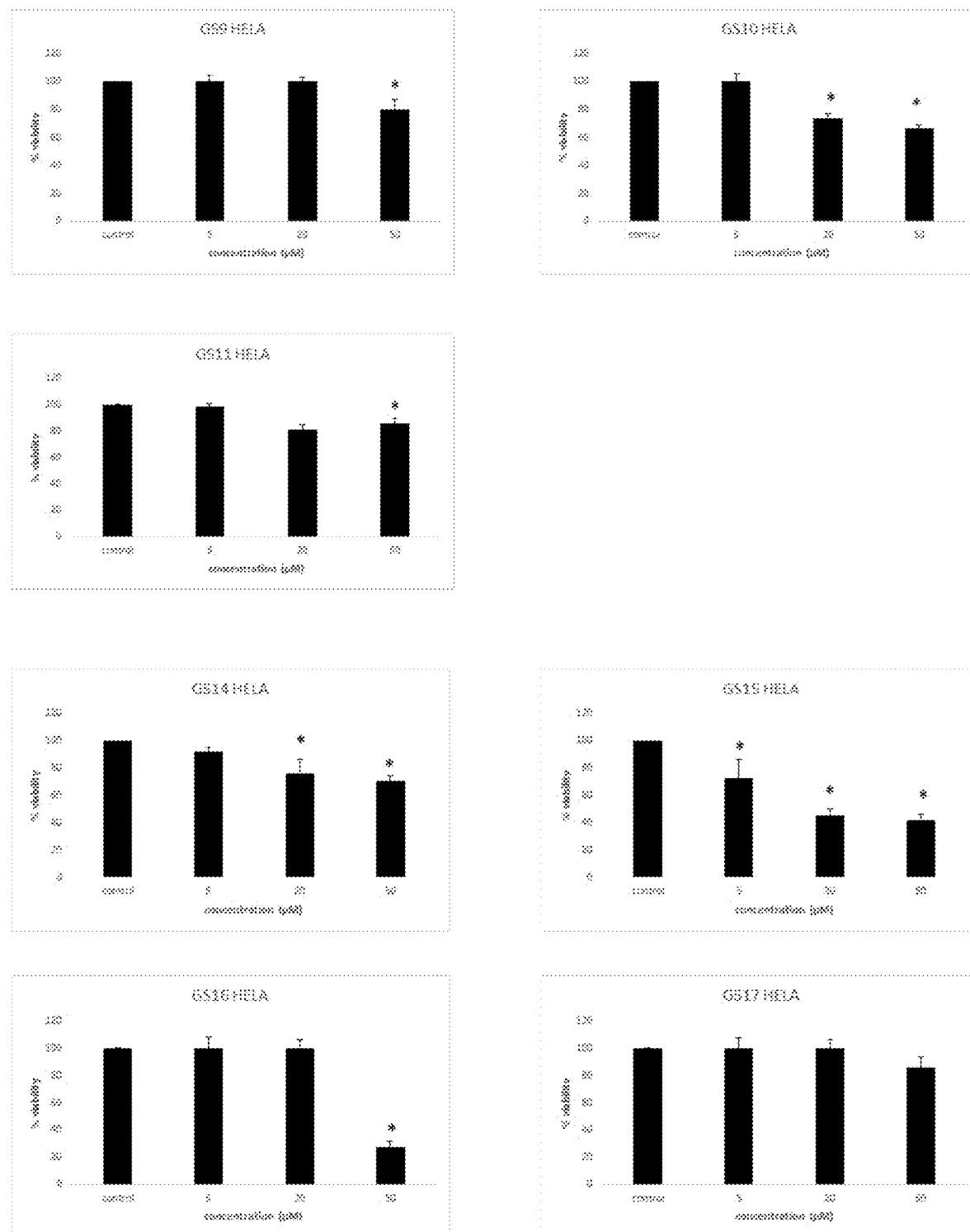
Figure 11C:
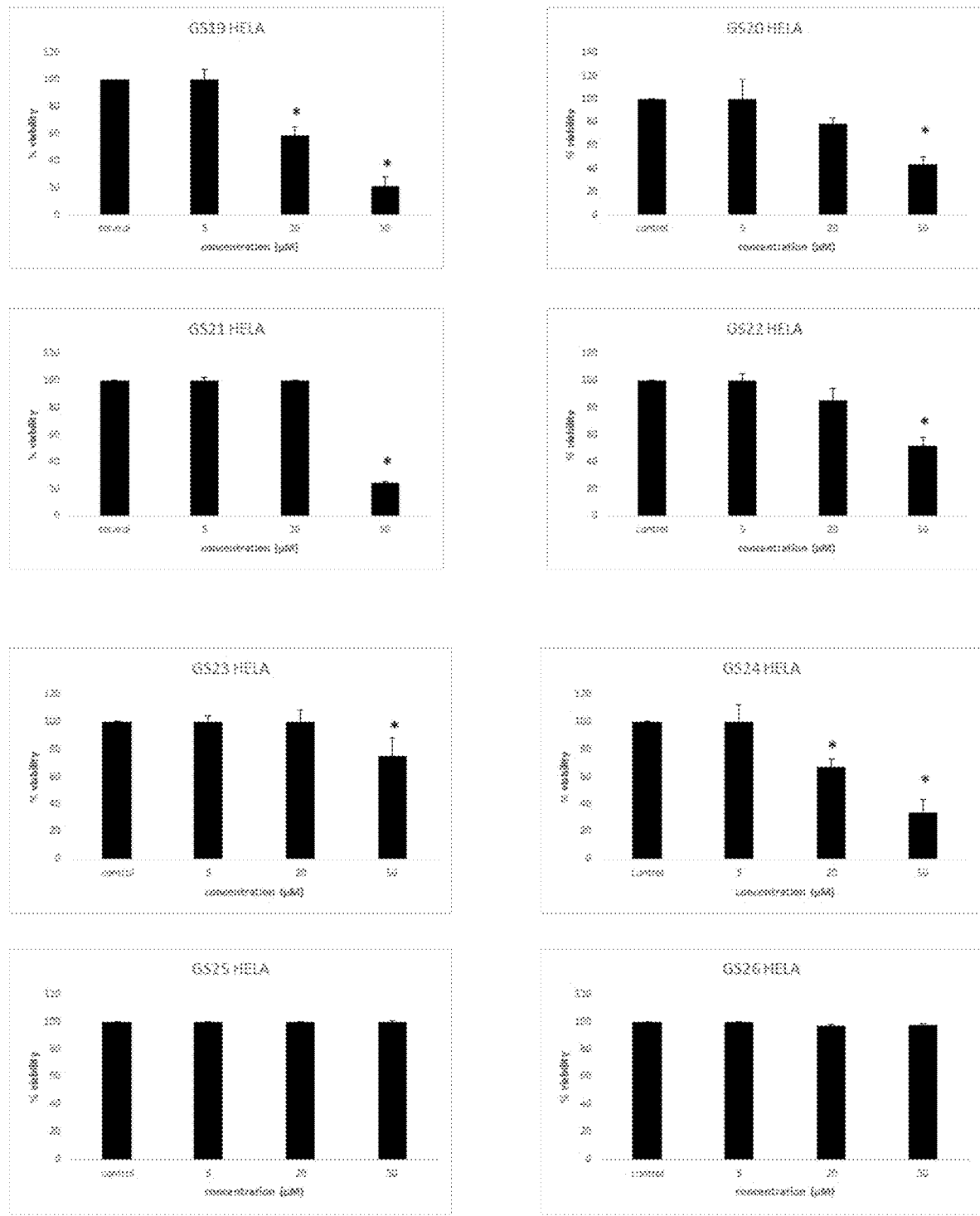
Figure 11D:
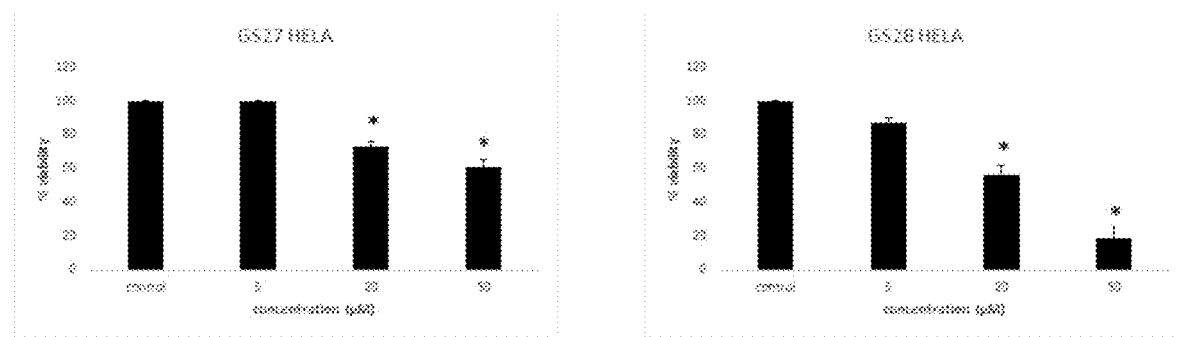
Figure 12A:
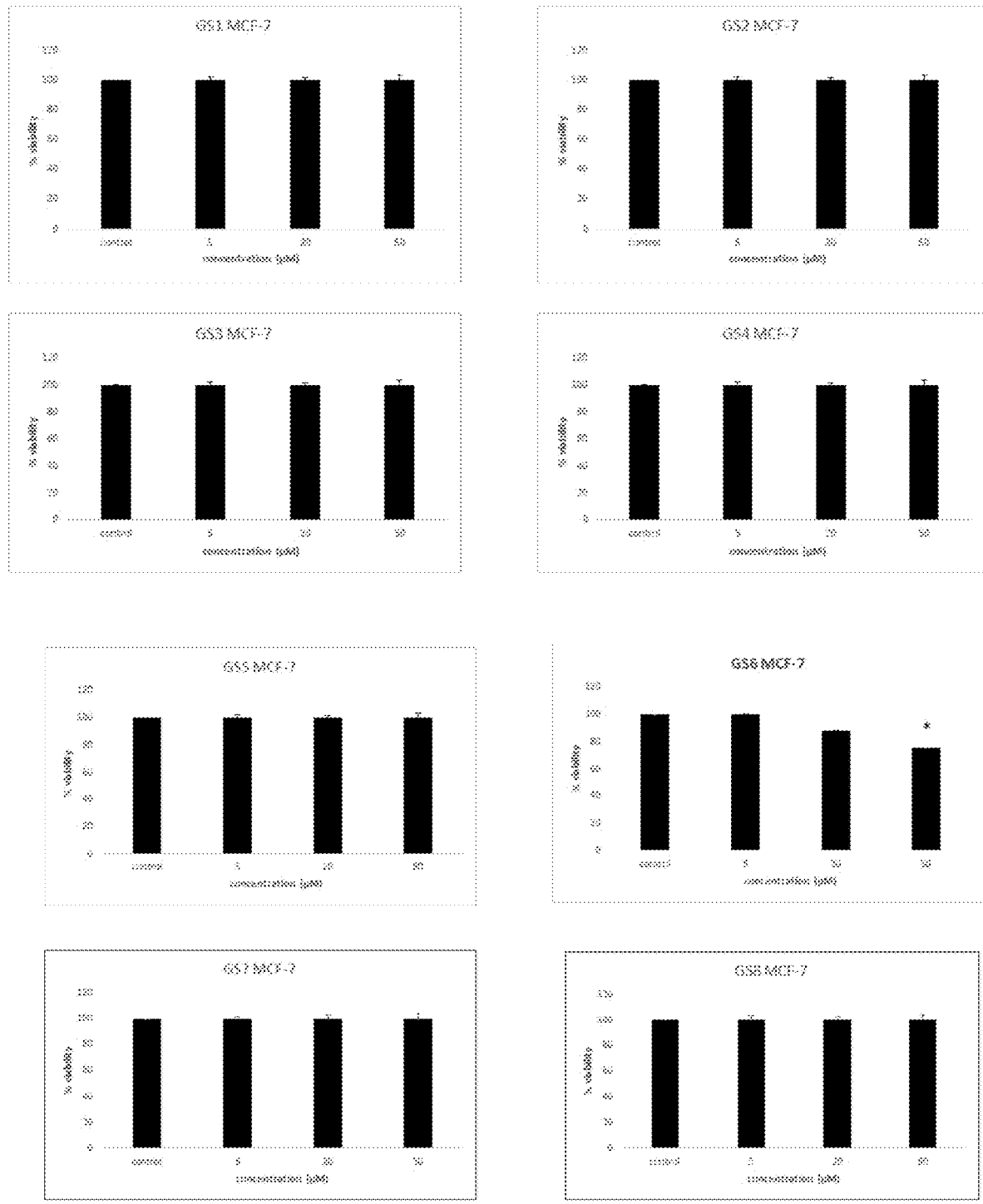
FIG. 12A to 12D show the effects of GS compounds (5, 20, 50 μM) in MCF7 breast cancer cell growth (24h) post treatment.
Figure 12B:
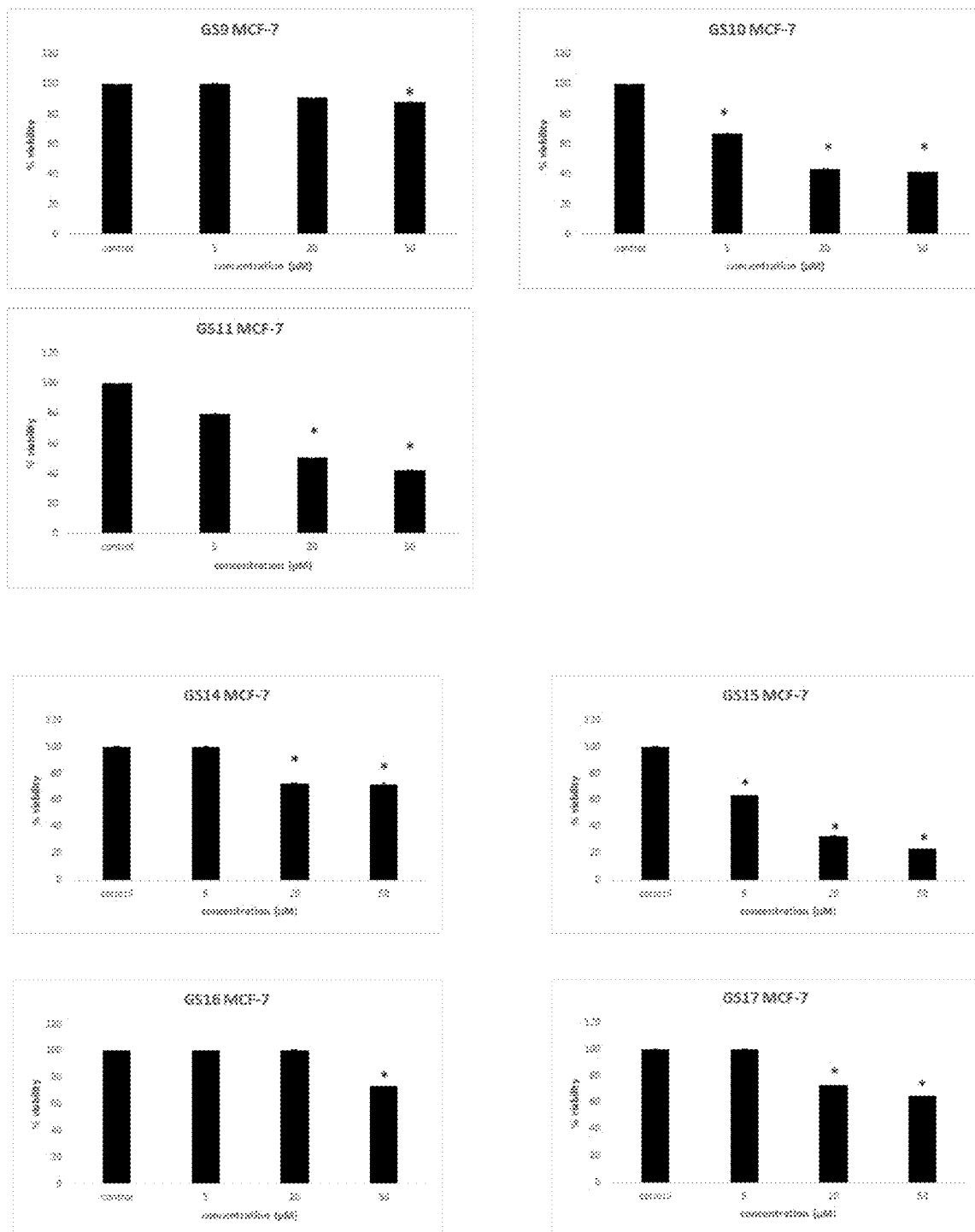
Figure 12C:
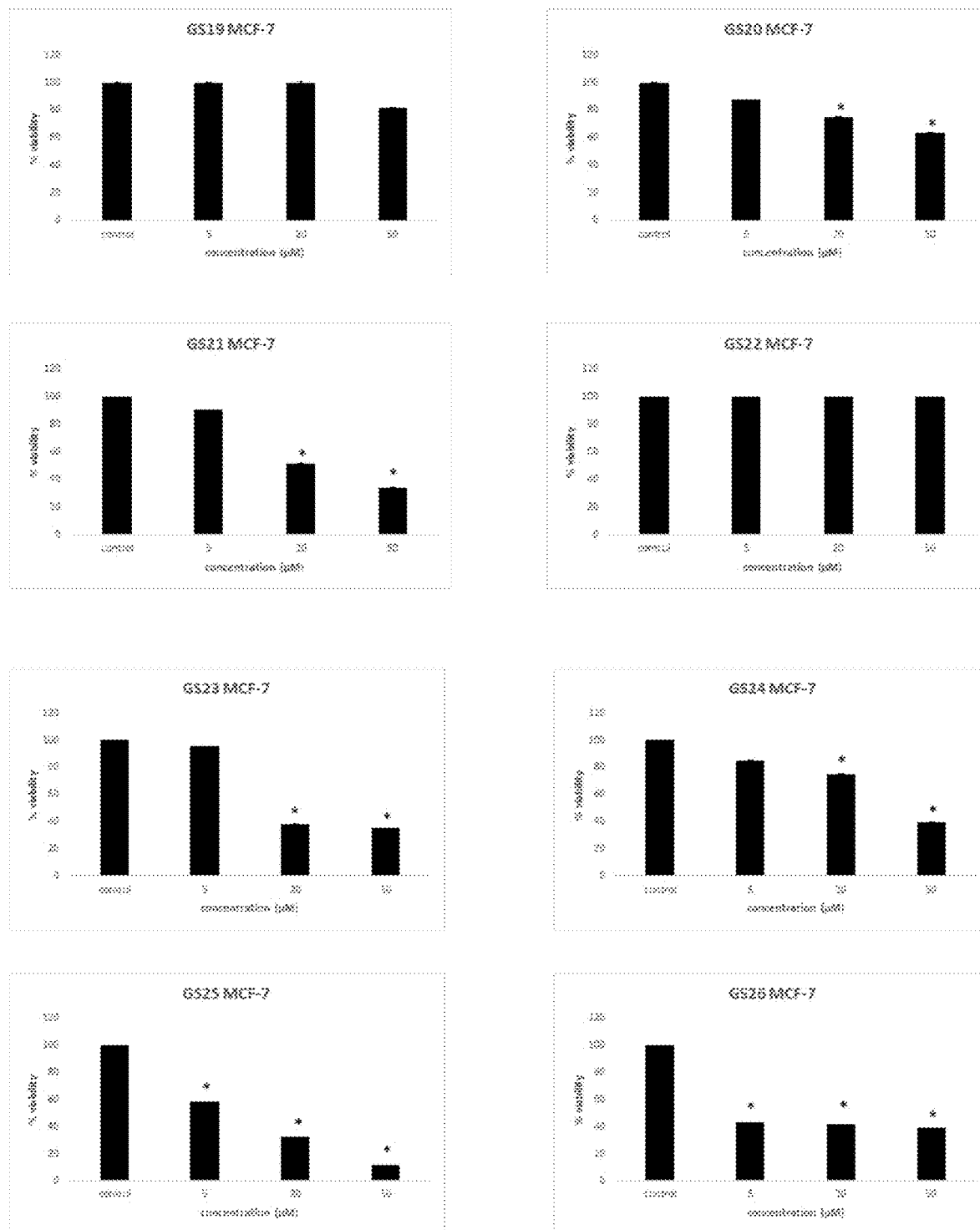
Figure 12D:
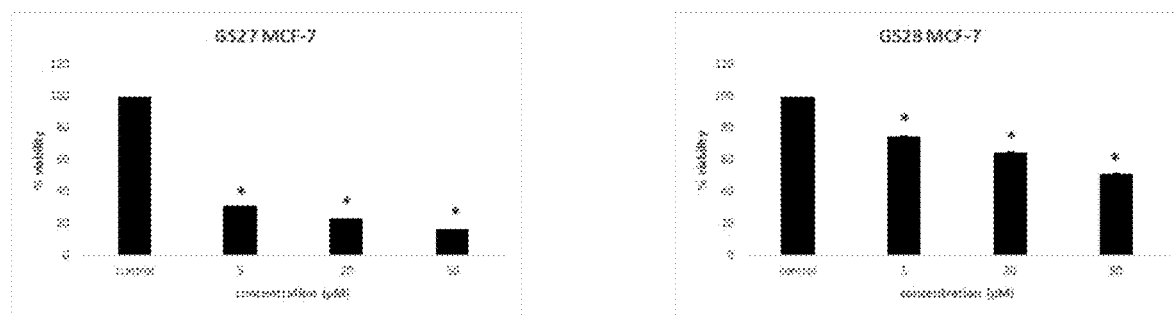
Figure 13A:
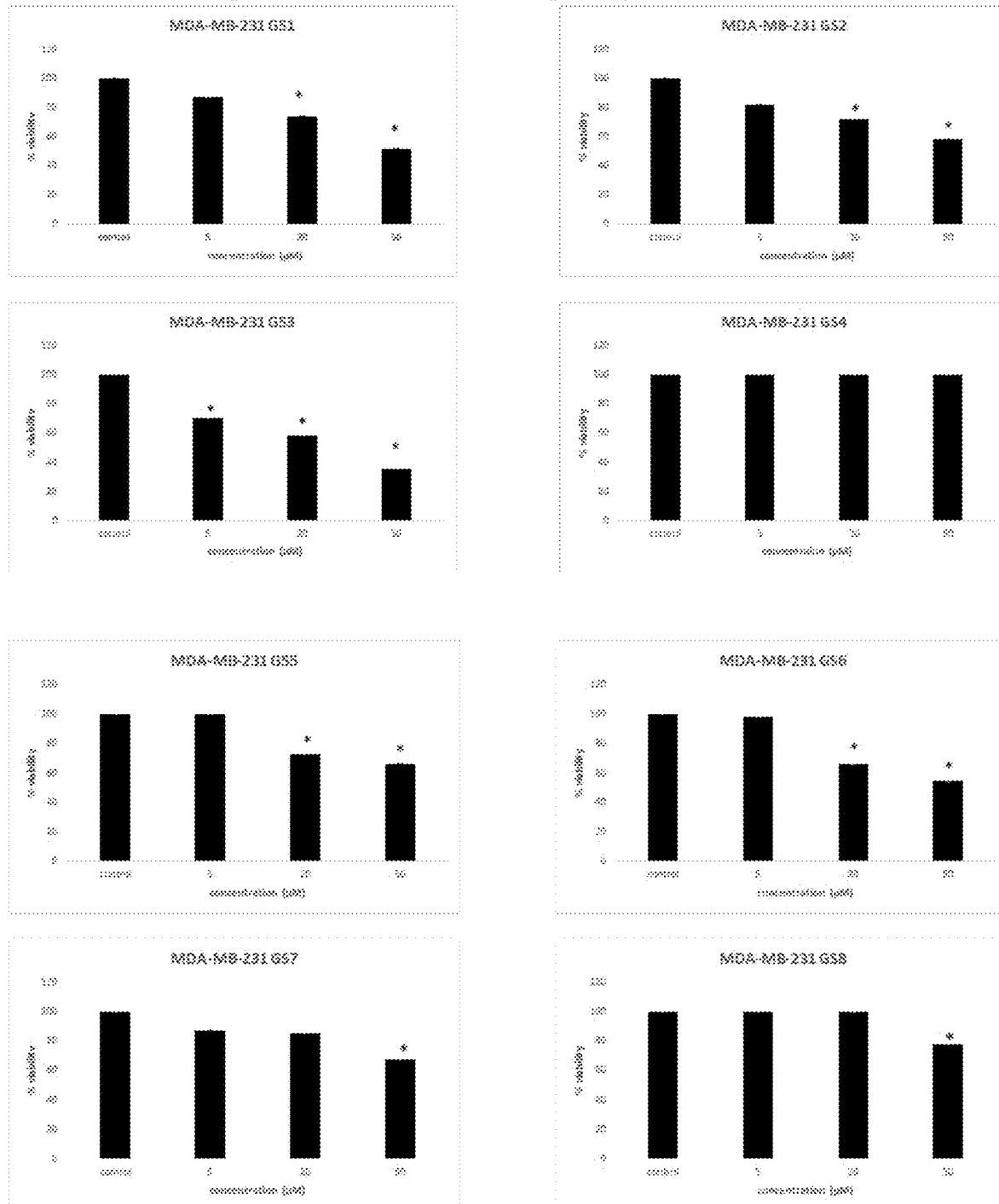
FIG. 13A to 13D show the effects of GS compounds (5, 20, 50 μM) in MDA-MB-231 breast cancer cell growth (24h) post treatment.
Figure 13B:
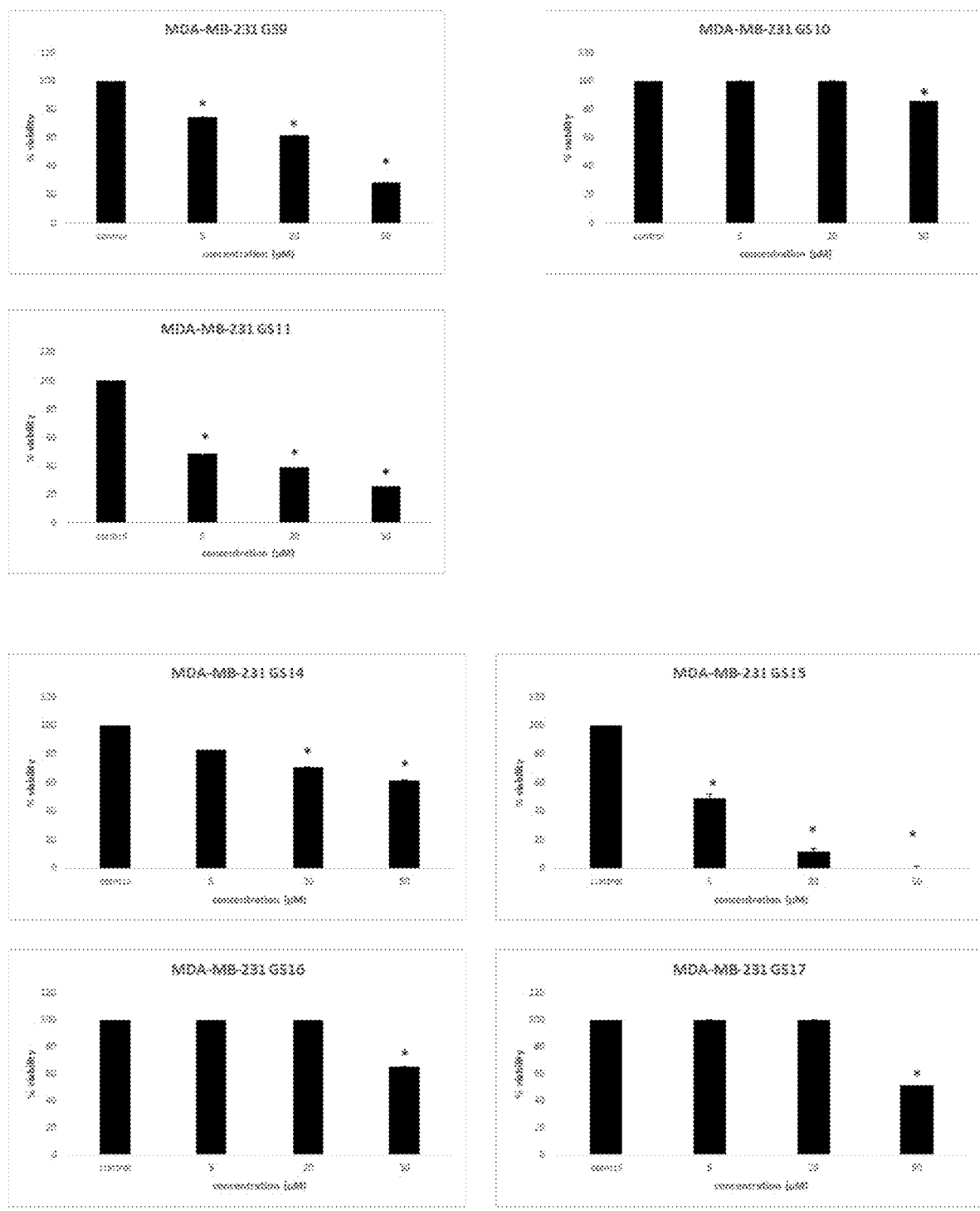
Figure 13C:
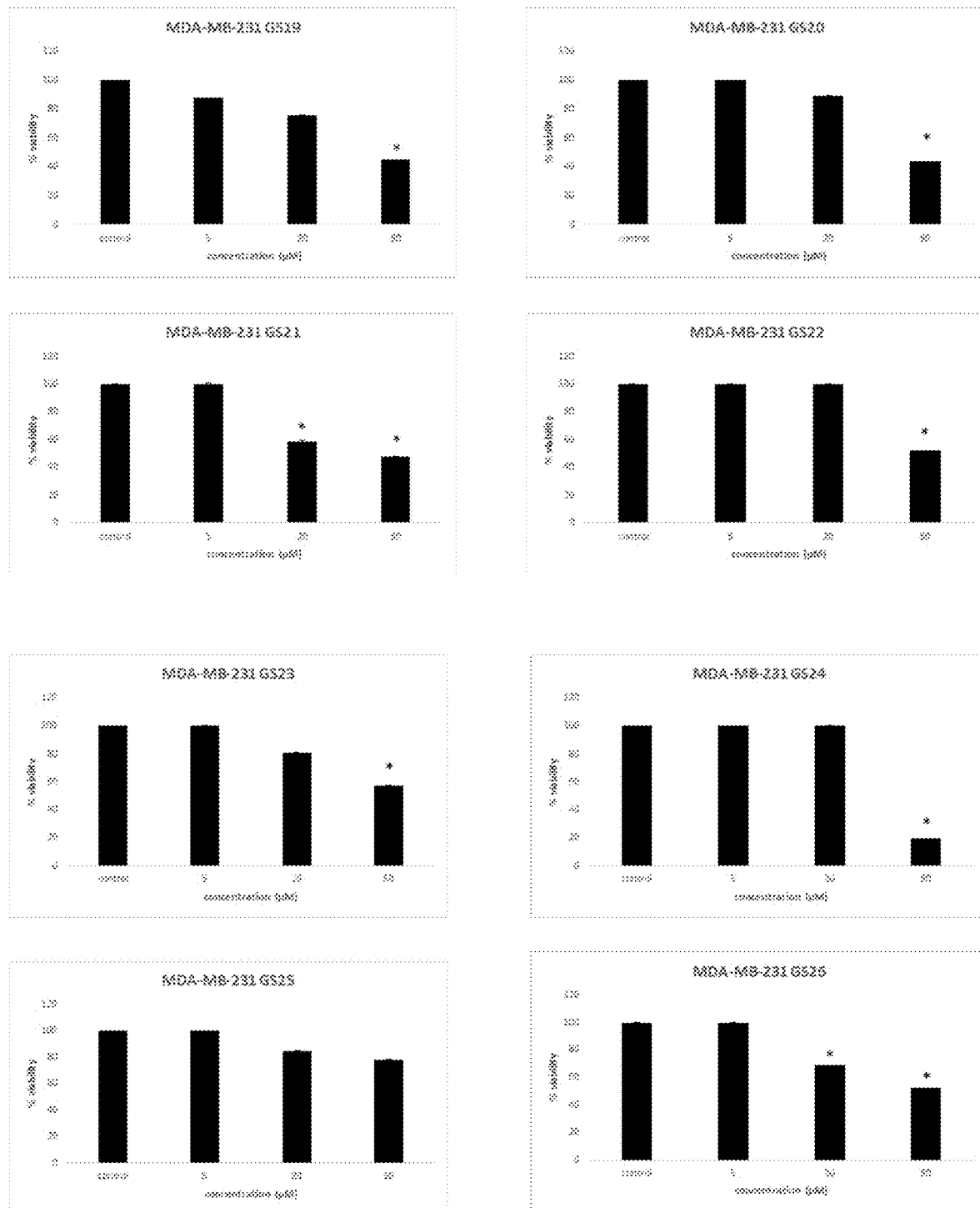
Figure 13D:
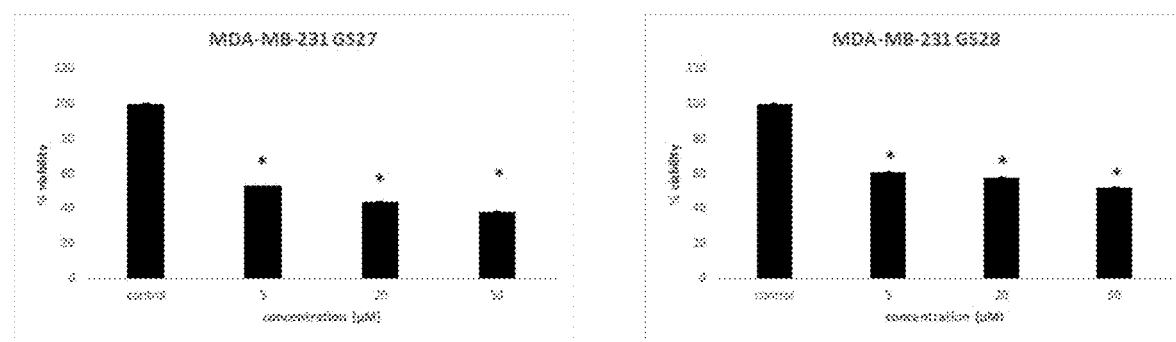
Figure 14A:
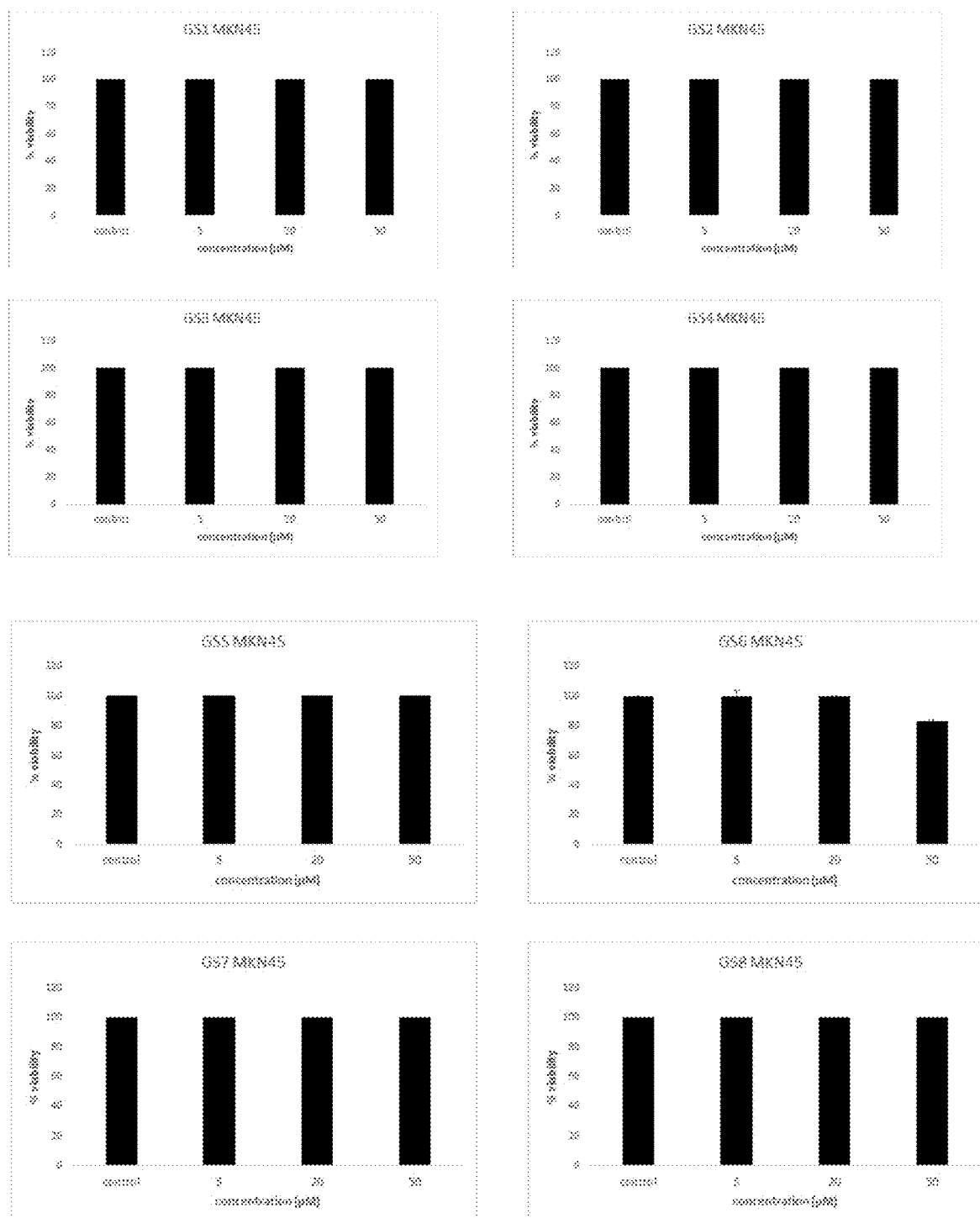
FIG. 14A to 14D show the effects of GS compounds (5, 20, 50 μM) in MKN-45 gastric cancer cell growth (24h) post treatment.
Figure 14B:
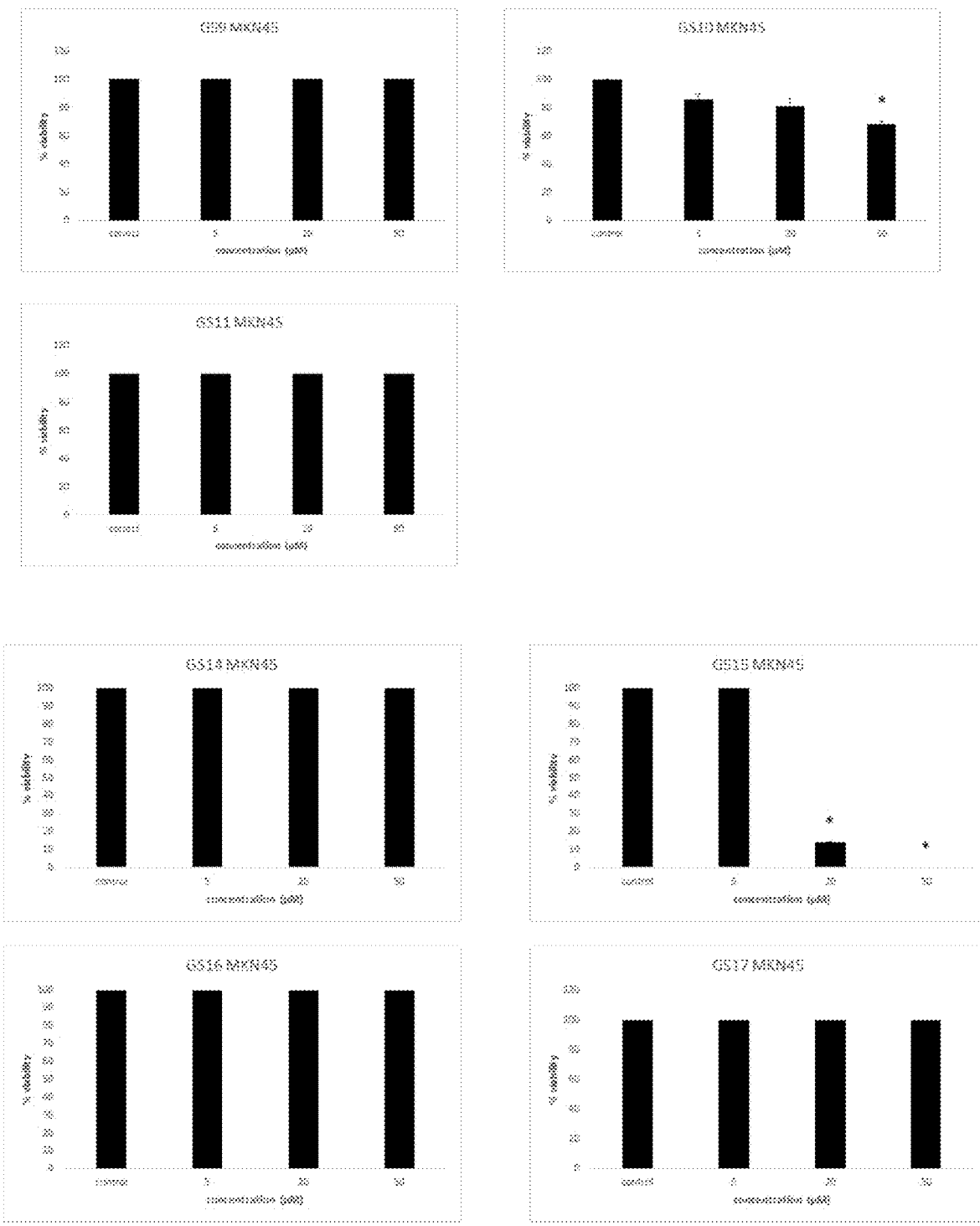
Figure 14C:
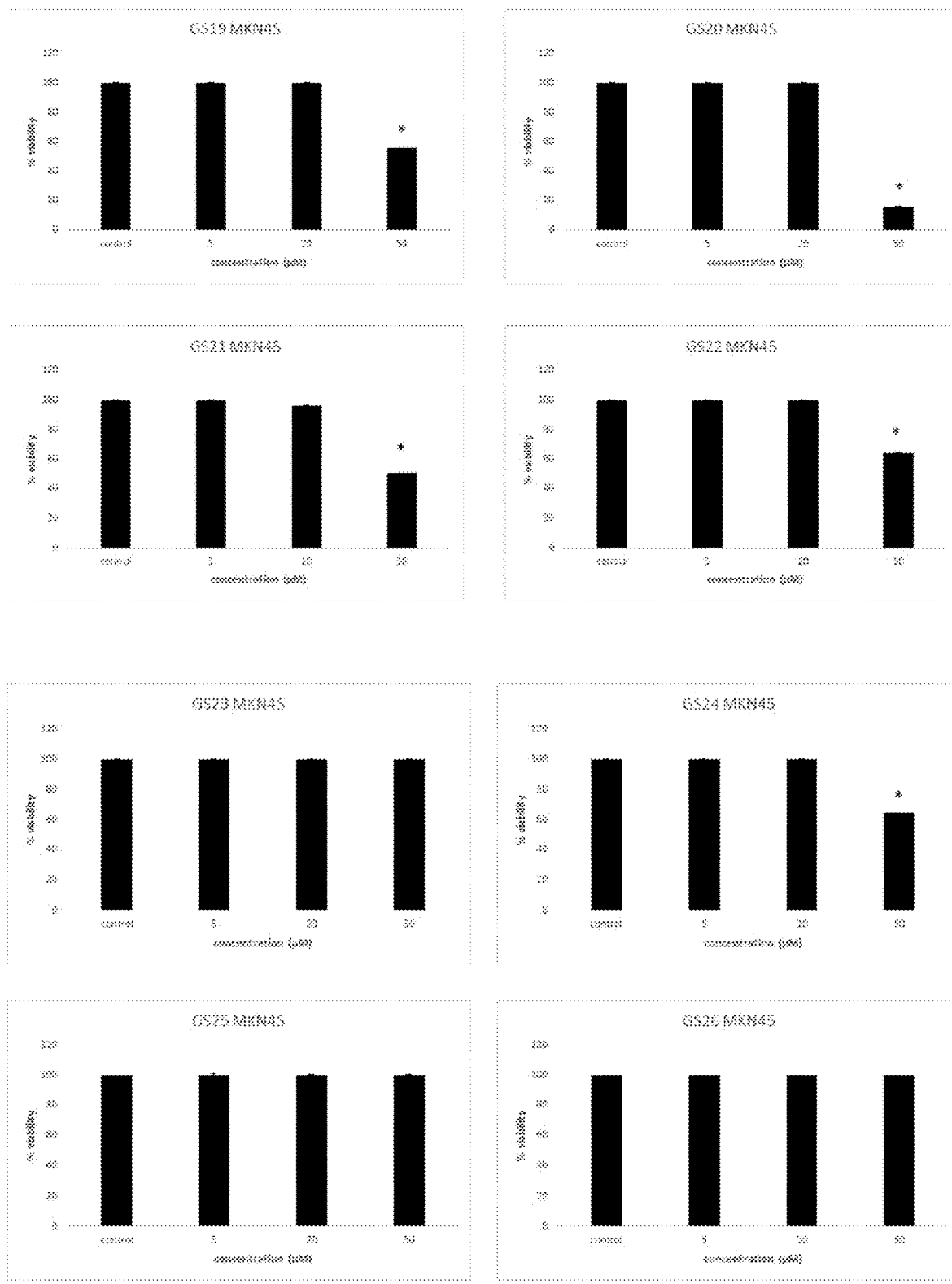
Figure 14D:
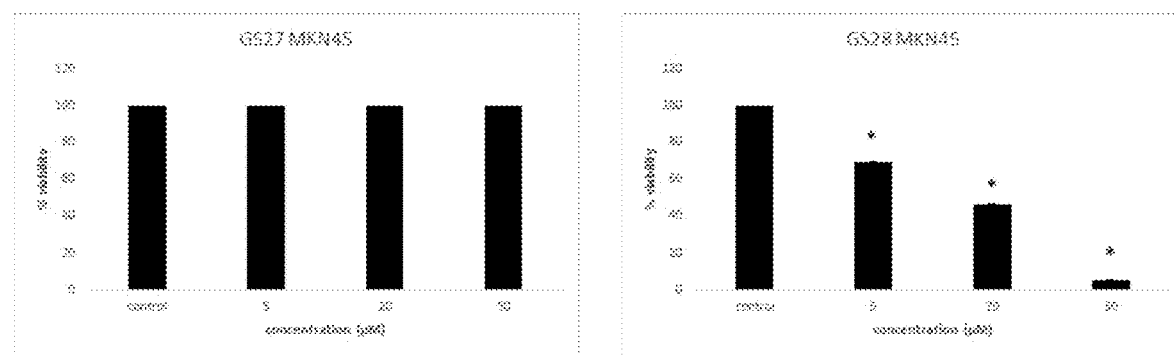

Data from the assay in MIA PaCa-2 human pancreatic cell line is shown in Table 3 and FIG. 9A to 9C.

TABLE 3

Compounds Cell Growth Inhibition (%) in MiaPaCa-2 pancreatic cancer cells

| Known Compounds (n = 16) | Effectiveness to suppress MIA PaCa-2 cell growth (50 uM) | Novel Compounds (n = 10) | Effectiveness to suppress MIA PaCa-2 cell growth (50 uM) |
|---|---|---|---|
| GS1 | NS | GS8 | NS |
| GS2 | NS | GS9 | 55% |
| GS3 | NS | GS10 | 22% |
| GS4 | NS | GS11 | 50% |
| GS5 | NS | GS14 | NS |
| GS6 | NS | GS24 | 28% |
| GS7 | NS | GS25 | NS |
| GS15 | 49% | GS26 | 70% |
| GS16 | NS | GS27 | 91% |
| GS17 | NS | GS28 | 79% |
| GS19 | 30% | | |
| GS20 | NS | | |
| GS21 | NS | | |
| GS22 | 28% | | |
| GS23 | 15% | | |

Data from the assay in HepG2 human liver cancer cell line is shown in Table 4 and FIG. 10A to 10D.

TABLE 4

Compounds Cell Growth Inhibition (%) in HepG2 liver cancer cells

| Known Compounds (n = 16) | Effectiveness to suppress HepG2 cell growth (50 uM) | Novel Compounds (n = 10) | Effectiveness to suppress HepG2 cell growth (50 uM) |
|---|---|---|---|
| GS1 | NS | GS8 | NS |
| GS2 | NS | GS9 | NS |
| GS3 | NS | GS10 | NS |
| GS4 | NS | GS11 | NS |
| GS5 | NS | GS14 | 10% |
| GS6 | NS | GS24 | 57.9% |
| GS7 | NS | GS25 | NS |
| GS15 | 55% | GS26 | 50% |
| GS16 | NS | GS27 | 40.9% |
| GS17 | NS | GS28 | 69.7% |
| GS19 | NS | | |
| GS20 | 50% | | |
| GS21 | NS | | |
| GS22 | 66.8% | | |
| GS23 | NS | | |

Data from the assay in HeLa cervical cancer cell line is shown in Table 5 and FIG. 11A to 11D.

TABLE 5

Compounds Cell Growth Inhibition (%) in HeLa cervical cancer cells

| Known Compounds (n = 16) | Effectiveness to suppress HeLa cell growth (50 uM) | Novel Compounds (n = 10) | Effectiveness to suppress HeLa cell growth (50 uM) |
|---|---|---|---|
| GS1 | NS | GS8 | 38.2% |
| GS2 | 24.4% | GS9 | 20% |
| GS3 | NS | GS10 | 33.5% |
| GS4 | NS | GS11 | 14.4% |
| GS5 | NS | GS14 | 29.5% |
| GS6 | 48% | GS24 | 66.6% |
| GS7 | NS | GS25 | NS |
| GS15 | 57.9% | GS26 | NS |
| GS16 | 72.6% | GS27 | 39% |
| GS17 | NS | GS28 | 81% |
| GS19 | 79.1% | | |
| GS20 | 56.4% | | |
| GS21 | 75.8% | | |
| GS22 | 48.6% | | |
| GS23 | 25.2% | | |

Data from the assay in MCF-7 human breast cancer cell line is shown in Table 6 and FIG. 12A to 12D.

TABLE 6

Compounds Cell Growth Inhibition (%) in MCF-7 ER+ breast cancer cells

| Known Compounds (n = 16) | Effectiveness to suppress MCF7 cell growth (50 uM) | Novel Compounds (n = 10) | Effectiveness to suppress MCF7 cell growth (50 uM) |
|---|---|---|---|
| GS1 | NS | GS8 | NS |
| GS2 | NS | GS9 | 11.6% |
| GS3 | NS | GS10 | 58.7% |
| GS4 | NS | GS11 | 57.8% |
| GS5 | NS | GS14 | 28.4% |
| GS6 | 24.8% | GS24 | 60.5% |
| GS7 | NS | GS25 | 88.4% |
| GS15 | 76.8% | GS26 | 61% |
| GS16 | 26.6% | GS27 | 83.2% |
| GS17 | 35.2% | GS28 | 48.7% |
| GS19 | NS | | |
| GS20 | 36.1% | | |
| GS21 | 66% | | |
| GS22 | NS | | |
| GS23 | 64.7% | | |

Data from the assay in MDA-MB-231 human triple negative breast cancer cell line is shown in Table 7 and FIG. 13A to 13D.

TABLE 7

Compounds Cell Growth Inhibition (%) in MDA-MB-231 triple negative breast cancer cells

| Known Compounds (n = 16) | Effectiveness to suppress MDA-MB-231 cell growth (50 uM) | Novel Compounds (n = 10) | Effectiveness to suppress MDA-MB-231 cell growth (50 uM) |
|---|---|---|---|
| GS1 | 48.3% | GS8 | 22.5% |
| GS2 | 41.8% | GS9 | 71.2% |
| GS3 | 64.7% | GS10 | 14% |
| GS4 | NS | GS11 | 74.3% |
| GS5 | 33.6% | GS14 | 38.2% |
| GS6 | 45.3% | GS24 | 80.5% |
| GS7 | 32.7% | GS25 | NS |
| GS15 | 98% | GS26 | 47.6% |
| GS16 | 35% | GS27 | 61.4% |
| GS17 | 47.6% | GS28 | 47.8% |
| GS19 | 55% | | |

TABLE 7-continued

Compounds Cell Growth Inhibition (%) in MDA-MB-231 triple negative breast cancer cells

| Known Compounds (n = 16) | Effectiveness to suppress MDA-MB-231 cell growth (50 uM) | Novel Compounds (n = 10) | Effectiveness to suppress MDA-MB-231 cell growth (50 uM) |
| --- | --- | --- | --- |
| GS20 | 56.4% | | |
| GS21 | 52.5% | | |
| GS22 | 48% | | |
| GS23 | 42.7% | | |

Data from the assay in MKN-45 human gastric cell line is shown in Table 8 and FIG. 14A to 14D.

TABLE 8

Compounds Cell Growth Inhibition (%) in MKN-45 gastric cancer cells

| Known Compounds (n = 16) | Effectiveness to suppress MKN-45 cell growth (50 uM) | Novel Compounds (n = 10) | Effectiveness to suppress MKN-45 cell growth (50 uM) |
| --- | --- | --- | --- |
| GS1 | NS | GS8 | NS |
| GS2 | NS | GS9 | NS |
| GS3 | NS | GS10 | 31.9% |
| GS4 | NS | GS11 | NS |
| GS5 | NS | GS14 | NS |
| GS6 | NS | GS24 | 35.4% |
| GS7 | NS | GS25 | NS |
| GS15 | 99.9% | GS26 | NS |
| GS16 | NS | GS27 | NS |
| GS17 | NS | GS28 | 95% |
| GS19 | 44.4% | | |
| GS20 | 84.1% | | |
| GS21 | 49.4% | | |
| GS22 | 35.8% | | |
| GS23 | NS | | |

Figure 15:
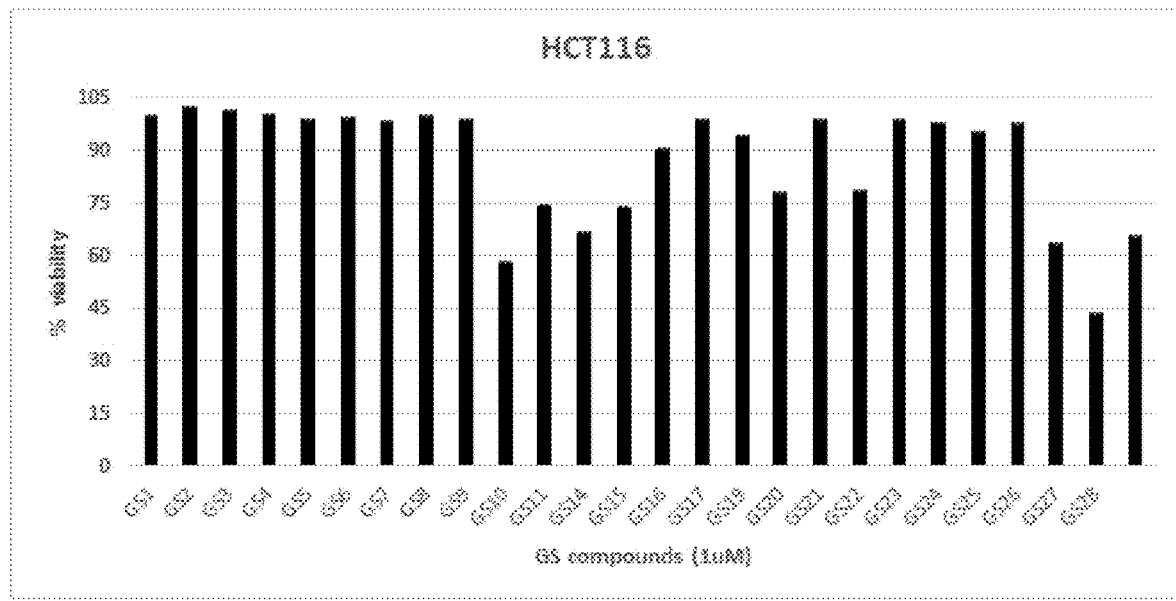
FIG. 15 shows the effects of GS compounds (1 μM) in HCT-116 colon cancer cell growth (24h) post treatment.

Data from the assay in HCT-116 human colorectal cancer cell line is shown in Table 9 and FIG. 15.

TABLE 9

Compounds Cell Growth Inhibition (%) in HCT-116 colon cancer cells

| Known Compounds (n = 16) | Effectiveness to suppress HCT-116 cell growth (1 uM) | Novel Compounds (n = 10) | Effectiveness to suppress HCT-116 cell growth (1 uM) |
| --- | --- | --- | --- |
| GS1 | NS | GS8 | NS |
| GS2 | NS | GS9 | 41.7% |
| GS3 | NS | GS10 | 25.7% |
| GS4 | NS | GS11 | 32.9% |
| GS5 | NS | GS14 | 26.4% |
| GS6 | NS | GS24 | NS |
| GS7 | NS | GS25 | NS |
| GS15 | NS | GS26 | 36.3% |
| GS16 | NS | GS27 | 56.5% |
| GS17 | NS | GS28 | 34.4% |
| GS19 | 21.6% | | |
| GS20 | NS | | |
| GS21 | 21.5% | | |
| GS22 | NS | | |
| GS23 | NS | | |

Several GS compounds showed anti-cancer properties by reducing the growth of cancer cells. To further evaluate the safety profile of the GS compounds and their specificity to suppress only cancer cell growth, without affecting normal cell growth, we used MCF-10A cells which are normal cells as a control. Safe GS compounds were identified as compounds that had no statistically significant (NS) effect on MCF-10A cell growth.

Figure 16:
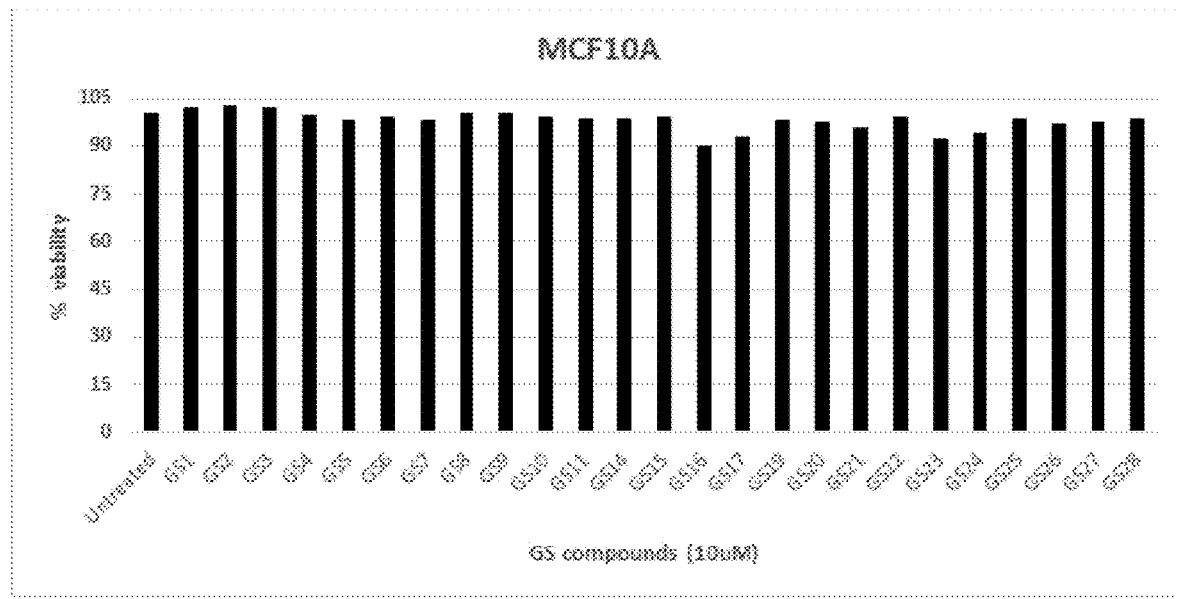
FIG. 16 shows the effects of GS compounds (10 μM) in MCF10A non-cancer mammary epithelial cell growth (24h) post treatment.

Data from the assay in MCF-10A non-tumorigenic human breast epithelial cell line is shown in Table 10 and FIG. 16.

TABLE 10

Compounds Cell Growth Inhibition (%) in MCF-10A non-tumorigenic mammary epithelial cells

| Known Compounds (n = 16) | Effectiveness to suppress MCF10A cell growth (10 uM) | Novel Compounds (n = 10) | Effectiveness to suppress MCF10 cell growth (10 uM) |
| --- | --- | --- | --- |
| GS1 | NS | GS8 | NS |
| GS2 | NS | GS9 | NS |
| GS3 | NS | GS10 | NS |
| GS4 | NS | GS11 | NS |
| GS5 | NS | GS14 | NS |
| GS6 | NS | GS24 | NS |
| GS7 | NS | GS25 | NS |
| GS15 | NS | GS26 | NS |
| GS16 | 10.1% | GS27 | NS |
| GS17 | NS | GS28 | NS |
| GS19 | NS | | |
| GS20 | NS | | |
| GS21 | NS | | |
| GS22 | NS | | |
| GS23 | NS | | |

Discussion

Novel GS Compounds have Unexpectedly Better Efficacy to Suppress Cancer Cell Growth in Different Cancer Types.

A high throughput screen in seven cancer cell lines and a non-tumorigenic epithelial cell line (control) was performed using the GS compounds. It was found that GS26, GS27 and GS28 compounds had the best efficacy to suppress MIA PaCa-2 pancreatic cancer cell growth compared to—other GS compounds tested (FIG. 9A to 9C; Table 3). Interestingly and unexpectedly, a known compound, GS21, with very similar chemical structure to our new GS27 compound, had no effect on suppressing MIA PaCa-2 cell growth. Similarly, in HepG2 liver cancer cells (FIG. 10A to 10D; Table 4) and also in HeLa cervical cancer cells (FIG. 11A to 11D; Table 5), GS28 compound had the best efficacy to suppress their growth. In addition, in MCF-7 ER+ breast cancer cells, GS25 and GS27 had the best efficacy to suppress their growth (FIG. 12A to 12D; Table 6), while in MDA-MB-231 triple negative breast cancer cells, GS15, GS24, GS9 and GS11 showed the highest suppressive activity (FIG. 13A to 13D; Table 7). In MKN-45 gastric cancer cells, GS15 and GS28 were highly effective to suppress cell growth (FIGS. 14 to 14D; Table 8). Taken together, the development of chemical entities, such as GS27 and GS28, have unexpectedly resulted in compounds having high highly anti-cancer activity relative to the known GS compounds.

To further evaluate the improved and unexpected anti-cancer properties of the new GS compounds, their effects on HCT-116 colorectal cancer cell line at low concentration (1 μM) was investigated (FIG. 15; Table 9). Interestingly, it was found that the GS compounds that had suppressive activity were new compounds such as GS9, GS10, GS11, GS26, GS27 and GS28, while the majority of the known GS compounds did not have any effect. Thus, although there are small changes in the chemical structures of the new GS compounds relative to the known GS compounds, these structural modifications have unexpectedly resulted in compounds having potent anti-cancer activity.

Novel GS Compounds are not Toxic and do not Affect the Growth of Normal Epithelial Cells A non-tumorigenic epithelial cell line (MCF-10A) was used as control to evaluate the effects of the GS compounds on "normal" cells and evaluate potential toxicities. All GS compounds (10 µM) did not show any effects on affecting MCF-10A cell growth, except GS16 which shown some small toxicity, reducing by 10.1% the MCF-10A cell growth (FIG. 16; Table 10). This result shows that the GS compounds target cancer cell growth without affecting normal cells, thus having a good safety profile.

Figure 17:
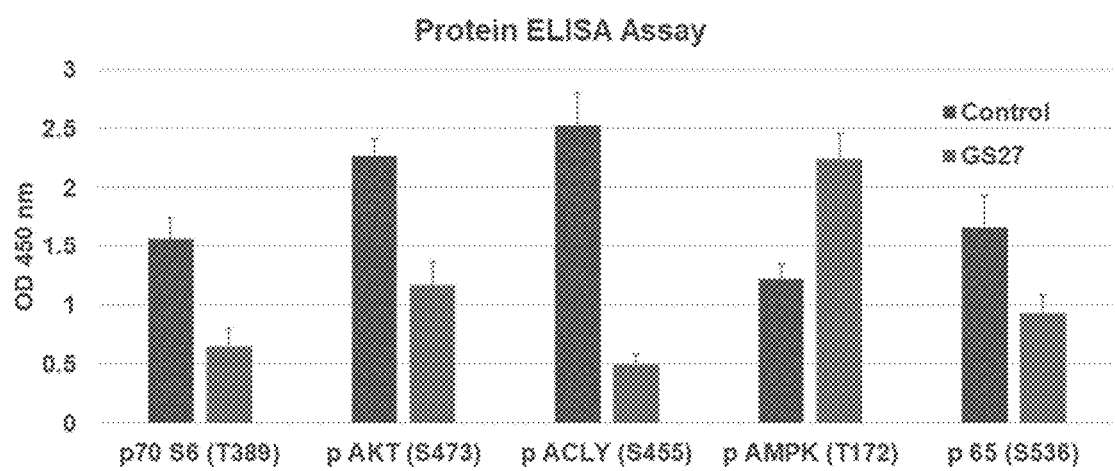
FIG. 17 shows phosphorylation levels of metabolic and inflammatory genes in PANC-1 cells treated with compound GS27.

GS27 Compound is a Key Regulator of Kinase & Enzymatic Metabolic Cancer Pathways: Targeting ATP Citrate Lyase (ACLY) Enzyme The molecular mechanism of action of GS27, a compound that has exerted potent anti-cancer activity in different cancer cell lines including pancreatic cancer cells, was investigated. Oleacein has been implicated to have anti-inflammatory and metabolic effects, thus the potential effects of GS27 in different metabolic and inflammatory pathways were evaluated. Specifically, the protein levels of p70 S6 (T389), pAKT (S473), pACLY (S455), pAMPK (T172) and p65/NFKB (S536) were evaluated by ELISA assay in PANC-1 pancreatic cancer cells treated with 5 µM GS27. GS27 reduced p70 S6 and AKT phosphorylation levels, while it increased AMPK phosphorylation. Furthermore, GS27 had a dramatic effect on reducing ACLY enzymatic activity and also inhibiting p65/NFKB activity (FIG. 17). This data suggests that GS27 is affecting key metabolic pathways, suppressing ACLY enzymatic activity and the inflammatory response through NFKB inhibition.

Specificity of GS27 to Target ACLY Enzymatic Activity

Figure 18:
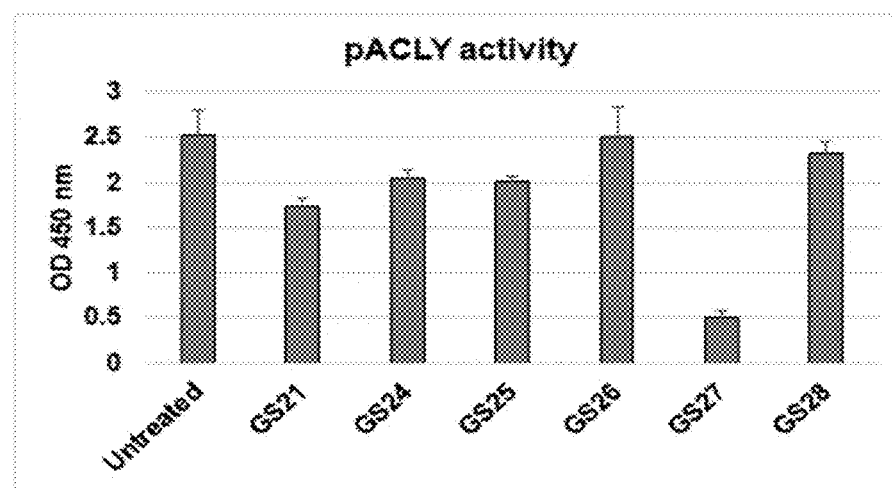
FIG. 18 shows ATP Citrate Lyase (ACLY) activity in PANC-1 pancreatic cancer cells treated with 5 μM of GS21, GS24, GS25, GS26, GS27 and GS28.

The effects of different GS compounds on ACLY enzymatic activity were evaluated by ELISA assay in PANC-1 pancreatic cancer cells. It was found that compounds GS26 and GS28 did not show any effect to reduce ACLY enzymatic activity, while compounds GS21, GS24 and GS25 showed a small effect to reduce ACLY enzymatic activity (FIG. 18). GS27 showed the best effect, substantially reducing ACLY enzymatic activity. This finding is unexpected, since GS21 has a very similar structure with GS27, with the only difference being the presence of an oxygen atom in ester GS21 instead of a sulfur atom in thioester GS27. Notably, whereas GS21 showed minimal suppression of ACLY enzymatic activity, GS27 had a huge effect.

Figure 19:
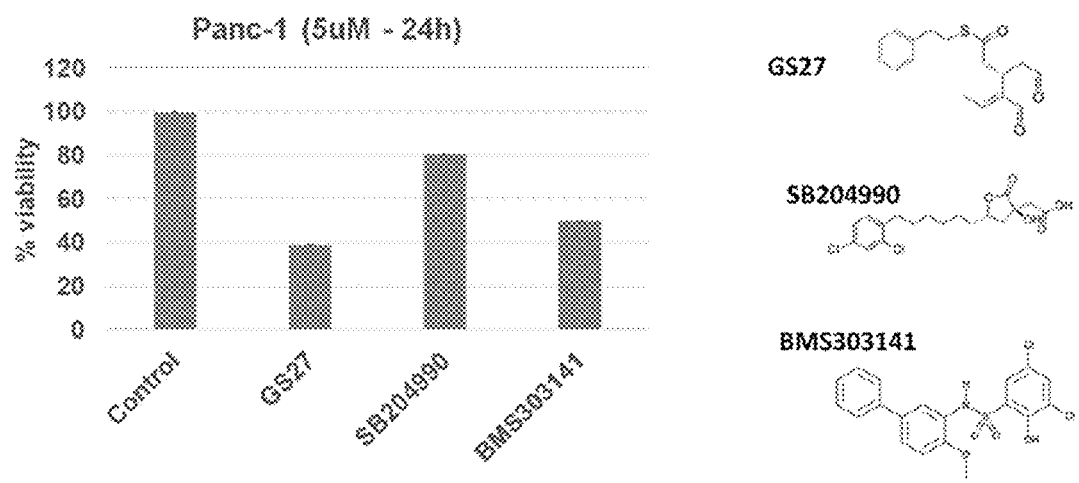
FIG. 19 shows the effects of ACLY inhibitors (GS27, SB204990, BMS303141) in PANC-1 cancer cell growth.

GS27 is More Potent in Comparison to Other ACLY Small Molecule Inhibitors to Block Pancreatic Cancer Cell Growth ATP Citrate Lyase (ACLY) is an enzyme that has been implicated in the pathobiology of different cancer cell types, including pancreatic cancer. Specifically, pancreas-specific loss of ACLY in mice, suppresses acinar to ductal metaplasia and importantly tumor formation, suggesting that ACLY is a key factor on pancreatic oncogenesis (Caner, Alessandro et al., Cancer Discovery, March 2019, 9(3): 417-435, "Acetyl-CoA Metabolism Supports Multistep Pancreatic Tumorigenesis"). Due to the fact that GS27 is a potent inhibitor of ACLY enzymatic activity (as shown in FIG. 18), its anti-cancer activity was compared relative to SB204990 (cat. No 4962, Tocris) and BMS303141 (cat. No 4609, Tocris) compounds using the Cell Titer-Glo® Luminescent Cell Viability assay. Thus, PANC-1 cancer cells were treated with 5 µM of GS27, SB204990 and BMS303141 for 24 hours. SB204990 is a potent and specific inhibitor of ACLY. BMS303141 is a potent, cell permeable ACLY inhibitor with an IC50 of 0.13 µM. Surprisingly, GS27 had the best effect on suppressing PANC-1 cancer cell growth relative to the other ACLY inhibitors (FIG. 19).

Taken together, the data presented herein suggests that GS27 is a potent inhibitor of ACLY enzymatic activity, effectively inhibiting pancreatic cancer cell growth. This suggests that GS27 could have therapeutic potential in other cancer types associated with overexpression of ACLY, such as colon, lung, breast, prostate and kidney cancers (Hatzivassiliou, Georgia et al. Cancer Cell, 2005, 8(4): 311-321, "ATP citrate lyase inhibition can suppress tumor cell growth").

ADME Properties of GS Compounds

Since GS22, GS24, GS26, GS27 and GS28 showed potent anti-cancer activity in different cancer cell lines, their ADME (absorption, distribution, metabolism and excretion) properties were examined using the Swiss ADME software. As shown in Table 11 below, it was found that several GS compounds have favorable properties according to the Lipinski's rules of drug development. Specifically, all compounds have molecular weight (MW) less than 500, topological polar surface area (TPSA) less than 120 and Log P less than 5.

TABLE 11

ADME properties of some GS compounds

| Compound No. | MW (g/mole) | TPSA | Log P |
|---|---|---|---|
| GS22 | 294.39 | 60.44 | 3.07 |
| GS24 | 304.34 | 69.67 | 2.24 |
| GS26 | 408.61 | 60.44 | 6.25 |
| GS27 | 304.4 | 76.51 | 2.95 |
| GS28 | 272.36 | 85.74 | 2.03 |

Potential Effects of GS Compounds on Intestinal Permeability

All synthesized GS compounds were examined for their potential effects on intestinal permeability using the Caco-2 cell permeability assay. Caco-2 cells are a human colon epithelial cancer cell line used as a model of human intestinal absorption of drugs and other compounds. When cultured as a monolayer, Caco-2 cells differentiate to form tight junctions between cells to serve as a model of paracellular movement of compounds across the monolayer.

Figure 20:
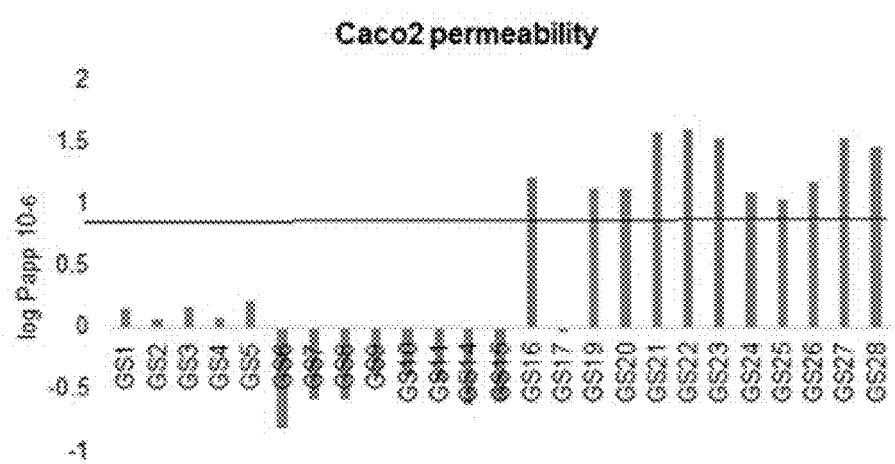
FIG. 20 shows the Caco-2 permeability of GS compounds.

In this analysis, a value higher than 0.9 indicates high intestinal permeability, while a value lower than 0.9 indicates lower intestinal permeability. It was found that most GS compounds have very low and poor intestinal permeability. On the other hand, it was unexpectedly found that a group of novel GS compounds (i.e., GS24, GS25, GS26, GS27, GS28) have values higher than 0.9, thus a highly favorable profile for further drug development and application in humans (FIG. 20).

Potential Effects of GS Compounds on P-Glycoprotein Substrate

P-glycoprotein (also P-gp or ABCB1) is an ABC transporter protein that acts as an energy dependent efflux pump, transporting out of cells a wide variety of compounds. This transporter is expressed in many normal tissues such as intestine, liver, kidney, lung, and endothelia of brain, testis, and placenta, consistent with its role as a natural detoxification system. By this activity it can have a profound impact on the pharmacokinetics and pharmacodynamics of many drugs. In particular, P-gp has been shown to limit oral absorption, modulate hepatic, renal, or intestinal elimination, and restrict central nervous system entry of certain drugs. In addition, because of its broad substrate specificity, P-gp mediated drug-drug interactions may occur when substrates, inducers, and inhibitors are co-administered. Moreover, P-gp is highly expressed in many cancer cells and multidrug resistance mediated by P-gp represents a serious problem for the development of effective anticancer drugs. Consequently, there is a great interest in anticipating whether drug candidates are P-gp substrates or inhibitors. (Crivori, Patrizia et al. Molecular Pharmaceutics, 2005, 3(1); 33-44, "Computational Models for Identifying Potential P-Glycoprotein Substrates and Inhibitors").

SwissADME® software (accessible at http://www.swissadme.ch) was used to evaluate the medicinal chemistry friendliness of the novel GS compounds (See, Daina, Antoine f SwissADME: a free web tool to evaluate pharmacokinetics, drug-likeness and medicinal chemistry friendliness of small molecules. *Sci. Rep.* 7, 42717; doi: 10.1038/srep42717). The SMILES for each GS compound was entered to this software which predicted the potential of the compound to act as a P-glycoprotein substrate.

Figure 21:
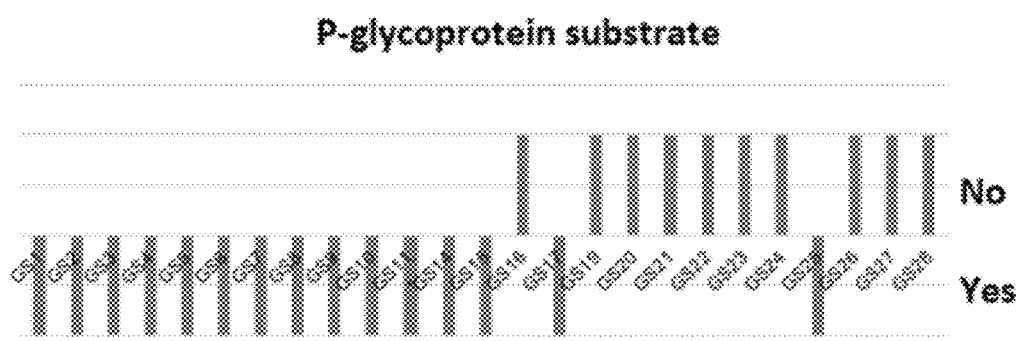
FIG. 21 shows in silico prediction of GS compounds as substrates of P-glycoprotein.

The natural GS compounds (GS1, GS6, GS7), including some novel GS compounds are predicted to be substrates of P-gp (FIG. 21). Substrates of P-gp are not only subject to multidrug resistance in cancer therapy, they are also associated with poor pharmacokinetics. Significantly, many GS compounds are predicted not to be substrates of P-gp, including GS16, GS19, GS20, GS21, GS22, GS23, GS24, GS26, GS27 and GS28.

Predicted Enzyme Targets of GS Compounds

The Swiss Target Prediction 2019 in silico model was used to identify enzyme targets of GS22, GS24, GS26, GS27 and GS28 based on their chemical structure. Swiss Target Prediction is an online tool that predicts the most probable protein targets of small molecules based on a combination of 2D and 3D similarity with known ligands. The predictions are performed by searching for similar molecules within a library of 376,342 compounds known to be experimentally active on an extended set of 3068 protein targets The results are show in Table 12.

TABLE 12

Predicted Enzyme Targets for some GS Compounds

| Compound No. | Target 1 | Target 2 |
|---|---|---|
| GS22 | FNTA | MAPK14 (p38) |
| GS24 | PDE10A | VEGRF2 |
| GS26 | HMG-CoAR | MET |
| GS27 | ACLY | MAPK14 |
| GS28 | CDK2 | CDK4 |

According to docking analysis using Swiss Target Prediction 2019, farnesyltransferase/geranylgeranyltransferase type-1 subunit alpha (FNTA) was identified as a possible target of GS22. FNTA is overexpressed in glioblastomas, head & neck cancer and genitourinary (renal, bladder, prostate) cancers.

According to docking analysis using Swiss Target Prediction 2019, phosphodiesterase 10A (PDE10A) was identified as a possible target of GS24. PDE10A is overexpressed in colon and lung cancers.

According to docking analysis using Swiss Target Prediction 2019, β-hydroxy-β-methylglutaryl coenzyme A reductase (HMG-CoAR) was identified as a possible target of GS26. HMG-CoAR is overexpressed in liver, colon and pancreatic cancers.

According to docking analysis with Swiss Target Prediction 2019, ATP citrate lyase (ACLY) was identified as a possible target of GS27. ACLY is a key enzyme in the pathogenesis of pancreatic, lung, prostate, bladder, liver and colon cancers. The inhibition of ACLY enzymatic activity was subsequently verified experimentally. It was found that GS27 substantially reduces ACLY enzymatic activity. Thus, GS27 is a potential therapeutic compound for ACLY-driven cancer type.

According to docking analysis using Swiss Target Prediction 2019, cyclin-dependent kinase 2 (CDK2) and cyclin-dependent kinase 4 (CDK4) were identified as possible targets of GS28. The main therapeutic potential of CDK2/CDK4 inhibitors, such as GS28, is in breast, liver, lung, and renal cancers and gliomas.

Example 30—Additional Studies with GS24 and GS25

It is well known and described in the scientific literature that pro-inflammatory cytokines are activated during the development of different inflammatory disorders, including gastrointestinal inflammatory disorders, autoimmune and cardiovascular disorders and during viral infections. Furthermore, pro-inflammatory cytokines, such as interleukin 1-beta (IL-1β) and tumor necrosis factor alpha (TNF-α) have been correlated with the pathogenesis of multiple inflammatory disorders and consist very important therapeutic targets.

Specifically, IL-1β is a therapeutic drug target for arthritis (Ruperto, Nicolino et al., N Engl J Med, 2012, 367:2396-2406), Crohn's Disease (Al-Sadi, Rana et al., J Interferon Cytokine Res, 2012, 32(10):474-484), atopic dermatitis (Bernard, Marine et al., J Pathol, 2017, 242(2):234-245), Behcet's disease (Chekaoui, Arezki et al., Eur Cytokine Netw, 2018, 29(3):95-102) and atherosclerosis (Bhaskar, Vinay et al.; Atherosclerosis, 2011, 216(2):313-320).

Also, TNF-α has been implicated in the pathogenesis of ulcerative colitis (Rutgeerts, Paul et al., N Engl J Med, 2005, 353:2462-2476, 2005), psoriasis (Chima Margot et al., Semin Cutan Med Surg, 2018, 37(3):134-142), psoriatic arthritis (Tobin, Anne-Marie et al., BioDrugs, 2005, 19(1): 47-57) and rheumatoid arthritis (Radner, Helga et al., Wien Med Wochenschr, 2015, 165(1-2):3-9).

Furthermore, interleukin 6 (IL-6) is involved in the pathogenesis of different inflammatory diseases, including rheumatoid arthritis, juvenile idiopathic arthritis, adult-onset Still's disease, giant cell arteritis and Takayasu arteritis, as well as other conditions such as Castleman disease and cytokine release syndrome (Choy, Ernest H. et al., Nature Reviews Rheumatology, 2020, 16: 335-345). More recently, IL-6 was found to be hyperactivated in patients infected with SARS-CoV-2, correlating with development of severe pneumonia (Cruz, Andre Santa et al., Front Immunol., 2021, 12: 613422). Thus, IL-6 inhibition could have therapeutic potential in COVID-19 infected patients.

Very recently, it has been identified that the severe acute respiratory syndrome corona virus 2 (SARS-CoV-2) induces a cytokine storm, activating both IL-1β and TNF-α pro-inflammatory cytokines, resulting in the development of severe clinical manifestations in COVID-19-infected patients (Ye, Qing et al., J Infect. 2020, 80(6):607-13). This cytokine storm is a major cause of acute respiratory distress syndrome (ARDS) and multiple-organ failure, ultimately causing death (Chousterman, Benjamin G. et al., Semin Immunopathol, 2017, 39(5):517-528). Importantly, inhibition of IL-1 pathway is associated with reduced mortality in patients experiencing a cytokine storm (Shakoory, B. et al., Crit Care Med. 2016, 44(2):275-281).

Effect of GS24 and GS25 on Inflammatory Cytokine Production

Human monocytes (THP-1, ATCC) were cultured in RPMI 1640 media supplemented with HEPES buffer (10 mM), sodium pyruvate (1 mM), glucose (4.5 g/L), fetal bovine serum (10%), penicillin (100 U/mL), streptomycin (100 µg/mL), and 2-mercaptoethanol (0.05 mM). THP-1 cells were treated with PMA (100 ng/ml) for 48 hours and then washed and rested for 24 hours in PMA-free media. These cells were treated with LPS (100 ng/ml) for 24 hours in the presence or absence of 5 uM of GS24 or GS24 compounds (added 2 hours before LPS). Cell culture supernatants were collected and IL-1β (cat. No DLB50, R&D Systems), TNF-α (cat. no. DTA00D, R&D Systems) and IL-6 (cat. No D6050, R&D Systems) protein levels were evaluated by ELISA assay.

Figure 22:
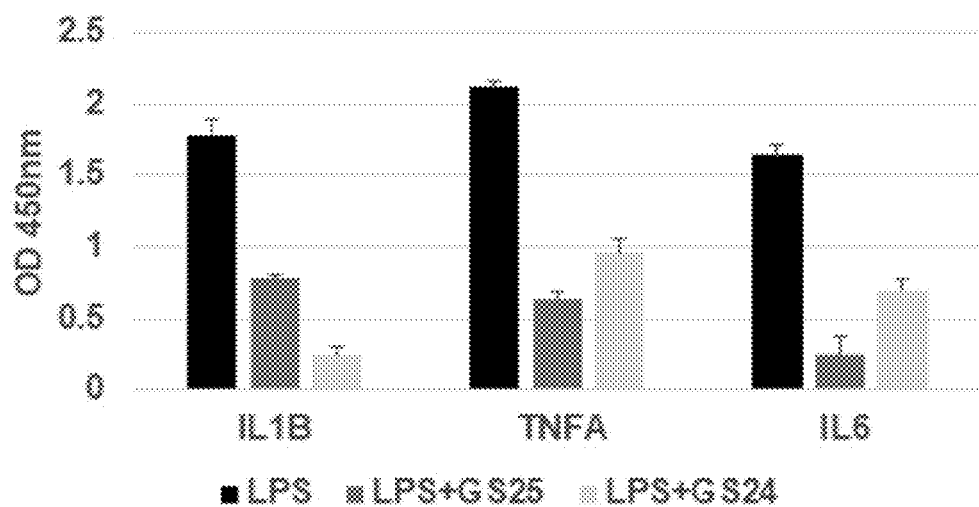
FIG. 22 shows IL-1β, TNF-α and IL-6 protein levels evaluated by ELISA assay in supernatant of PMA/LPS-treated THP-1 immune cells after treatment with GS24 or GS25.

It was found that both GS24 and GS25 compounds have anti-inflammatory activity, reducing substantially the levels of IL-1(3, TNF-α and IL-6 pro-inflammatory cytokines in human macrophages (FIG. 22). Specifically, it was found that GS24 more effectively reduced IL-1β protein levels, while GS25 had a better effect on the suppression of TNF-α protein levels. Furthermore, both GS24 and GS25 were effective for reducing IL-6 protein levels. Taken together, these results suggest that GS24 and GS25 inhibit the production of IL-1(3, TNF-α and IL-6 cytokines, which are key drivers for different inflammatory disorders as described above. Furthermore, although there are drugs that separately target IL-1(3, TNF-α and IL-6 levels, to our knowledge there are no small molecule compounds that effectively block all three cytokines, thus suppressing more effectively the cytokine storm induced by viruses such as SARS-CoV-2.

Example 31—Additional Studies with GS27

We used the following methodologies to evaluate the safety profile and efficacy of GS7 to suppress cancer growth in vitro and in vivo. Specifically, the effects of GS27 on normal immune cell growth and epithelial cell growth were examined in macrophages and mammary epithelial cells, respectively. In addition, we treated rodents with ascending doses of GS27 to identify GS27 concentrations that do not induce any death and toxicities, monitored by weight loss. Furthermore, the anti-cancer effects of GS27 were examined in mouse cancer xenograft studies, where human cancer cells were injected in mice and the effects of GS27 were evaluated by monitoring tumor size growth.

Effect of GS27 on Raw 264.7 Macrophage Cell Growth

The effect of GS27 on the growth of Raw 264.7 cells was evaluated to examine GS27 potential toxicity effects. RAW 264.7 cells are macrophage-like Abelson leukemia virus transformed cell line derived from BALB/C mice. The cell line was obtained from ATCC.

Figure 23:
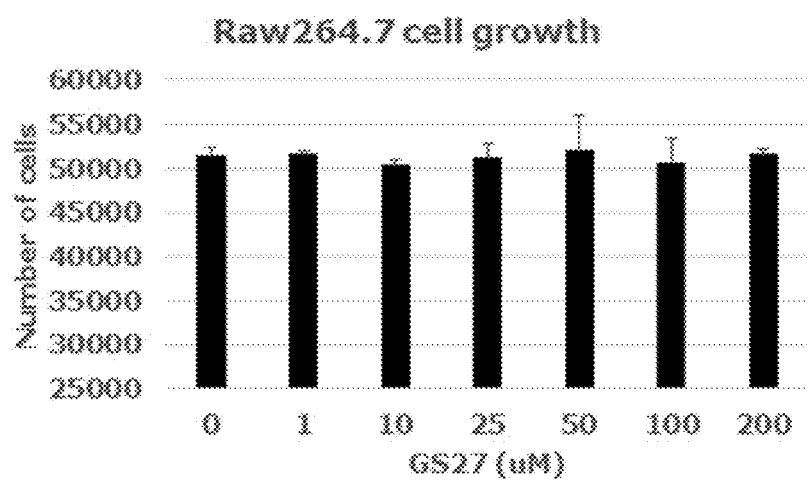
FIG. 23 shows the effect of GS27 on Raw 264.7 macrophage cell growth.

RAW 264.7 cells were maintained at 37° C., in a 5% $CO_2$ and 100% humidity incubator and grown in suspension, in non-adherent flasks, in RPMI 1640-Glutamax to which was added 50 U/mL of penicillin, 50 µg/mL streptomycin and 10% (v/v) fetal bovine serum (FBS). These cells were exposed to increasing doses of GS27 (1, 10, 25, 50, 100, 200 µM) for 24 h and after the exposure period, the cells were harvested with trypsin-EDTA and trypan blue was applied to the cell suspension. Non-colored and blue cells were counted while using an automated cell counter. GS27 was found to have no effect on Raw 264.7 cell growth (FIG. 23).

Effect of GS27 on MCF-10A Normal Cell Growth

The effect of GS27 on normal cell growth was evaluated using the MCF-10A cell line. The cell line was obtained from ATCC (cat. No. CRL-10317). MCF-10A cells are non-malignant breast epithelial cells.

GS27, NDI-091143 and Nexletol (10 µM) were used to treat normal epithelial cells MCF-10A cells. NDI-091143 and Nexletol are potent inhibitors of human ATP-citrate lyase (ACLY). Forty-eight hours post-treatment, the growth of MCF-10A cells was evaluated by CellTiter-Glo® Luminescent Cell Viability Assay, as discussed in Example 29. It was found that GS27 did not have any effect on their growth, thus GS27 is specific on killing only cancer cells.

Figure 24:
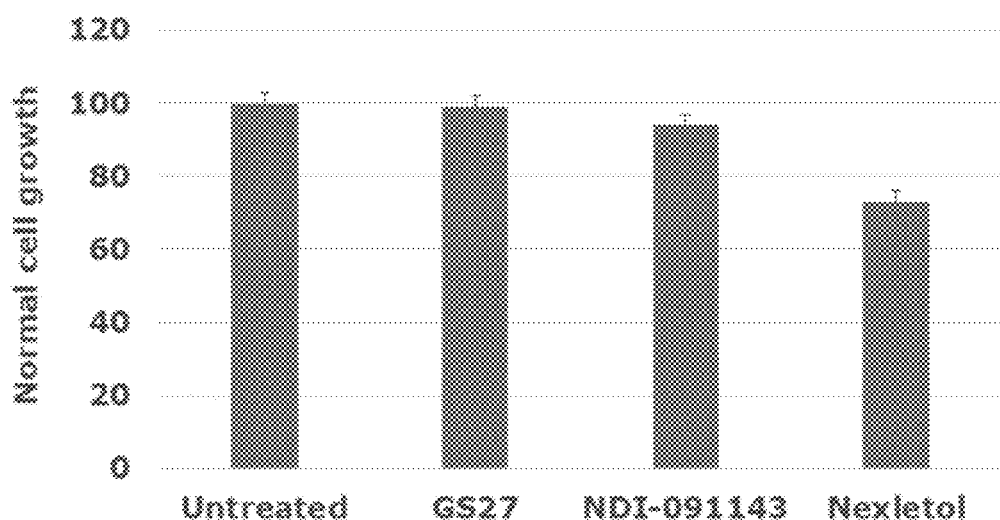
FIG. 24 shows the effect of GS27 and other ACLY inhibitors on MCF-10A normal cell growth.

In comparison, Nexletol has an inhibitory effect on MCF-10A cell growth (FIG. 24). Thus, GS27 shows a better safety profile than known ACLY-inhibitors because it does not affect normal cell growth.

GS27 Maximum Tolerated Dose (MTD) Studies in Rodents

The guidelines of the NCI DTP (National Cancer Institute, Developmental Therapeutics Program, NIH, USA) for acute toxicity testing (DOI: 10.1021/acs.biomac.8b00959) were followed to determine Maximum Tolerated Dose (MTD) of GS27.

For the MTD studies, NOD.CB 17-Prkdc$^{scid}$/J mice (also known as NOD SCID mice) were used. All animals for in vivo experiments were kept under specific pathogen-free (SPF) conditions in Type II Long cages, at the experimental unit of our department (Department of Pharmacology, EL42-BIO_Exp03, protocol license 5542/22806-30/11/2015) in a climate-regulated environment (21±1° C.; 50-55% relative humidity) under a 12 h/12 h (lights on at 7:00 AM) light/dark cycle and allowed ad libitum food and water. Female and male mice, 6-8 weeks old, were used in the studies described here. GS27 compound was administered to 15 female mice at two different doses. GS at either 100 or 50 mg/kg was administered in a single dose via i.p. injection in pre-weighed mice. One group of five mice received the carrier and served as controls. Following GS27 administration, mice were observed for 15 and 30 minutes one hour and daily to detect and record any signs of toxicity. Mice were also weighed twice weekly for two weeks.

Figure 25A:
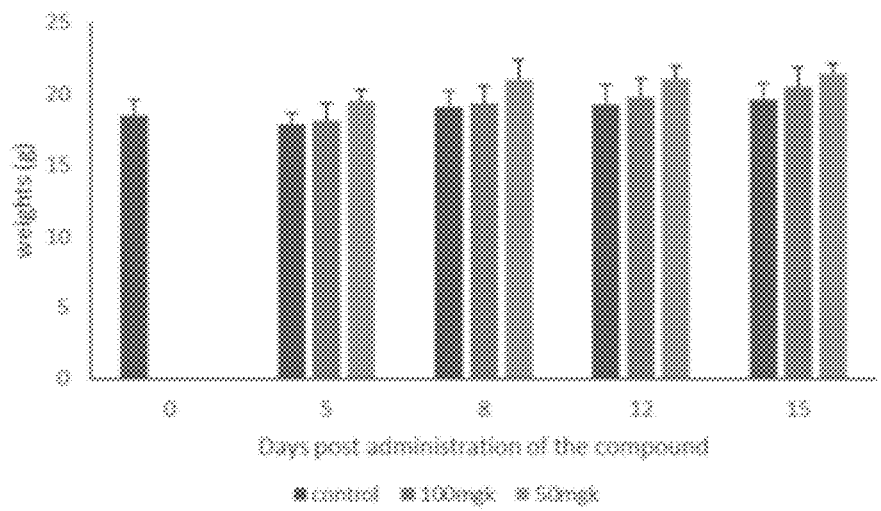
FIG. 25A and FIG. 25B show the results of GS27 Maximum Tolerated dose (MTD) studies in rodents.
Figure 25B:
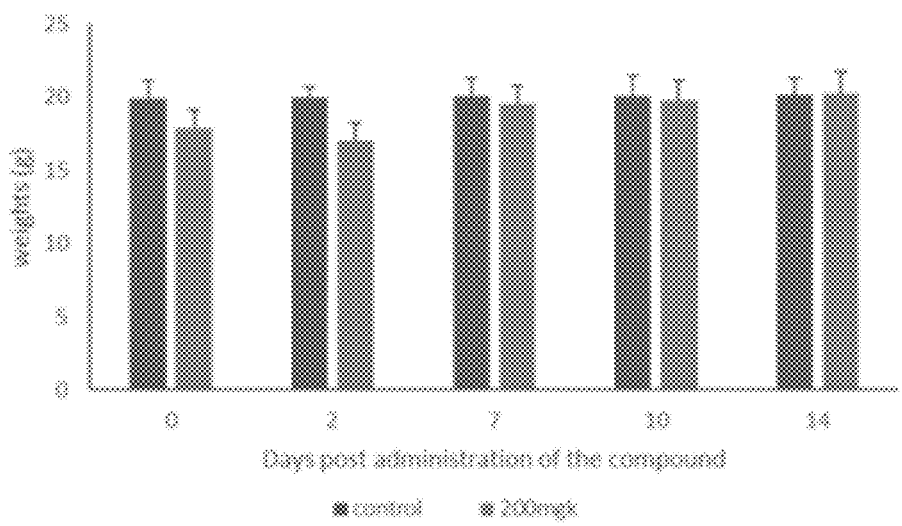

The MTD studies showed that GS27 was well tolerated up to 100 mg/kg for two weeks. There were no changes in animal weights for the study period and no behavioral or neurological changes were observed in groups that received either 100 or 50 mg/kg (FIG. 25A). The 100 mg/kg administration was performed twice using both male and female mice. In both cases, no signs of toxicity were observed for the 14 days of the study. Furthermore, there was no toxicities identified in mice treated with 200 mg/kg GS27 (FIG. 25B). Thus, the MTD of GS27 is greater than 200 mg/kg.

Effect of GS27 on Castration-Resistant Prostate Cancer Cells

The effect of GS27 on castration-resistant prostate cancer cells was evaluated, alone and in combination with enzalutamide (ENZ). Enzalutamide (XTANDI; Astellas Pharma), is an androgen receptor inhibitor used for treatment of patients with prostate cancer. In a further study, the effect of G27 in combination with ENZ on castration-resistant prostate cancer cells was compared to combination treatment of NDI-091143 with ENZ.

Figure 26:
FIG. 26 shows the effect of GS27 on castration-resistant prostate cells, alone and in combination with enzalutamide.

C4-2 Castration-resistant prostate cells cultured in androgen-depleted conditions were treated with 1 µM of GS27, in the presence or absence of 10 µM of enzalutamide (ENZ) for 72 hours. It was found that GS27 inhibited the growth of C4-2 prostate cancer cells and that the addition of enzalutamide had a substantial additive effect (FIG. 26).

Figure 27:
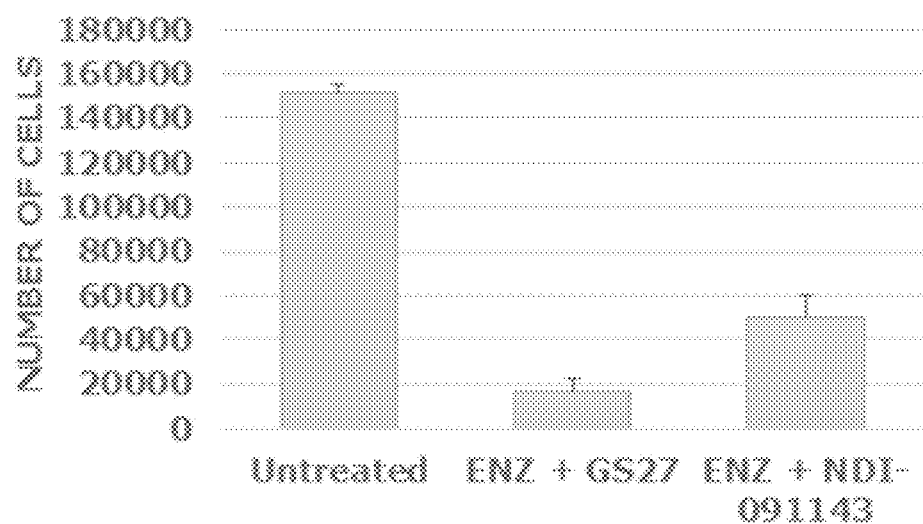
FIG. 27 shows the effect of GS27 in combination with enzalutamide on castration-resistant prostate cells compared to the effect of NDI-091143 in combination with enzalutamide.

C4-2 castration-resistant prostate cells cultured in androgen-depleted conditions were treated with 1 µM of GS27 or NDI-091143, in the presence of 10 µM of enzalutamide (ENZ) for 72 hours. GS27 inhibited the growth of C4-2 prostate cancer cells together with enzalutamide more effective than NDI-091143 and enzalutamide (FIG. 27).

Effect of GS27 on HCT-116 Colon Cancer Tumor Growth in Mice

The effect of GS27 on colon cancer tumor growth in mice was evaluated in a HCT116 xenograft mouse model. HCT-116 is a human colorectal cancer cell line that has a mutation in RAS proto-oncogene.

Xenograft tumors were generated by injecting HCT-116 colon cancer cells ($5 \times 10^6$) into the right flank of female nu/nu mice (Charles River Laboratories). All mice developed tumors in 10 days with size of approximately 100 mm3. For each experiment, mice were randomly distributed into equal groups (4 mice per group) that were untreated, or treated by intraperitoneal injections every 5 days with 20 mg/kg GS27 or GS19 (oleocanthal). Tumor volume (average, SD) was evaluated until 20 days post-treatment.

Figure 28:
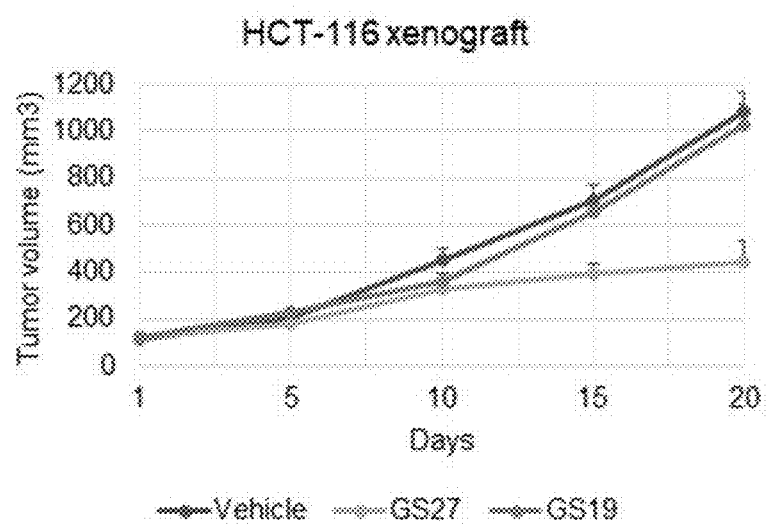
FIG. 28 shows the effects of GS27 and GS19 on HCT-116 colon cancer tumor growth in mice.

GS27 treatment showed a significant (>60% tumor size inhibition, p<0.001) effect on HCT-116 colon cancer tumor growth in mice, while GS19 treatment at the same concentration did not show any significant effect (FIG. 28).

Effect of GS27 on HepG2 Liver Cancer Tumor Growth in Mice

The effect of GS27 on liver cancer tumor growth in mice was evaluated in a HepG2 xenograft mouse model. HepG2 is a human liver cancer cell line, obtained from ATCC (cat. No HB-8065). Since hepatocellular carcinoma is often treated with the chemotherapeutic agent doxorubicin and embolization, results were compared to those obtained with doxorubicin.

Xenograft tumors were generated by injecting HepG2 liver cancer cells ($2.5 \times 10^6$) into the right flank of female nu/nu mice (Charles River Laboratories). All mice developed tumors in 10 days with size of approximately 100 mm3. For each experiment, mice were randomly distributed into equal groups (4 mice per group) that were untreated, or treated by intraperitoneal injections every 5 days with 20 mg/kg GS27 or doxorubicin. Tumor volume (average, SD) was evaluated until 20 days post-treatment.

Figure 29:
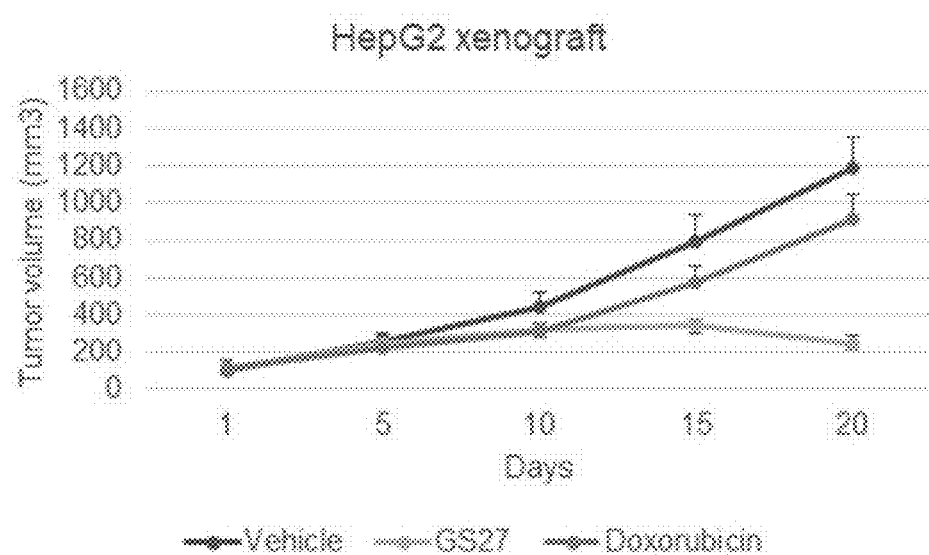
FIG. 29 shows the effects of GS27 and doxorubicin on HepG2 liver cancer tumor growth in mice.

GS27 treatment showed an 80% reduction in the tumor size in mice in comparison to 13% reduction caused by doxorubicin chemotherapy treatment (FIG. 29).

Effect of GS27 on AsPC-1 Pancreatic Cancer Tumor Growth in Mice

The effect of GS27 on pancreatic cancer tumor growth in mice was evaluated in a AsPC-1 xenograft mouse model.

Xenograft tumors were generated by injecting AsPC-1 pancreatic cancer cells ($0.5 \times 10^6$) into the right flank of male NOD/SCID mice (n=5/group). All mice developed tumors in 10 days with size of approximately 100 mm3. For each experiment, mice were randomly distributed into equal groups (5 mice per group) that were untreated or treated by intraperitoneal injections daily for 5 days with 100 mg/kg GS27. Tumor volume (average, SD) and the weight of the animals were evaluated until 24 days post-treatment.

Figure 30A:
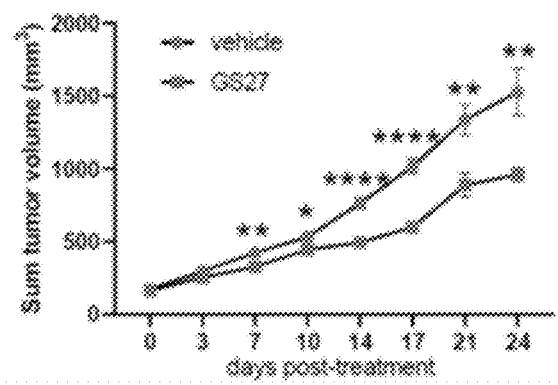
FIG. 30A and FIG. 30B shows the effects of GS27 on AsPC-1 pancreatic cancer tumor growth in mice.
Figure 30B:
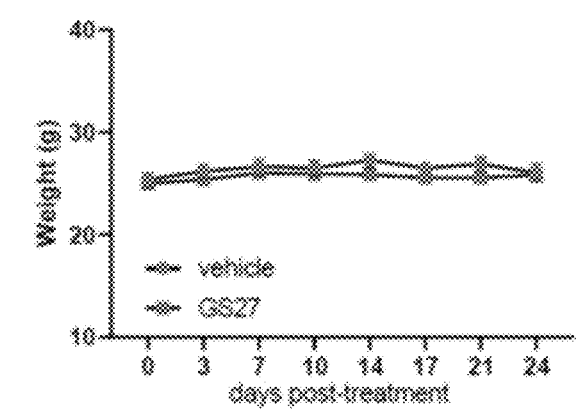

GS27 treatment showed a 34% statistically significant (p<0.01) inhibition of AsPC-1 pancreatic cancer tumor growth in mice (FIG. 30A). Furthermore, GS27 treatment did not affect the weight of the mice, indicating that GS27 was not toxic at a dose of 100 mg/kg (FIG. 30B).

Effect of GS27 on ATP-Citrate Lyase (ACLY) Enzymatic Activity

ATP-citrate lyase (ACLY) is a key metabolic enzyme involved in glucose and lipid metabolism. The conversion of glucose to fatty acids is dependent on the activity of ACLY, which converts mitochondria-derived citrate to cytosolic acetyl-CoA. ACLY expression and activity is aberrantly expressed in many types of tumors, and its pharmacological or genetic inhibition significantly inhibits cancer cell proliferation and induced apoptosis.

An ACLY Assay Kit (BPS Bioscience) was used to evaluate GS27 against ATP-citrate lyase (ACLY) enzymatic activity. The ACLY Assay Kit is designed to measure ACLY activity for screening and profiling applications using ADP-Glo™ Kinase Assay as a detection reagent (Promega #V6930). The ADP-Glo™ Kinase Assay is a luminescent ADP detection assay that provides a universal, homogeneous, high-throughput screening method to measure kinase activity by quantifying the amount of ADP produced during a kinase reaction.

Figure 31:
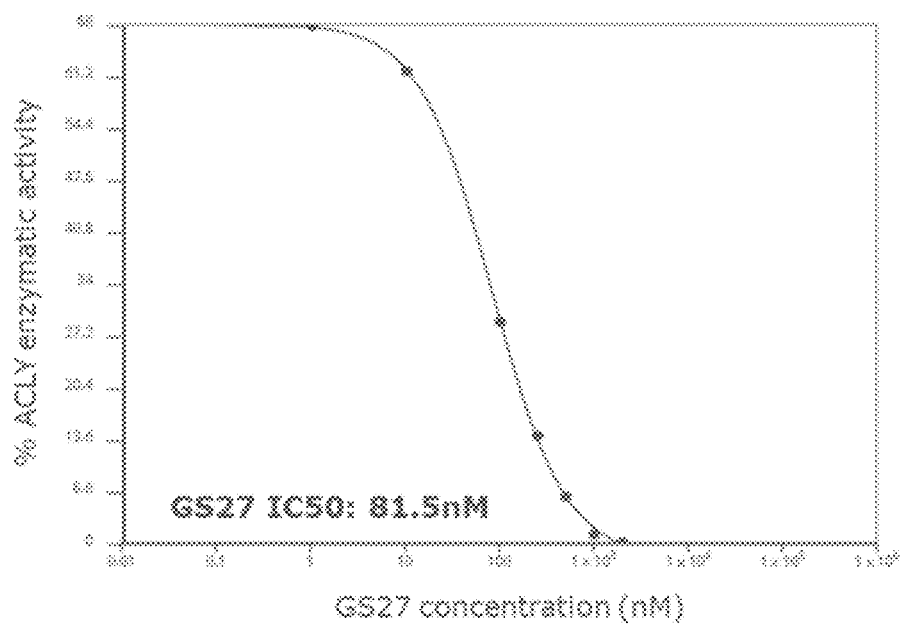
FIG. 31 shows the effect of GS27 on ATP-Citrate Lyase (ACLY) enzymatic activity.

Multiple (1, 10, 100, 250, 500, 1000, 2000 nM) GS27 concentrations were used to evaluate GS27 IC50 activity. As shown in FIG. 31, GS27 was found to be a potent inhibitor of ACLY activity, with an IC50 of 81.5 nm. GS19 (oleocanthal) and GS1 (oleuropein) were evaluated in the same assay and did not show any activity (IC50>10 µM) against ACLY enzyme.

These findings suggest that GS27 regulates ACLY enzymatic activity through bindings in its activity pocket and blocks ACLY function even at the nanomolar level. This biochemical experiment verifies that GS27 is a direct inhibitor of ACLY activity. These data are consistent with previous findings where GS27 was found to reduce ACLY activity through reduction of its phosphorylation levels.

Effect of GS27 on Lipid Content of AsPC-1 Pancreatic Cancer Tumor Cells

Figure 32:
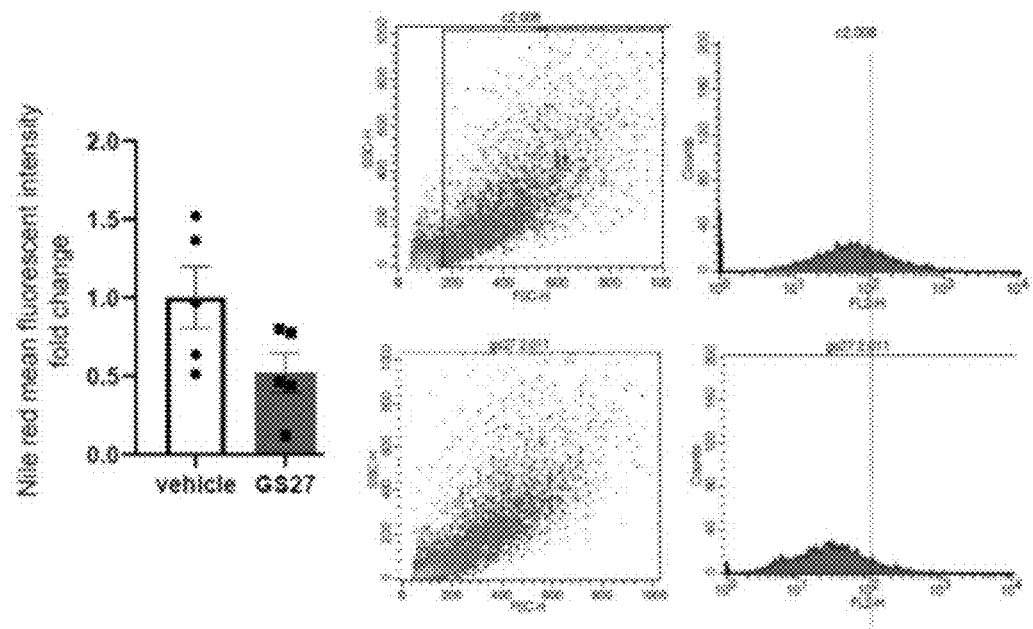
FIG. 32 shows the effect of GS27 on lipid content of AsPC-1 pancreatic cancer tumor cells.

Tumors derived from the mice treated by intraperitoneal injection with GS27 at 100 mg/kg were collected 24 days post-treatment. The tumors were evaluated for their lipid content using the dye nile red as a fluorescent vital stain for the detection of intracellular lipid droplets by fluorescence microscopy and flow cytofluorometry, as described previously (Greenspan, Peter et al., J Cell Biol, 1985, 100(3): 965-973). As shown in FIG. 32, GS27-treated tumors resulted in reduced nile red fluorescent. The top graph shows cells treated with vehicle; the bottom graph shows cells treated with G27. Quantification of the data is shown in the bar graph.

GS27-treated tumors showed a 55% reduction in the lipid content of AsPC-1 pancreatic cancer tumor cells, consistent with the finding that GS27 is a suppressor of ACLY activity, which is a key regulator of lipid metabolism.

The foregoing invention has been described in some detail by way of illustration and example, for purposes of clarity and understanding. Those skilled in the art understand that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The entirety of each patent, patent application, publication or any other reference or document cited herein hereby is incorporated by reference in their entirety for all purposes to the same extent as if each individual patent, patent application or publication were so individually denoted.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

What is claimed is:

1. A compound selected from the group consisting of:

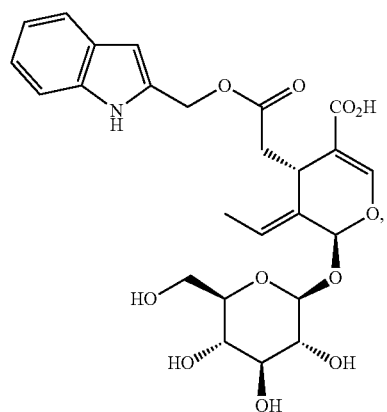

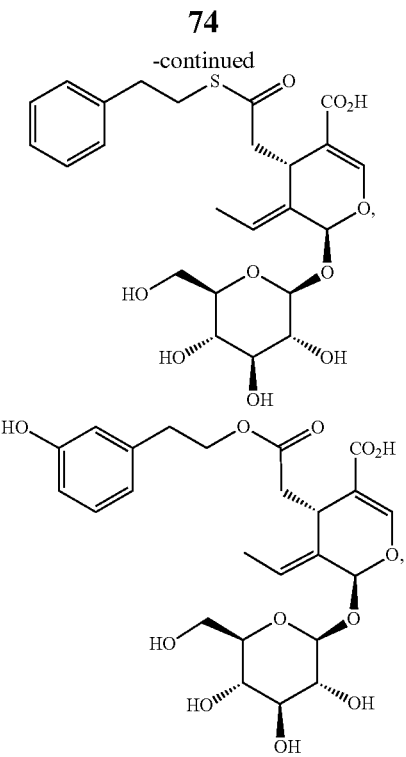

or a pharmaceutically acceptable salt thereof.

2. The compound of claim 1, wherein the compound is selected from the group consisting of:

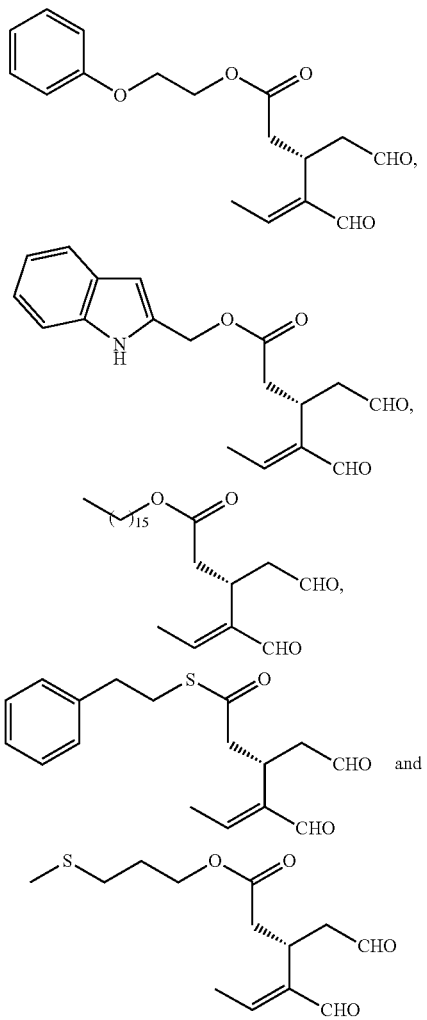

or a pharmaceutically acceptable salt thereof.

3. The compound of claim 1, wherein the compound is selected from the group consisting of:

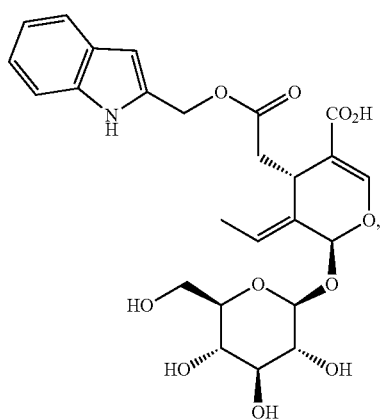

or a pharmaceutically acceptable salt thereof.

4. A pharmaceutical composition comprising a therapeutically effective amount of a compound according to claim 1 and a pharmaceutically acceptable excipient, carrier or vehicle.

5. The pharmaceutical composition of claim 4, wherein the composition further comprises one or more additional therapeutic agents.

6. A method of treating an inflammatory disorder comprising administering to a subject in need thereof a therapeutically effective amount of a compound according to claim 1.

7. The method of claim 6, wherein the inflammatory disorder is a gastrointestinal inflammatory disorder selected from the group consisting of ulcerative colitis, Crohn's disease, celial disease, primary sclerosing cholangitis, primary biliary cirrhosis, autoimmune hepatitis, eosinophilic esophagitis and Mooren's ulcer.

8. The method of claim 6, wherein the inflammatory disorder is an autoimmune inflammatory disorder selected from the group consisting of systemic lupus erythematosus, psoriasis, rheumatoid arthritis, Type 1 diabetes, multiple sclerosis, Sjogren syndrome, atopic dermatitis, Behcet's Disease and Familial Mediterranean Fever.

9. The method of claim 6, wherein the inflammatory disorder is a viral inflammatory disorder which is influenza virus infection or SARS-COV2 infection.

10. The method of claim 6, wherein the inflammatory disorder is a cardiovascular inflammatory disorder selected from the group consisting of coronary artery disease, atherosclerosis, hypercholesterolemia and hypertriglyceridemia.

11. A method of treating a cardiometabolic disorder comprising administering to a subject in need thereof a therapeutically effective amount of a compound according to claim 1.

12. The method of claim 11, wherein the cardiometabolic disorder comprises Type II diabetes, vascular disease, myocardial ischemia, coronary artery disease, atherosclerosis, thrombosis, hypertension, hypercholesterolemia, or hypertriglyceridemia.

13. A method of treating cancer comprising administering to a subject in need thereof a therapeutically effective amount of a compound according to claim 1, wherein the cancer is associated with overexpression of at least one of farnesyltransferase (FNTA), phosphodiesterase 10A (PDE10A), B-hydroxy B-methylglutaryl-coenzyme A reductase (HMG-COAR), ATP citrate lyase (ACLY), cyclin-dependent kinase 2 (CDK2), or cyclin-dependent kinase 4 (CDK4) proteins.

14. The method of claim 13, wherein the compound is selected from the group consisting of:

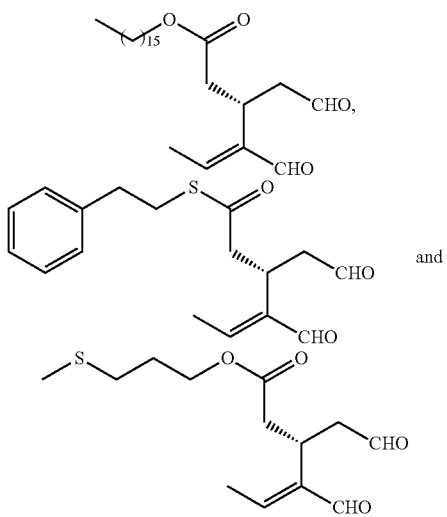

and or a pharmaceutically acceptable salt thereof.

15. The method of claim 13, wherein the cancer is a farnesyltransferase (FNTA)—associated cancer selected from the group consisting of HER2 positive breast cancer, non-small cell lung cancer (NSCLC), bladder cancer, pancreatic cancer, acute myeloid leukemia (AML), myelodysplastic syndrome, chronic myelogenous leukemia (CML) and multiple myeloma.

16. The method of claim 13, wherein the cancer is a phosphodiesterase 10A (PDE10A)—associated cancer selected from the group consisting of lung, colon and prostate cancers.

17. The method of claim 13, wherein the cancer is a β-hydroxy β-methylglutaryl-coenzyme A reductase (HMG-CoAR)—associated cancer selected from the group consisting of ovarian, breast, cancer and hepatocellular cancers.

18. The method of claim 13, wherein the cancer is an ATP citrate lyase (ACLY)—associated cancer selected from the group consisting of lung, prostate, bladder, breast, ovarian, liver, stomach, pancreatic and colorectal cancers.

19. The method of claim 13, wherein the cancer is a cyclin-dependent kinase 2 (CDK2)—associated cancer selected from the group consisting of gastric, bladder, prostate, MYNC-amplified neuroblastomas, KRAS mutant-lung cancer, CCNE-1-amplified ovarian cancer and sarcoma.

20. The method of claim 13, wherein the cancer is a cyclin-dependent kinase 4 (CDK4)—associated cancer selected from the group consisting of ER-positive breast cancer, esophageal squamous cell cancer and small cell lung cancer.

21. The method of claim 13, further comprising administrating to the subject an additional chemotherapeutic agent.

22. The method of claim 13, wherein ACLY protein is overexpressed in the cancer.

23. The method of claim 22, wherein the method comprises administration of a therapeutically effective amount of

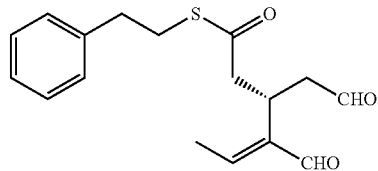 [SMILES: C/C=C(/C=O)[C@@H](CC=O)CC(=O)SCCc1ccccc1]

or a pharmaceutically acceptable salt thereof.

24. A method of inhibiting free radical damage in human skin by topical or transdermal administration to a subject in need thereof a therapeutically effective amount of a compound according to claim 1.

25. The method of claim 24, wherein the method is used for treating a condition or disorder associated with free radical damage in human skin.

26. The method of claim 25, wherein the condition or disorder associated with free radical damage comprises sun-induced skin damage, skin aging, skin inflammatory disorders, melasma, skin acne, skin wrinkles, eczema, rosacea, seborrheic dermatitis, or skin degenerative or disorders such as granuloma annulare and follicular degeneration syndrome.

27. The method of claim 26, wherein the compound is selected from the group consisting of:

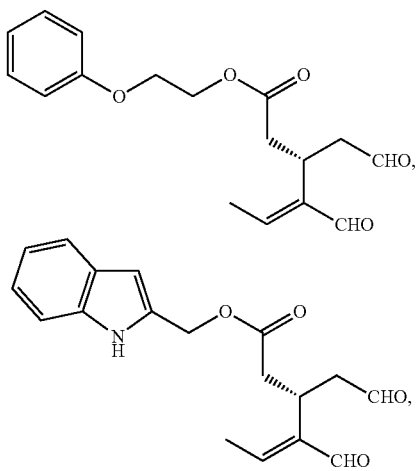

-continued

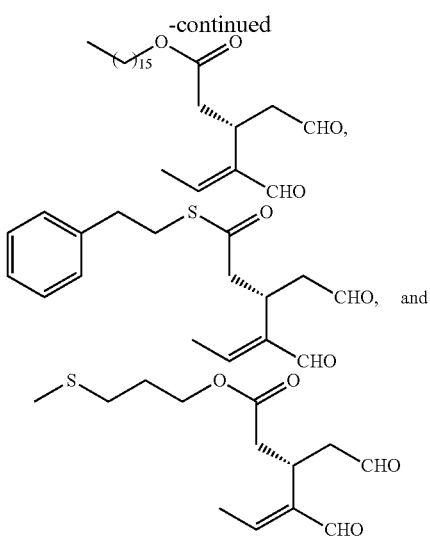

or a pharmaceutically acceptable salt thereof.

28. A method of inhibiting an ATP Citrate Lyase (ACLY)-associated disease comprising administering to a subject in need thereof a therapeutically effective amount of a compound according to claim 1, wherein the ACLY-associated disease comprises hypercholesterolemia, Type II diabetes, atherosclerosis, chronic metabolic acidosis, hepatitis C, pancreatitis, nonalcoholic fatty liver disease (NAFLD) or cancer, wherein the cancer is associated with overexpression of ACLY.

29. The method of claim 28, wherein the ACLY-associated disease is a cancer selected from the group consisting of lung, prostate, bladder, breast, ovarian, liver, stomach, pancreatic and colorectal cancers.

30. The method of claim 28, wherein the method inhibits cancer cell growth, development, or metastasis.

31. The method of claim 28, wherein the method suppresses ACLY phosphorylation and enzymatic activity in cancer cells.

32. The method of claim 28, wherein the method of inhibiting an ACLY-associated disease comprises administration of a therapeutically effective amount of:

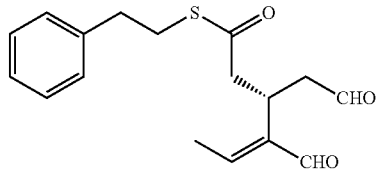

or a pharmaceutically acceptable salt thereof.

* * * * *